US009718824B2

(12) United States Patent
Klopfer

(10) Patent No.: US 9,718,824 B2
(45) Date of Patent: Aug. 1, 2017

(54) SOLID FORMS COMPRISING 7-(6-(2-HYDROXYPROPAN-2-YL) PYRIDIN-3-YL)-1-((TRANS)-4-METHOXYCYCLOHEXYL)-3,4-DIHYDROPYRAZINO[2,3-B]PYRAZIN-2(1H)-ONE, AND A COFORMER, COMPOSITIONS AND METHODS OF USE THEREOF

(71) Applicant: Signal Pharmaceuticals, LLC, San Diego, CA (US)

(72) Inventor: Kevin Klopfer, Flemington, NJ (US)

(73) Assignee: Signal Pharmaceuticals, LLC, San Diego, CA (US)

(*) Notice: Subject to any disclaimer, the term of this patent is extended or adjusted under 35 U.S.C. 154(b) by 17 days.

(21) Appl. No.: 14/686,866

(22) Filed: Apr. 15, 2015

(65) Prior Publication Data

US 2015/0299208 A1   Oct. 22, 2015

Related U.S. Application Data

(60) Provisional application No. 61/980,114, filed on Apr. 16, 2014.

(51) Int. Cl.

| C07D 487/04 | (2006.01) |
|---|---|
| A61K 31/5025 | (2006.01) |
| A61K 31/428 | (2006.01) |
| C07C 57/15 | (2006.01) |
| C07C 57/145 | (2006.01) |
| C07C 63/06 | (2006.01) |
| A61K 31/192 | (2006.01) |
| A61K 31/19 | (2006.01) |
| A61K 9/14 | (2006.01) |
| A61K 9/20 | (2006.01) |
| A61K 31/4985 | (2006.01) |

(52) U.S. Cl.
CPC ............ C07D 487/04 (2013.01); A61K 9/145 (2013.01); A61K 9/2018 (2013.01); A61K 9/2054 (2013.01); A61K 31/19 (2013.01); A61K 31/192 (2013.01); A61K 31/428 (2013.01); A61K 31/4985 (2013.01); C07C 57/145 (2013.01); C07C 57/15 (2013.01); C07C 63/06 (2013.01); C07B 2200/13 (2013.01)

(58) Field of Classification Search
CPC .............................. A61K 31/495; C07D 487/04
USPC ........................................... 514/249; 544/350
See application file for complete search history.

(56) References Cited

U.S. PATENT DOCUMENTS

| 3,507,866 A | 4/1970 | Jones et al. |
|---|---|---|
| 3,567,725 A | 3/1971 | Grabowki et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,855,723 B2 | 2/2005 | McMahon et al. |
| 7,651,687 B2 | 1/2010 | Buck et al. |
| 7,968,556 B2 | 6/2011 | Mortensen et al. |
| 7,981,893 B2 | 7/2011 | Mortensen et al. |
| 8,110,578 B2 | 2/2012 | Perrin-Ninkovic et al. |
| 8,372,976 B2 | 2/2013 | Mortensen et al. |
| 8,383,634 B2 | 2/2013 | Mortensen et al. |
| 2003/0036652 A1 | 2/2003 | Bakthavatchalam et al. |
| 2003/0162968 A1 | 8/2003 | Ciriillo et al. |
| 2004/0023921 A1 | 2/2004 | Hong et al. |
| 2004/0063658 A1 | 4/2004 | Roberts et al. |
| 2004/0097485 A1 | 5/2004 | Burkitt et al. |
| 2004/0213757 A1 | 10/2004 | Zhu et al. |
| 2005/0009737 A1 | 1/2005 | Clark |
| 2006/0004014 A1 | 1/2006 | Hoffmann et al. |
| 2006/0106022 A1 | 5/2006 | Liu et al. |
| 2006/0135511 A1 | 6/2006 | Burgey |
| 2006/0142269 A1 | 6/2006 | Dykes |
| 2007/0280928 A1 | 12/2007 | Buck et al. |
| 2008/0214580 A1 | 9/2008 | Neagu et al. |
| 2009/0069289 A1 | 3/2009 | Neagu et al. |
| 2009/0163545 A1 | 6/2009 | Goldfarb |
| 2009/0281075 A1 | 11/2009 | Roughton et al. |
| 2010/0144738 A1 | 6/2010 | Bornmann et al. |
| 2010/0249122 A1 | 9/2010 | Kalman |
| 2011/0137028 A1 | 6/2011 | Harris et al. |
| 2011/0257167 A1 | 10/2011 | Lee |
| 2012/0028972 A1 | 2/2012 | Wong |
| 2012/0059164 A1 | 3/2012 | Perrin-Ninkovic et al. |

(Continued)

FOREIGN PATENT DOCUMENTS

| CA | 2 458 699 A1 | 3/2003 |
|---|---|---|
| DE | 262 026 | 11/1988 |

(Continued)

OTHER PUBLICATIONS

Barlin, "Purine analogs as amplifiers of phleomycin. VII. Some 1H-inidazo[4,5-b]pyrazines and related compound," Australian Journal of Chemistry, vol. 35, pp. 2299-2306 (1982).

(Continued)

*Primary Examiner* — Yong Chu
*Assistant Examiner* — Sonya Wright
(74) *Attorney, Agent, or Firm* — Jones Day

(57) ABSTRACT

Provided herein are formulations, processes, solid forms and methods of use relating to 7-(6-(2-hydroxypropan-2-yl)pyridin-3-yl)-1-((trans)-4-methoxycyclohexyl)-3,4-dihydropyrazino[2,3-b]pyrazin-2(1H)-one.

53 Claims, 47 Drawing Sheets

(56) References Cited

U.S. PATENT DOCUMENTS

| | | |
|---|---|---|
| 2012/0071658 A1 | 3/2012 | Perrin-Ninkovic et al. |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2015/0099754 A1 | 4/2015 | Xu et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2006/050076 | 5/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/065703 | 6/2006 |
| WO | WO 2006/087530 | 8/2006 |
| WO | WO 2006/091737 | 8/2006 |
| WO | WO 2006/108103 | 10/2006 |
| WO | WO 2007/143212 | 12/2007 |
| WO | WO 2008/016669 | 2/2008 |
| WO | WO 2008/051493 | 5/2008 |
| WO | WO 2008/051494 | 5/2008 |
| WO | WO 2009/008992 | 1/2009 |
| WO | WO 2010/062571 | 6/2010 |
| WO | WO 2010/068483 | 6/2010 |
| WO | WO 2010/093435 | 8/2010 |
| WO | WO 2011/097333 | 8/2011 |
| WO | WO 2011/112666 | 9/2011 |
| WO | WO 2013/075059 | 5/2013 |
| WO | WO 2013/096907 | 6/2013 |
| WO | WO-2013082344 * | 6/2013 |
| WO | WO 2013/138553 | 9/2013 |
| WO | WO 2013/138556 | 9/2013 |

OTHER PUBLICATIONS

Barr et al., (2008), "Erlotinib, an EGFR kinase inhibitor, sensitizes mesenchymal-like tumor cells to the actions of OXA-01, a selective non-macrolide inhibitor of mTORC1/mTORC2," European Journal of Cancer, Supplement, vol. 6, No. 12, pp. 103-104, Poster 325 (2008).
Beresnev et al., "Interaction of 5-methoxy-1,2,4-traizines with uras as a new route to 6-azapurines," Medeleev Commu., vol. 2, pp. 58-59 (2000).
Bergmann et al., "2-Phenylpurines, their chemical and enzumological reactivity," J. Chem Org., pp. 3729-3735 (1963).
Bjornsti, M.A., & Houghton, P. J. (2004). The TOR pathway: a target for cancer therapy. Nature Reviews Cancer, 4(5), 335-348.
Blanco et al.(2009). A gene-alteration profile of human lung cancer cell lines. Human mutation, 30(8), 1199-1206.
Booth et al., "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675 (1995).

Booth et al., "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. pp. 2119-2126 (1992).
Booth et al., "The Reactions of Diaminomaleonitrile with Isocyanates and Either Aldehydes or Ketones Revisited," J. Org Chem, vol. 66, pp. 8436-8441 (2001).
Booth, et al., "Synthesis of 4- and 5-Disubstituted 1-Benzylimidazoles, Important Precursors of Purine Analogs," J. of Heterocyclic of Chemistry, vol. 31(2), pp. 345-350 (1994).
Buck et al., "Rapamycin synergizes with the epidermal growth factor receptor inhibitor erlotinib in non-small-cell lung, pancreatic, colon, and breast tumors," Molecular Cancer Therapeutics, vol. 5, No. 11, pp. 2676-2684 (2006).
Carretero et al., "Integrative Genomic and Proteomic Analyses Identify Targets for Lkb1-Deficient Metastatic Lung Tumors," Cancer Cell, vol. 17( 6), pp. 547-559 (2010).
Chupakhin et al., "A simple one pot synthesis of condensed 1,2,4-triazines by using the tandem $A_N—S_Nipso$ and $S_N^H—S_Nipso$ reactions," J. of Heterocyclic Chemistry, vol. 38(4), pp. 901-907 (2001).
Cohen, "The role of protein phosphorylation in human health and disease," Eur. J. Biochem, vol. 268, pp. 5001-5010 (2001).
Cohen, P. "Protein kinases—the major drug targets of the twenty-first century?" Nature Reviews/Drug Discovery, vol. 1, pp. 309-315 (2002).
Coish, et al., "Small molecule inhibitors of IKK kinase activity," Expert Opin. Ther. Patents, vol. 16(1), pp. 1-12 (2006).
Costa et al., "Aspects of mTOR biology and the use of mTOR inhibitors in non-Hodgkin's lymphoma," Cancer Treatment Reviews, Saunders, US, vol. 33(1), pp. 78-84 (2007).
Crofts et al., "Metabolism of 2-amino-1-methyl-6-phenylimidazo[4,5-b]pyridine (PhIP) by human cytochrome P4501B1," Carcinogenesis, vol. 18(9), pp. 1793-1798 (1997).
Dang et al., "Efficient synthesis of purines and purine nucelosides via an inverse electron demand diels-alder reaction," J. Am Chem Soc., vol. 121(24), pp. 5833-5834 (1999).
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).
Database Caplus Online Chemical Abstracts Service, Columbus, Ohio, Database Accession No. 1966:26849 (XP-002472263) (1965).
Dornow et al., "Synthese von2-Oxy-imidazolo-(5',4':2,3)-pyridinen)," Arch Pharm. vol. 290, pp. 20-31 (1957) (w/English language abstract).
Dorwald F. "Side Reactions in Organic Synthesis: A Guide to Successful Synthesis Design," Weinheim: Wiley-VCH Verlag GmbH & Co. KgaA, Preface. (2005).
Dzierba et al., "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23), pp. 5783-5790 (2004).
EPO Supplementary European Search Report dated Feb. 8, 2013 issued in connection with PCT/US2010/053678.
Fabbro et al., "Protein kinases as targets for anticancer agents: from inhibitors touseful drugs," Pharmacology & Therapeutics, vol. 93, pp. 79-98 (2002).
Farhadi et al., "The role of protein kinase C isoforms in modulating injury and repair of the intestinal barrier," J. Pharm Exp. Ther., vol. 316(1), pp. 1-7 (2006).
Frandsen et al., "Reaction of the N2-acetoxy derivative of 2-amino-1-methyl-6-phenylimidazo[4,5,b] pyridine . . . ," Carcinogenesis, vol. 13(4), pp. 629-635 (1992).
Frost et al., "AKT activity regulates the ability of mTOR inhibitors to prevent angiogenesis and VEGF expression in multiple myeloma cells," ONCOGENE, vol. 26(16), pp. 2255-2262 (2007).
Gao et al., "LKB1 in lung cancerigenesis: a serine/threonine kinase as tumor suppressor," Protein & Cell, vol. 2(2), pp. 99-107 (2011).

(56) References Cited

OTHER PUBLICATIONS

Gao et al., "LKB1 inhibits lung cancer progression through lysyl oxidase and extracellular matrix remodeling," Proceedings of the National Academy of Sciences, vol. 107(44), pp. 18892-18897 (2010).

Georgakis and Younes, "From rapi nui to rapamycin: targeting PI3K/Akt/mTOR for cancer therapy," Expert Rev. Anticancer Ther., vol. 6(1), 131-140 (2006).

Gokmen-Polar et al., (2012), "Investigational drug MLN0128, a novel TORC1/2 inhibitor, demonstrates potent oral antitumor activity in human breast cancer xenograft models," Breast Cancer Research and Treatment, Oct. 21, 2012, pp. 673-682, 136(3), Kluwer Academic Publishers, Bo.

Gulati et al. "Involvement of mTORC1 and mTORC2 in regulation of glioblastoma multiforme growth and motility," International Journal of Oncology, vol. 35(4) (2009), abstract.

Hamad, "A new synthesis of 4-cyano-1,3-dihydro-2-oxo-2$H$-imidazole-5-($N^1$-tosyl)carboxamide: Reactive precursor for thiopurine analogues," J of Heterocyclic Chemistry, vol. 38(4), pp. 939-944 (2001).

http://www.sigmaaldrich.com/catalog/product/ALDRICH/678740?lang=en&region=US, last accessed Nov. 1, 2012.

http://www.sigmaaldrich.com/catalog/product/ALDRICH/701602?lang=en&region=US#, last accessed Nov. 1, 2012.

http:/lwww.sigmaaldrich.com/catalog/product/aldrich/697230?lang=en&region=US, last accessed Nov. 1, 2012.

http:/lwww.sigmaaldrich.com/chemistry/chemical-synthesis/technology-spotlights/catalysisapplicationguide.html, last accessed Nov. 1, 2012.

Huang et al., "Genetic and epigenetic silencing of SCARA5 may contribute to human hepatocellular carcinoma by activating FAK signaling," Journal of Clinical Investigation, vol. 120(1), pp. 223-241 (2010).

Inge et al., "Expression of LKB1 tumor suppressor in non-small cell lung cancer determines sensitivity to 2-deoxyglucose," Journal of Thoracic and Cardiovascular Surgery, vol. 137(3), pp. 580-58 (2009).

Irie et al., "Toward the development of new medicinal leads with selectivity for protein kinase C isozymes," The Chemical Record, vol. 5, pp. 185-195 (2005).

Itoh et al., "A novel practical synthesis of C-2-arylpurines," Advanced Synthesis & Catalysis, vol. 346, pp. 1859-1867 (2004).

Jones et al.,"6-Substituted-5-chloro-1,3-dihydro-2H-imidazo(4,5-b)pyrazin-2-ones with hypotensive activity," J. Med. Chem., vol. 16(5), pp. 537-542 (1973).

Jordan, V.C., Nature Reviews: Drug Discover, vol. 2, p. 205 (2003).

Kazaoka et al., "Synthesis of 6-substituted 9-benzyl-8-hydroxypurines with potential interferon-indcuing activity," Chemical & Pharmaceutical Bulletin, vol. 51(5), pp. 608-611 (2003).

Killday et al., "Microxine, a new cdc2 kinase inhibitor from the Australian marine sponge Microxina species," J. of Natural Products, vol. 64(4), pp. 525-526 (2001).

Lee et al., (2013), "Functional Role of mTORC2 versus Integrin-Linked Kinase in Mediating Ser473-Akt Phosphorylation in PTEN-Negative Prostate and Breast Cancer Cell Lines," PLOS ONE, Jun. 19, 2013, p. e67149, 8(6).

Mahesh et al. (2010). Intratracheally administered 5-azacytidine is effective against orthotopic human lung cancer xenograft models and devoid of important systemic toxicity. Clinical lung cancer, 11 (6), 405-11.

Meric-Bernstam et al., (2012), "PIK3CA/PTEN Mutations and Akt Activation As Markers of Sensitivity to Allosteric mTOR Inhibitors," Clinical Cancer Research, Mar. 14, 2012, pp. 1777-1789, 18(6).

Minehan et al., "Molecular recognition of DNA by Hoechst Benzimidazoles: Exploring beyond theopyrrole-imidazole-hydroxypyrrole polyamide-pairing code," Helvitica Chima Acta, vol. 83(9), pp. 2197-2213 (2000).

Mortensen et al., "Discovery and SAR exploration of a novel series of imidazo[4,5-] pyrazin-2-ones as potent and selective mTOR kinase inhibitors," Bioorganic & Medicinal Chemistry Letters, Pergamon, Elsevier Science, GB, vol. 21(22), pp. 6793-6799 (2011).

Nagashima et al., "Solution-Phase parallel synthesis of an N-Alkylated dihydropteridinone library from fluorous amino acids," J of Comb. Chemistry, vol. 6(6), pp. 942-949 (2004).

Nishino et al. (2010). New response evaluation criteria in solid tumors (RECIST) guidelines for advanced non-small cell lung cancer: comparison with original RECIST and impact on assessment of tumor response to targeted therapy. AJR. American journal. Registry File Document for RN 863501-03-5, 863502-39-0 (Sep. 20, 2005).

Office Action mailed Jun. 11, 2009 for U.S. Appl. No. 11/975,652.
Office Action mailed Sep. 2, 2009 for U.S. Appl. No. 11/975,652.
Final Office Action mailed Feb. 2, 2010 for U.S. Appl. No. 11/975,652 with Notice of References Cited.
Office Action mailed May 12, 2010 for U.S. Appl. No. 11/975,652.
Final Office Action mailed Sep. 30, 2010 for U.S. Appl. No. 11/975,652 with Notice of References Cited.
PCT International Search Report dated Mar. 29, 2010 issued in connection with PCT/US2009/062143.
PCT Written Opinion of the International Searching Authority dated Mar. 29, 2010 issued in connection with PCT/US2009/062143.
Office Action mailed Nov. 10, 2010 for U.S. Appl. No. 12/605,791.
PCT IPRP with Written Opinion of the International Searching Authority dated May 12, 2011 in connection with PCT /US2009/062143.
Office Action mailed Jan. 19, 2011 for U.S. Appl. No. 12/605,791 with Notice of References Cited.
Final Office Action mailed May 10, 2011 for U.S. Appl. No. 12/605,791.
Advisory Action mailed Aug. 17, 2011 for U.S. Appl. No. 12/605,791.
Advisory Action mailed Sep. 14, 2011 for U.S. Appl. No. 2/605,791.
PCT International Search Report dated Dec. 27, 2010 issued in connection with PCT/US2010/053678.
PCT Written Opinion dated Dec. 27, 2010 in connection with PCT/US/10/53678.
Office Action mailed Feb. 28, 2012 for U.S. Appl. No. 12/910,920 with Notice of Reference Cited.
PCT IPRP dated May 10, 2012 issued in connection with PCT/US2010/053678.
Office Action mailed Jun. 28, 2012 for U.S. Appl. No. 12/910,920 with Notice of Reference Cited.
Final Office Action mailed Nov. 6, 2012 for U.S. Appl. No. 12/910,920 with Notice of Reference Cited.
Office Action mailed Apr. 2, 2012 for U.S. Appl. No. 13/295,513.
Office Action mailed Aug. 27, 2012 for U.S. Appl. No. 13/295,513 with Notice of References Cited.
PCT Partial International Search dated Feb. 21, 2013 issued in connection with PCT/US2012/060723.
PCT International Search Report dated Feb. 13, 2013 issued in connection with PCT/US2012/067172.
PCT Written Opinion dated Feb. 13, 2013 issued in connection with PCT/US/2012/067172.
PCT Partial International Search dated Nov. 15, 2012 issued in connection with PCT/US2012/049281.
PCT International Search Report dated Jan. 11, 2013 issued in connection with PCT/US2012/049281.
PCT Written Opinion dated Feb. 13, 2013 issued in connection with PCT/US2012/049281.
PCT Invitation to Pay Additional Fees and, Where Applicable, Protest Fee dated Dec. 18, 2014 issued in connection with PCT/US2014/059043.
Papadimitrakopoulou et al., "A phase 1 / 2 study investigating the combination of RAD001® (everolimus) and erlotinib (E) as $2^{nd}$ and $3^{rd}$ line therapy in patients (pts) with advanced non-small cell lung cancer (NSCLC) previously treated with chemotherapy (C): Phase 1 results," Journal of Clinical Oncology, ASCO Annual Meeting Proceedings (Post-Meeting Edition), vol. 26, No. 15S, p. 8051 (2008).

(56) References Cited

OTHER PUBLICATIONS

Park et al., "A novel mechanism of TRAF signaling revealed by structural and functional analyses of the TRADD-TRAF2 interaction," Cell, vol. 101, pp. 777-787 (2000).
Patani et al., "Bioisosterim: A rational approach in drug design," Chemical Reviews, vol. 96, pp. 3147-3176 (1996).
Perez-Soler et al. (2004). Determinants of tumor response and survival with erlotinib in patients with non-small-cell lung cancer, Journal of Clinical Oncology, 22(16), 3238-3247.
Seela et al., "Product Class 17: Purines," Science of Synthesis, vol. 16, pp. 945-1108 (2004).
Shaw et al., "The LKB1 tumor suppressor negatively regulates mTOR signaling," Cancer Cell, vol. 6(1), pp. 91-99 (2004).
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Sridhar et al., "Protein Kinasesas Therapeutic Targets," Pharm. Research, vol. 17(11), pp. 1345-1353 (2000).
Vippagunta et al., 2001, "Crystalline solids." *Adv. Drug. Deliv. Rev.*, 48(1):3-26 (Cited in Office Action in connection with U.S. Appl. No. 12/605,791).
Wallace, "Palladium-catalyzed synthesis of quinoxaline derivatives," Tetrahedron, vol. 64, pp. 9675-9684 (2008).
Wallin et al., (2011), "GDC-0980 Is a Novel Class I PI3K/mTOR Kinase Inhibitor with Robust Activity in Cancer Models Driven by the PI3K Pathway," Molecular Cancer Therapeutics, Dec. 1, 2011, pp. 2426-2436, 10(12), American Association of Cancer Research, US.
Weigelt et al., (2011), "PIK3CA mutation, but not PTEN loss of function, determines the sensitivity of breast cancer cells to mTOR inhibitory drugs," ONCOGENE, Jul. 21, 2011, pp. 3222-3233, 30(29).
Westover et al., "Synthesis and antiviral activity of certain 9-β-D-Riofuranoaylpurine-6-carboxamides," J.Med. Chem., vol. 24(8), pp. 941-946 (1981).
Wheler et al., (2014), "Anastrozole and everolimus in advanced gynecologic and breast malignancies: activity and molecular alterations in the PI3K/AKT/mTOR pathway," Oncotarget, May 30, 2014, p. 3029.
Wingo et al., "Somatic LKB1 Mutations Promote Cervical Cancer Progression," PLOS ONE, vol. 4(4), pp. 5137-5138 (2009).
Wolff, Manfred E., Ed. Burger's Medicinal Chemistry and Drug Discovery—Fifth Edition, New York: John Wiley & Sons, vol. 1, pp. 975-976 (1996).
Xiang et al., (2011), "Targeting the Akt/mTOR pathway in Brca1-deficient cancers," ONCOGENE, May 26, 2011, pp. 2443-2450, 30(21).
Yoneda et al., "Synthesis of imadazo[4,5-e]-as-triazine (6-Azapurine) Deriviatives," Chem & Pharm Bulletin, vol. 26(10), pp. 3154-3160 (1978).
Yoneda et al., "A transformation of 7-azapteridines into 6-azapurines (Imidazo[4,5-e]-as-triazines)," Heterocycles, vol. 4(9), pp. 1503-1508 (1976).
Yuan et al., "Targeting tumorigenesis: development and use of mTOR inhibitors in cancer therapy," Journal of Hematology & Oncology, vol. 2(1), p. 45 (2009).
Zaki et al., "The synthesis of imidazol[4,5-*d*]pyridines from a substituted imidazole and acyl or sulfonyl acetonitrile," Tetrahedron, vol. 63(18), pp. 3745-3753 (2007).

\* cited by examiner

========================================
Area Percent Report
========================================

Sorted By       :    Signal
Multiplier      :    1.0000
Dilution        :    1.0000
Use Multiplier & Dilution Factor with ISTDs Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 6.065 | BB | 0.0645 | 8.98605 | 1.96075 | 0.1232 |
| 2 | 7.254 | BB | 0.0628 | 20.63753 | 4.64911 | 0.2830 |
| 3 | 7.986 | BV | 0.0516 | 37.09024 | 10.93555 | 0.5087 |
| 4 | 8.108 | VB | 0.0666 | 7211.97217 | 1541.72583 | 98.9116 |
| 5 | 8.746 | BB | 0.0676 | 12.64703 | 2.65360 | 0.1735 |

Totals:                              7291.33302   1561.92483

```
===========================================
             Area Percent Report
===========================================
Sorted By        :    Signal
Multiplier       :    1.0000
Dilution         :    1.0000
Use Multiplier & Dilution Factor with ISTDs
```

Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 6.056 | BB | 0.0640 | 5.62753 | 1.26184 | 0.0848 |
| 2 | 8.108 | VB | 0.0665 | 6630.58594 | 1419.12451 | 99.9152 |
| Totals: | | | | 6636.21347 | 1420.38635 | |

```
=========================================
              Area Percent Report
=========================================
Sorted By         :    Signal
Multiplier        :    1.0000
Dilution          :    1.0000
Use Multiplier & Dilution Factor with ISTDs
```

Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 6.063 | BB | 0.0644 | 10.93240 | 2.38965 | 0.1320 |
| 2 | 7.252 | BB | 0.0625 | 13.43284 | 3.04458 | 0.1622 |
| 3 | 7.983 | BV | 0.0504 | 17.11532 | 5.19358 | 0.2067 |
| 4 | 8.106 | VB | 0.0655 | 8238.19531 | 1762.49817 | 99.4990 |
| Totals: | | | | 8279.67587 | 1773.12598 | |

```
=========================================
          Area Percent Report
=========================================
Sorted By        :   Signal
Multiplier       :   1.0000
Dilution         :   1.0000
Use Multiplier & Dilution Factor with ISTDs
```

Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 4.063 | BB | 0.0566 | 30.11288 | 7.53175 | 0.2209 |
| 2 | 6.054 | BB | 0.0632 | 22.24025 | 5.07082 | 0.1632 |
| 3 | 7.983 | BV | 0.0504 | 27.15599 | 8.24914 | 0.1992 |
| 4 | 8.107 | VB | 0.0674 | 1.35412e4 | 2851.49048 | 99.3540 |
| 5 | 11.334 | BB | 0.0798 | 8.53068 | 1.49057 | 0.0626 |

Totals:  1.36292e4  2873.83277

```
=========================================
              Area Percent Report
=========================================

Sorted By       :    Signal
Multiplier      :    1.0000
Dilution        :    1.0000
Use Multiplier & Dilution Factor with ISTDs
```

Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 4.063 | BB | 0.0550 | 7.56031 | 1.91633 | 0.1334 |
| 2 | 6.058 | BB | 0.0620 | 117.23285 | 27.36800 | 2.0682 |
| 3 | 7.984 | BV | 0.0518 | 35.62207 | 10.44982 | 0.6284 |
| 4 | 8.107 | VB | 0.0666 | 5472.91162 | 1169.04773 | 96.5513 |
| 5 | 11.336 | BB | 0.0830 | 35.07249 | 5.92924 | 0.6187 |
| Totals: | | | | 5668.39934 | 1214.71114 | |

=========================================
            Area Percent Report
=========================================

Sorted By       :   Signal
Multiplier      :   1.0000
Dilution        :   1.0000
Use Multiplier & Dilution Factor with ISTDs Signal 1: DAD1 C, Sig=220, 4 Ref=off

| Peak # | RetTime [min] | Type | Width [min] | Area [mAU*s] | Height [mAU] | Area % |
|---|---|---|---|---|---|---|
| 1 | 6.054 | BB | 0.0644 | 21.15170 | 4.70971 | 0.3758 |
| 2 | 7.983 | BV | 0.0520 | 45.93118 | 13.40563 | 0.8160 |
| 3 | 8.106 | VB | 0.0656 | 5535.60352 | 1182.03992 | 98.3471 |
| 4 | 10.129 | BB | 0.1045 | 25.95539 | 3.58319 | 0.4611 |

Totals:                                5628.64178  1203.73844

```
=========================================
            Area Percent Report
=========================================

Sorted By       :   Signal
Multiplier      :   1.0000
Dilution        :   1.0000
Use Multiplier & Dilution Factor with ISTDs Signal 1: DAD1 C, Sig=220, 4 Ref=off
```

| Peak # | RetTime [min] | Type | Width [min] | Area [mAU*s] | Height [mAU] | Area % |
|---|---|---|---|---|---|---|
| 1 | 6.057 | BB | 0.0623 | 400.66650 | 92.88062 | 9.6019 |
| 2 | 7.983 | BV | 0.0533 | 131.68370 | 37.16783 | 3.1558 |
| 3 | 8.106 | VB | 0.0671 | 3640.44922 | 770.21002 | 87.2424 |
| Totals: | | | | 4172.79942 | 900.25847 | |

SOLID FORMS COMPRISING 7-(6-(2-HYDROXYPROPAN-2-YL) PYRIDIN-3-YL)-1-((TRANS)-4-METHOXYCYCLOHEXYL)-3,4-DIHYDROPYRAZINO[2,3-B]PYRAZIN-2(1H)-ONE, AND A COFORMER, COMPOSITIONS AND METHODS OF USE THEREOF

This application claims the benefit of U.S. Provisional Application No. 61/980,114, filed Apr. 16, 2014, the entire contents of which are incorporated herein by reference.

1. FIELD

Provided herein are solid forms comprising 7-(6-(2-hydroxypropan-2-yl)pyridin-3-yl)-1-((trans)-4-methoxycyclohexyl)-3,4-dihydropyrazino[2,3-b]pyrazin-2(1H)-one and a coformer. Pharmaceutical compositions comprising such solid forms (e.g., cocrystals) and methods of use for treating, preventing, and managing various disorders are also provided herein.

2. BACKGROUND

The identification and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see e.g., S. R. Byrn et al., Solid State Chemistry of Drugs, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (see e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, cocrystals and clathrates, among others (see e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

Notably, it is not possible to predict a priori if crystalline forms of a compound even exist, let alone how to successfully prepare them (see e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

Cocrystals are crystalline molecular complexes of two or more non-volatile compounds bound together in a crystal lattice by non-ionic interactions. Pharmaceutical cocrystals are cocrystals of a therapeutic compound, e.g., an active pharmaceutical ingredient (API), and one or more non-volatile compound(s) (referred to herein as coformer). A coformer in a pharmaceutical cocrystal is typically selected from non-toxic pharmaceutically acceptable molecules, such as, for example, food additives, preservatives, pharmaceutical excipients, or other APIs. In recent years, pharmaceutical cocrystals have emerged as a possible alternative approach to enhance physicochemical properties of drug products. The variety of possible solid forms creates potential diversity in physical and chemical properties for a given pharmaceutical compound.

The compound chemically named 7-(6-(2-hydroxypropan-2-yl)pyridin-3-yl)-1-((trans)-4-methoxycyclohexyl)-3,4-dihydropyrazino[2,3-b]pyrazin-2(1H)-one and tautomers thereof (collectively referred to herein as "Compound 1") are disclosed in U.S. Pat. No. 8,110,578, issued on Feb. 7, 2012, and International Pub. No. WO 2010/062571, the entireties of each of which are incorporated by reference herein.

Citation or identification of any reference in Section 2 of this application is not to be construed as an admission that the reference is prior art to the present application.

3. SUMMARY

Provided herein are solid forms (e.g., cocrystal forms or mixtures thereof) comprising the Compound of formula 1:

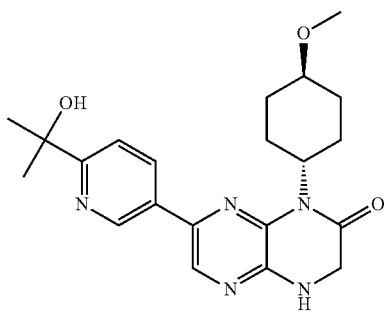

having the name 7-(6-(2-hydroxypropan-2-yl)pyridin-3-yl)-1-((trans)-4-methoxycyclohexyl)-3,4-dihydropyrazino[2,3-b]pyrazin-2(1H)-one, including tautomers thereof, and a coformer. Also provided are methods of preparing, isolating, and characterizing the solid forms.

Also provided herein are pharmaceutical compositions and single unit dosage forms, which comprise one or more solid forms provided herein.

A solid form is provided which comprises (a) 7-(6-(2-hydroxypropan-2-yl)pyridin-3-yl)-1-((trans)-4-methoxycyclohexyl)-3,4-dihydropyrazino[2,3-b]pyrazin-2(1H)-one; and (b) a coformer. The coformer is fumaric acid, benzoic acid, gentisic acid or maleic acid. The solid form is substantially crystalline. The solid form can substantially be a cocrystal. The solid form is greater than 80% by weight, greater than 90% by weight, greater than 95% by weight, greater than 97% by weight, or greater than 99% by weight of a cocrystal. The solid form can be substantially physically pure. The solid form can be substantially free of other solid forms of 7-(6-(2-hydroxypropan-2-yl)pyridin-3-yl)-1-((trans)-4-methoxycyclohexyl)-3,4-dihydropyrazino[2,3-b]pyrazin-2(1H)-one. The solid form can further comprise amorphous 7-(6-(2-hydroxypropan-2-yl)pyridin-3-yl)-1-((trans)-4-methoxycyclohexyl)-3,4-dihydropyrazino[2,3-b]pyrazin-2(1H)-one. The solid form can be stable. The solid form can be substantially crystalline and thermally stable.

Also provided is a pharmaceutical composition comprising the solid forms provided herein. The pharmaceutical composition can further comprise a pharmaceutically acceptable excipient or carrier. The pharmaceutical composition can be a single unit dosage form. The pharmaceutical composition can be a tablet or a capsule.

Further provided herein are crystal forms comprising the compound of formula (I):

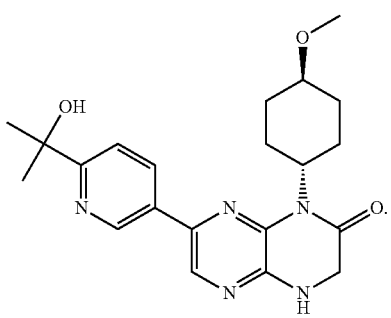

One crystal form has characteristic X-ray powder diffraction peaks at a two-theta angle of approximately 7.14, 11.42 and 22.7 degrees. The X-ray powder diffraction pattern can further comprise characteristic X-ray powder diffraction peaks at a two-theta angle of approximately 12.82, 16.1 and 25.5 degrees. The crystal form can further have a thermogravimetric analysis thermogram comprising no significant mass loss of the total mass of the crystal form between approximately 25° C. to approximately 100° C. when heated from approximately 25° C. to approximately 300° C. The crystal form can further have a single differential thermal analysis thermogram comprising an endotherm with a maximum at approximately 187.6° C. when heated from approximately 25° C. to approximately 300° C. The crystal form can be anhydrous. The crystal form can be is substantially pure.

Another crystal form has characteristic X-ray powder diffraction peaks at a two-theta angle of approximately 7.42, 18.3 and 23.82 degrees. The X-ray powder diffraction pattern can further comprise characteristic X-ray powder diffraction peaks at a two-theta angle of approximately 10.38, 15.94 and 19.42 degrees. The crystal form can have a thermogravimetric analysis thermogram comprising a total mass loss of approximately 1.12% of the total mass of the crystal form between approximately 35° C. and approximately 175° C. when heated from approximately 25° C. to approximately 300° C. The crystal form can have a single differential thermal analysis thermogram comprising an endotherm with a maximum at approximately 193.5° C. when heated from approximately 25° C. to approximately 300° C. The crystal form can be water solvated. The crystal form can be a monohydrate. The crystal form can be substantially pure.

Still another crystal form has characteristic X-ray powder diffraction peaks at a two-theta angle of approximately 7.3, 12.78 and 21.9 degrees. The X-ray powder diffraction pattern can further comprise characteristic X-ray powder diffraction peaks at a two-theta angle of approximately 11.86, 16.9 and 18.74 degrees. The crystal form can have a thermogravimetric analysis thermogram comprising a total mass loss of approximately 5% of the total mass of the crystal form between approximately 25° C. and approximately 100° C. when heated from about 25° C. to about 300° C. The crystal form can have a single differential thermal analysis thermogram comprising an endotherm with a maximum at approximately 67.7° C. when heated from about 25° C. to about 300° C. The single differential thermal analysis thermogram can further comprise an endotherm with a maximum at approximately 108° C. The single differential thermal analysis thermogram can further comprise an endotherm with a maximum at approximately 158° C. The crystal form can be water solvated. The crystal form can be substantially pure.

Another further crystal form has characteristic X-ray powder diffraction peaks at a two-theta angle of approximately 8.02, 13.82 and 25.02 degrees. The X-ray powder diffraction pattern can further comprise characteristic X-ray powder diffraction peaks at a two-theta angle of approximately 15.58, 19.82 and 21.02 degrees. The crystal form can have a thermogravimetric analysis thermogram comprising a total mass loss of approximately 1.7% of the total mass of the crystal form between approximately 35° C. and approximately 110° C. when heated from about 25° C. to about 300° C. The crystal form can have a single differential thermal analysis thermogram comprising an endotherm with a maximum at approximately 83.2° C. when heated from about 25° C. to about 300° C. The crystal form can be acetone solvated. The crystal form can be substantially pure.

Furthermore provided is a crystal form which has characteristic X-ray powder diffraction peaks at a two-theta angle of approximately 4.1, 15.78 and 25.78 degrees. The X-ray powder diffraction pattern can further comprise characteristic X-ray powder diffraction peaks at a two-theta angle of approximately 6.34, 8.3 and 20.06 degrees. The crystal form can have a thermogravimetric analysis thermogram comprising a total mass loss of approximately 4.6% of the total mass of the crystal form between approximately 25° C. and approximately 120° C. when heated from about 25° C. to about 300° C. The crystal form can have a single differential thermal analysis thermogram comprising an endotherm with a maximum at approximately 95.5° C. when heated from about 25° C. to about 300° C. The crystal form can be acetone solvated or water solvated. The crystal form can be substantially pure.

Still furthermore, provided is a crystal form which has characteristic X-ray powder diffraction peaks at a two-theta angle of approximately 4.26, 17.78 and 25.82 degrees. The X-ray powder diffraction pattern can further comprise characteristic X-ray powder diffraction peaks at a two-theta angle of approximately 13.02, 13.5 and 21.7±0.2° 2θ. The crystal form can have a thermogravimetric analysis thermogram comprising a total mass loss of approximately 0.9% of the total mass of the crystal form between about 70° C. and about 160° C. when heated from about 25° C. to about 300° C. The crystal form can have a single differential thermal analysis thermogram comprising an endotherm with a maximum at approximately 148° C. when heated from about 25° C. to about 300° C. The crystal form can be acetonitrile solvated. The crystal form can be substantially pure.

A further crystal form provided herein has characteristic X-ray powder diffraction peaks at a two-theta angle of approximately 6.54, 13.66, 26.02 degrees. The X-ray powder diffraction pattern can further comprise characteristic X-ray powder diffraction peaks at a two-theta angle of approximately 9.42, 18.42 and 26.82 degrees. The crystal form can have a thermogravimetric analysis thermogram comprising a total mass loss of approximately 4% of the total mass of the crystal form between approximately 35° C. and approximately 110° C. when heated from about 25° C. to about 300° C. The crystal form can have a single differential thermal analysis thermogram comprising an endotherm with a maximum at approximately 86° C. when heated from about 25° C. to about 300° C. The crystal form can be acetonitrile solvated or water solvated. The crystal form can be substantially pure.

Another further crystal form provided herein has characteristic X-ray powder diffraction peaks at a two-theta angle of approximately 6.14, 17.3 and 26.78 degrees. The X-ray powder diffraction pattern can further comprise characteristic X-ray powder diffraction peaks at a two-theta angle of approximately 7.42, 18.46 and 28.38 degrees. The crystal form can have a thermogravimetric analysis thermogram comprising a total mass loss of approximately 1% of the total mass of the crystal form between about 35° C. and about 110° C. when heated from about 25° C. to about 300° C. The crystal form can have a single differential thermal analysis thermogram comprising an endotherm with a maximum at approximately 118.8° C. when heated from about 25° C. to about 300° C. The crystal form can be ethyl acetate solvated. The crystal form can be substantially pure.

All the solid forms and the pharmaceutical compositions provided herein can be used as a medicament. In certain embodiments, solid forms of Compound 1 are useful for treating or preventing cancer and conditions treatable or preventable by inhibition of a kinase pathway, for example, the mTOR/PI3K/Akt pathway. All the solid forms and the pharmaceutical compositions can be used in methods for treating or preventing cancer, an inflammatory condition, an immunological condition, a neurodegenerative disease, diabete, obesity, a neurological disorder, an age-related disease, a cardiovascular condition, or a conditions treatable or preventable by inhibition of a kinase pathway. The methods comprise administering an effective amount of a solid form or a pharmaceutical composition to a subject in need thereof. The kinase pathway is the TOR kinase pathway.

All the solid forms and the pharmaceutical compositions can be used in methods for achieving a Response Evaluation Criteria in Solid Tumors (RECIST 1.1) of complete response, partial response or stable disease in a subject. The methods comprise administering an effective amount of a solid form or a pharmaceutical composition to a subject having a solid tumor.

All the solid forms and the pharmaceutical compositions can be used in methods for improving International Workshop Criteria (IWC) for NHL, International Uniform Response Criteria for Multiple Myeloma (IURC), Eastern Cooperative Oncology Group Performance Status (ECOG) or Response Assessment for Neuro-Oncology (RANO) Working Group for GBM. The methods comprise administering an effective amount of a solid form or a pharmaceutical composition to a subject in need thereof.

The present embodiments can be understood more fully by reference to the detailed description and examples, which are intended to exemplify non-limiting embodiments.

4. BRIEF DESCRIPTION OF THE DRAWINGS

5. DETAILED DESCRIPTION

5.1 Definitions

Figure 1:
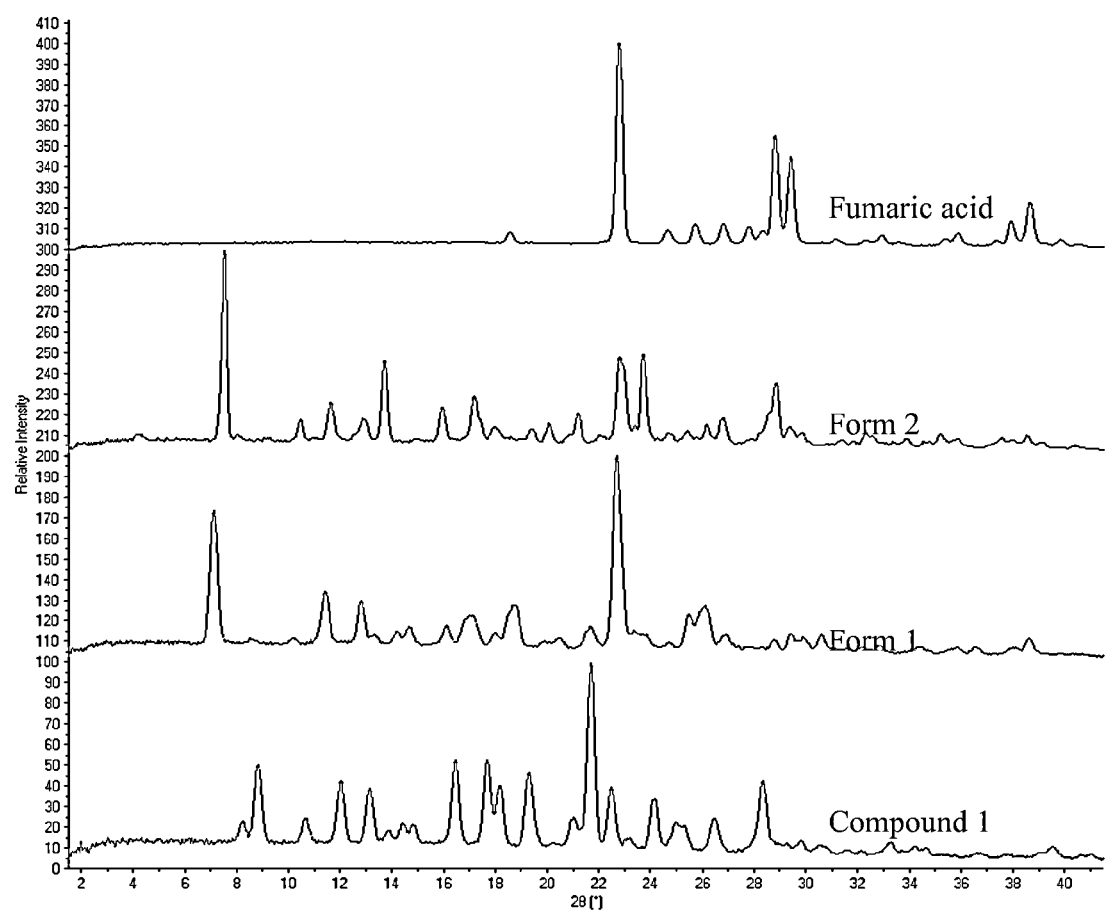
FIG. 1 depicts an X-ray powder diffractogram stack plot of Compound 1, Form 1, Form 2 and fumaric acid.

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2 degrees two theta while still describing the particular XRPD peak.

As used herein, and unless otherwise specified, a crystalline that is "pure," i.e., substantially free of other crystalline or amorphous forms, contains less than about 10% by weight of one or more other crystalline or amorphous forms, less than about 5% by weight of one or more other crystalline or amorphous forms, less than about 3% by weight of one or more other crystalline or amorphous forms, or less than about 1% by weight of one or more other crystalline or amorphous forms.

As used herein and unless otherwise indicated, the term "substantially pure" when used to describe a polymorph of a compound, i.e. a crystal form or an amorphous form of a compound, means a crystal form or an amourphous form of the compound that comprises that crystal form or amorphous form and is substantially free of other polymorphs of the compound. A substantially pure crystal form is no less than about 95% pure, no less than about 96% pure, no less than about 97% pure, no less than about 98% pure, no less than about 98.5% pure, no less than about 99% pure, no less than about 99.5% pure, or no less than about 99.8% pure. In certain embodiments, a form that is substantially pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other polymorphs on a weight basis.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

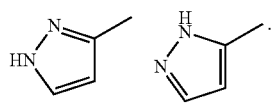

As readily understood by one skilled in the art, a wide variety of functional groups and other structures may exhibit tautomerism and all tautomers of Compound 1 are within the scope of the present invention.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

The term "solid form" refers to a physical form which is not predominantly in a liquid or a gaseous state. As used herein and unless otherwise specified, the term "solid form," when used herein to refer to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, the solid form of Compound 1 is Form 1, Form 2, Form 3, Form 4, Form 5, Form 6, Form 7, Form 8 or a mixture thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

The term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

Unless otherwise specified, the term "cocrystal" as used herein, refers to a crystalline material comprised of Compound 1, including tautomers thereof, and one or more non-volative compounds bound together in a crystal lattice by non-covalent interactions.

Unless otherwise specified, the term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

Unless otherwise specified, the terms "polymorph," "polymorphic form," "polymorphs," "polymorphic forms," and related terms herein refer to two or more crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

The term "subject" refers to an animal, including, but not limited to, a primate (e.g., human), cow, pig, sheep, goat, horse, dog, cat, rabbit, rat, or mouse. The terms "subject" and "patient" are used herein interchangeably in reference, for example, to a mammalian subject, such as a human subject, in one embodiment, a human. In one embodiment, the subject has or is susceptible to having a disease, disorder, or condition provided herein.

The term "treat," "treating," or "treatment" means an alleviation, in whole or in part, of a disease, disorder, or condition provided herein, or one or more symptoms associated with the disease, disorder, or condition, or slowing, or halting of further progression or worsening of the disease, disorder, or condition, or one or more symptoms associated with the disease, disorder, or condition.

The term "prevent," "preventing," or "prevention" means prevention of the onset, recurrence, or spread of a disease, disorder, or condition provided herein, or one or more symptoms associated with the disease, disorder, or condition, in a subject at risk for developing the disease, disorder, or condition.

The term "effective amount" or "therapeutically effective amount" refers to, in one embodiment, an amount of Compound 1 capable of alleviating, in whole or in part, one or more symptoms associated with a disease, disorder, or condition provided herein, or slowing or halting further progression or worsening of one or more of the symptoms of the disease, disorder, or condition; in another embodiment, an amount capable of preventing or providing prophylaxis for the disease, disorder, or condition in a subject at risk for developing the disease, disorder, or condition, such as cancer, inflammatory conditions, immunological conditions, neurodegenerative diseases, diabetes, obesity, neurological disorders, age-related diseases, and/or cardiovascular conditions, and/or diseases, disorders, and conditions treatable or preventable by inhibition of a kinase pathway, for example, the mTOR/PI3K/Akt pathway. In one embodiment, an effective amount of a compound is an amount that inhibits a kinase in a cell, such as, for example, in vitro or in vivo. In one embodiment the kinase is TOR kinase. In certain embodiments, the effective amount of a compound inhibits the kinase in a cell by about 10%, about 20%, about 30%, about 40%, about 50%, about 60%, about 70%, about 80%, about 90%, or about 99%, compared to the activity of the kinase in an untreated cell. In one embodiment, "effective amount" refers to the amount of Compound 1 capable of alleviating, in whole or in part, symptoms associated with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma, or slowing or halting further progression or worsening of those symptoms, or treating or preventing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma in a subject having or at risk for having a solid tumor, non-Hodgkin lymphoma or multiple myeloma. As will be apparent to those skilled in the art, it is to be expected that the effective amount of a compound disclosed herein may vary depending on the indication being treated, e.g., the effective amount of the compound would likely be different for treating patients suffering from, or at risk for, inflammatory conditions relative to the effective amount of the compound for treating patients suffering from, or at risk of, a different disorder, e.g., a disorder provided herein.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma, inhibition may be assessed by inhibition or retarding of disease progression, inhibition of tumor growth, reduction or regression of primary and/or secondary tumor (s), relief of tumor-related symptoms, improvement in quality of life, inhibition of tumor secreted factors (including tumor secreted hormones, such as those that contribute to carcinoid syndrome), reductions in endocrine hormone markers (for example, chromogranin, gastrin, serotonin, and/or glucagon), delayed appearance or recurrence of primary or secondary tumors, slowed development of primary and/or secondary tumors, decreased occurrence of primary and/or secondary tumors, slowed or decreased severity of secondary effects of disease, arrested tumor growth and/or regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma altogether or preventing the onset of a preclinically evident stage of a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma. Also intended to be encompassed by this definition is the prevention of transformation into malignant cells or to arrest or reverse the progression of premalignant cells to malignant cells. This includes prophylactic treatment of those at risk of developing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma, including advanced solid tumors), non-Hodgkin lymphoma or multiple myeloma.

An "advanced solid tumor" as used herein, means a solid tumor that has spread locally, or metastasized or spread to another part of the body.

In certain embodiments, the treatment may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
| --- | --- | --- | --- |
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative<br>(b) Variably FDG-avid or PET negative; regression to normal size on CT | Not palpable, nodules disappeared | Infiltrate cleared on repeat biopsy; if indeterminate by morphology, immunohisto-chemistry should be negative |
| PR | Regression of measurable disease and no new sites | ≥50% decrease in SPD of up to 6 largest dominant masses; no increase in size of other nodes<br>(a) FDG-avid or PET positive prior to therapy; one or more PET positive at previously involved site<br>(b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET<br>(b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [$^{18}$F]fluorodeoxyglucose; PET, positron emission tomography; CT, computed tomography; PR, partial remission; SPD, sum of the product of the diameters; SD, stable disease; PD, progressive disease.

| End point | Patients | Definition | Measured from |
| --- | --- | --- | --- |
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus |
| | Normal FLC ratio and |
| | Absence of clonal cells in bone marrow[b] by immunohistochemistry or immunofluorescence[c] |
| CR | Negative immunofixation on the serum and urine and |
| | Disappearance of any soft tissue plasmacytomas and |
| | <5% plasma cells in bone marrow[b] |
| VGPR | Serum and urine M-protein detectable by immunofixation but not on electrophoresis or 90% or greater reduction in serum M- |
| | protein plus urine M-protein level <100 mg per 24 h |
| PR | ≥50% reduction of serum M-protein and reduction in 24-h urinary M-protein by ≥90% or to <200 mg per 24 h |
| | If the serum and urine M-protein are unmeasurable, [d] a ≥50% decrease in the difference between involved and uninvolved FLC levels is required in place of the M-protein criteria |
| | If serum and urine M-protein are unmeasurable, and serum free |
| | light assay is also unmeasurable, ≥50% reduction in plasma cells is required in place of M-protein, provided baseline bone marrow plasma cell percentage was ≥30% |
| | In addition to the above listed criteria, if present at baseline, a ≥50% reduction in the size of soft tissue plasmacytomas is also |
| | required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;
[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis, and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

Unless otherwise specified, to the extent that there is a discrepancy between a depicted chemical structure of a compound provided herein and a chemical name of a compound provided herein, the chemical structure shall control.

5.2 Compound 1

The solid forms, formulations and methods of use provided herein relate to solid forms (e.g., cocrystals) of Compound 1:

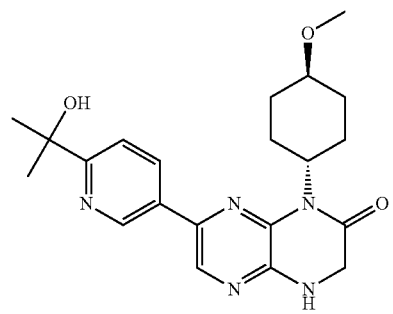

having the name 7-(6-(2-hydroxypropan-2-yl)pyridin-3-yl)-1-((trans)-4-methoxycyclohexyl)-3,4-dihydropyrazino[2,3-b]pyrazin-2(1H)-one, including tautomers thereof.

Compound 1 can be prepared using reagents and methods known in the art, including the methods provided in U.S. Pat. No. 8,110,578, issued on Feb. 7, 2012; US Patent Publication Application No. 2011/0137028, published on Jun. 9, 2011; and U.S. Provisional Patent Application No. 61/813,064, filed on Apr. 17, 2013, the entire contents of each of which are incorporated herein by reference.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Form Cocrystals of Compound 1

While not intending to be bound by any particular theory, certain solid form cocrystals are characterized by physical properties, e.g., stability, solubility and dissolution rate, appropriate for pharmaceutical and therapeutic dosage forms. Moreover, while not wishing to be bound by any particular theory, certain solid form cocrystals are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid form cocrystals suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

In one embodiment, provided herein are solid forms (e.g., crystal forms or mixtures thereof) comprising (a) Compound 1; and (b) a coformer. In one embodiment, provided herein are solid forms (e.g., crystal forms or mixtures thereof) comprising (a) a free base of Compound 1; and (b) a coformer. Compound 1 can be synthesized or obtained according to a method known in the literature or based upon the teachings herein, including the methods described in detail in the examples herein.

In certain embodiments, the coformer is fumaric acid, benzoic acid, gentisic acid, or maleic acid.

In one embodiment, provided herein is a cocrystal comprising (a) Compound 1; and (b) a coformer. In one embodiment, provided herein is a mixture comprising (i) a cocrystal comprising (a) Compound 1; and (b) a coformer; and (ii) a crystal form of Compound 1. In one embodiment, provided herein is a mixture comprising (i) a cocrystal comprising (a) Compound 1; and (b) a coformer; and (ii) an amorphous form of Compound 1.

In one embodiment, provided herein is a solid form comprising (a) Compound 1 and (b) a coformer that is substantially crystalline. In one embodiment, provided herein is a solid form comprising a cocrystal comprising (a) Compound 1 and (b) a coformer. In one embodiment, provided herein is a solid form comprising (i) a cocrystal comprising (a) Compound 1 and (b) a coformer and (ii) an amorphous form of Compound 1. In one embodiment, provided herein is a solid form comprising (i) a cocrystal comprising (a) Compound 1 and (b) a coformer and (ii) one or more additional crystal forms of Compound 1.

In one embodiment, provided herein is an unsolvated solid form comprising (a) Compound 1 and (b) a coformer. In one embodiment, provided herein is an anhydrous solid form comprising (a) Compound 1 and (b) a coformer. In one embodiment, provided herein is an unsolvated crystal form comprising (a) Compound 1 and (b) a coformer. In one embodiment, provided herein is an anhydrous crystal form comprising (a) Compound 1 and (b) a coformer. In one embodiment, provided herein is a solvated solid form comprising (a) Compound 1 and (b) a coformer. In one embodiment, provided herein is a hydrated solid form comprising (a) Compound 1 and (b) a coformer (e.g., a hydrate having a stoichiometric or non-stoichiometric amount of water). In one embodiment, provided herein is a hydrated form of (a) Compound 1 and (b) a coformer, including, but not limited to, a hemihydrate, a monohydrate, a dihydrate, a trihydrate, and the like. In one embodiment, the hydrated form is substantially crystalline. In one embodiment, the anhydrous form is substantially crystalline. In one embodiment, provided herein is an unsolvated cocrystal comprising (a) Compound 1 and (b) a coformer. In one embodiment, provided herein is an anhydrous cocrystal comprising (a) Compound 1 and (b) a coformer. In one embodiment, provided herein is a hydrated cocrystal comprising (a) Compound 1 and (b) a coformer. In one embodiment, provided herein is a solvated cocrystal comprising (a) Compound 1 and (b) a coformer.

Solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., cocrystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid. The particle size of the resulting solid forms, which can vary (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing, or sonication.

In some embodiments, the cocrystal comprising (a) Compound 1 and (b) a coformer can be obtained by crystallization from certain solvent systems, for example, solvent systems comprising one or more of the following solvents: ethanol, a mixture of ethanol and water (e.g., about 10/90 or about 50/50), a mixture of methanol and water (e.g., about 50/50), a mixture of THF and water (e.g., about 50/50), acetonitrile, ethyl acetate, a mixture of acetone and water (e.g., about 10/90), cyclohexane, p-xylene and water. In certain embodiments, a solid form provided herein (e.g., a cocrystal comprising (a) Compound 1 and (b) a coformer) can be obtained by cooling evaporation experiments, powder in saturated solutions experiments, slurry experiments, and grinding experiments.

In certain embodiments, the non-covalent forces are one or more hydrogen bonds (H-bonds). The coformer may be H-bonded directly to Compound 1 or may be H-bonded to an additional molecule which is bound to Compound 1. The additional molecule may be H-bonded to Compound 1 or bound ionically or covalently to Compound 1. The additional molecule could also be a different active or inactive ingredient. In certain embodiments, the cocrystals may include one or more solvate molecules in the crystalline lattice, i.e., solvates of cocrystals, or a cocrystal further comprising a solvent or compound that is a liquid at room temperature. In certain embodiments, the cocrystals may be a cocrystal between a coformer and a salt of Compound 1. In certain embodiments, the non-covalent forces are pi-stacking, guest-host complexation and/or van der Waals interactions. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

In certain embodiments, the coformer is a solid under ambient temperature conditions when in its pure form.

In certain embodiments, cocrystals can be prepared using solid-state methods such as solid-state grinding and solvent-drop grinding. In certain embodiments, cocrystals can be prepared using high-throughput screening. In certain embodiments cocrystals can be prepared using solution-based crystallization.

In certain embodiments, cocrystals formation can lead to enchancment of physical properties of the resulting solid forms, such as solubility, dissolution rate, bioavailablity, physical stability, chemical stability, flowability, fractability, or compressibility.

In certain embodiments, provided herein are cooling evaporative methods for making a solid form cocrystal of Compound 1, comprising 1) obtaining a close-to saturated solution of Compound 1 and conformers in a ratio (e.g., about 1:1.1 or about 1:1.4) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., 48 hours); 5) filtering the solution to yield a solid if there is precipitation; and 6) evaporating the solvent to collect a solid if there is no precipitation after step 4. In certain embodiments, provided herein are cooling evaporative methods for making a solid form cocrystal of Compound 1, comprising 1) obtaining a close-to saturated solution of Compound 1 and conformers in a solvent; 2) heating the solution to about 40° C.); 3) cooling the solution to about 2° C.); 4) keeping the solution at about 2° C. for about 48 hours; 5) filtering the solution to yield a solid if there is precipitation; and 6) evaporating the solvent to collect a solid if there is no precipitation after step 4. In certain embodiments, the solvent is ethanol, a mixture of ethanol and water (e.g., about 50/50), a mixture of methanol and water (e.g., about 50/50), a mixture of THF and water (e.g., about 50/50), acetonitrile or ethyl acetate. In one embodiment, the molar ratio of Compound 1 and the conformers in step 1 is about 1:1.1 or about 1:1.4.

In certain embodiments, provided herein are slurry experiments for making a solid form cocrystal of Compound 1, comprising 1) obtaining a slurry of Compound 1 and conformers in a ratio in a solvent; 2) stirring the slurry for a period of time; and 3) collecting a solid from the slurry by filtration (e.g., centrifuge filtration). In certain embodiments, the solvent is acetonitrile, a mixture of acetone and water (e.g., about 10/90), cyclohexane, p-xylene, water or a mixture of ethanol and water (e.g., about 10/90). In one embodiment, the molar ratio of Compound 1 and the conformers is about 1:1.1. In one embodiment, the period of time is about 3 days.

In certain embodiments, provided herein are powder in saturated solutions methods for making a solid form cocrystal of Compound 1, comprising 1) obtaining a close-to saturated solution of Compound 1 in a solvent; 2) adding conformers into the solution; 3) stirring the solution at ambient temperature for a period of time; 4) filtering the solution to yield a first solid; and 5) evaporating the solvent to collect a second solid. In certain embodiments, the solvent is ethanol, a mixture of ethanol and water (e.g., about 50/50), a mixture of methanol and water (e.g., about 50/50), a mixture of THF and water (e.g., about 50/50), acetonitrile or ethyl acetate. In one embodiment, the molar ratio of Compound 1 and the conformers is about 1:1. In one embodiment, the period of time is about 4 hours.

In certain embodiments, provided herein are grinding methods for making a solid form cocrystal of Compound 1, comprising 1) adding Compound 1, conformers and a solvent into a grinding machine; 2) shaking the container for a period of time at a particular frequency; and 3) collecting the resulting solid by filtration (e.g., centrifuge filtration). In certain embodiments, the solvent is acetonitrile, a mixture of acetone and water (e.g., about 10/90), cyclohexane, p-xylene, water, or a mixture of ethanol and water (e.g., about 10/90). In one embodiment, the molar ratio of Compound 1 and the conformers is about 1:1.1. In one embodiment, the period of time is about 1 hour. In one embodiment, the frequency is about 30 Hz.

The solid form cocrystals provided herein (e.g., Form 1, Form 2, Form 3, Form 4, Form 5, Form 6, Form 7 and Form 8) may be characterized using a number of methods known to a person having ordinary skill in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), spectroscopy (e.g., infrared, Raman, and solid-state nuclear magnetic resonance), single differential thermal analysis (SDTA), high performance liquid chromatography coupled with mass spectroscopy (HPLC-MS), thermogravimetrical analysis coupled with single differential thermal analysis (TGA-SDTA), and thermogravimetric analysis coupled with mass spectroscopy (TGA-MS). The particle size and size distribution of the solid form provided herein may be determined by conventional methods, such as laser light scattering technique.

The purity of the solid form cocrystals provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two theta (°2θ) (see United State Pharmacopoeia, page 2228 (2003)).

5.3.1 Cocrystal Form 1 Comprising Compound 1 and Fumaric Acid

Provided herein is cocrystal Form 1 comprising Compound 1 and fumaric acid. In one embodiment, provided herein is a solid form comprising Compound 1 and fumaric acid that is substantially crystalline. In one embodiment, provided herein is a solid form comprising a cocrystal comprising Compound 1 and fumaric acid. In one embodiment, provided herein is a solid form comprising (i) a cocrystal comprising Compound 1 and fumaric acid and (ii) an amorphous form of Compound 1. In one embodiment, provided herein is a solid form comprising (i) a cocrystal comprising Compound 1 and fumaric acid and (ii) one or more additional crystal forms of Compound 1. Provided herein are various embodiments, preparations, or modifications of a cocrystal comprising Compound 1 and fumaric acid.

In one embodiment, Form 1 is an anhydrous solid form comprising Compound 1 and fumaric acid. In another embodiment, Form 1 is crystalline. In one embodiment, Form 1 is a cocrystal solid form of Compound 1 and fumaric acid in a 1:1 stoichiometric ratio.

In certain embodiments, Form 1 is obtained by cooling evaporative experiments comprising 1) obtaining a close-to saturated solution of Compound 1 and fumaric acid in a ratio (e.g., about 1:1.1) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., about 48 hours); 5) filtering the solution to yield a solid if there is precipitation; and 6) evaporating the solvent to collect a solid if there is no precipitation after step 4. In certain embodiments, Form 1 is obtained by cooling evaporative experiments, comprising 1) obtaining a close-to saturated solution of Compound 1 and fumaric acid in a solvent; 2) heating the solution to about 40° C.); 3) cooling the solution to about 2° C.); 4) keeping the solution at about 2° C. for about 48 hours; 5) filtering the solution to yield a solid if there is precipitation; and 6) evaporating the solvent to collect a solid if there is no precipitation after step 4. In one embodiment, the solvent is ethyl acetate. In one embodiment, the molar ratio of Compound 1 and fumaric acid in step 1 is about 1:1.1.

In certain embodiments, a solid form provided herein, e.g., Form 1, is substantially crystalline, as indicated by, e.g., X-ray powder diffraction measurements. In one embodiment, Form 1 has an X-ray powder diffraction pattern substantially as shown in FIG. 1 (the second pattern from bottom). In one embodiment, Form 1 has one or more characteristic X-ray powder diffraction peaks at a two-theta angle of approximately 7.14, 11.42, 12.82, 14.66, 16.1, 22.7 or 25.5 degrees as depicted in FIG. 1. In another embodiment, Form 1 has one, two, three or four characteristic X-ray powder diffraction peaks at a two-theta angle of approximately 7.14, 11.42, 12.82 or 22.7 degrees. In another embodiment, Form 1 has one, two, three, four, five, six or seven characteristic X-ray powder diffraction peaks as set forth in Table 12.

Figure 2:
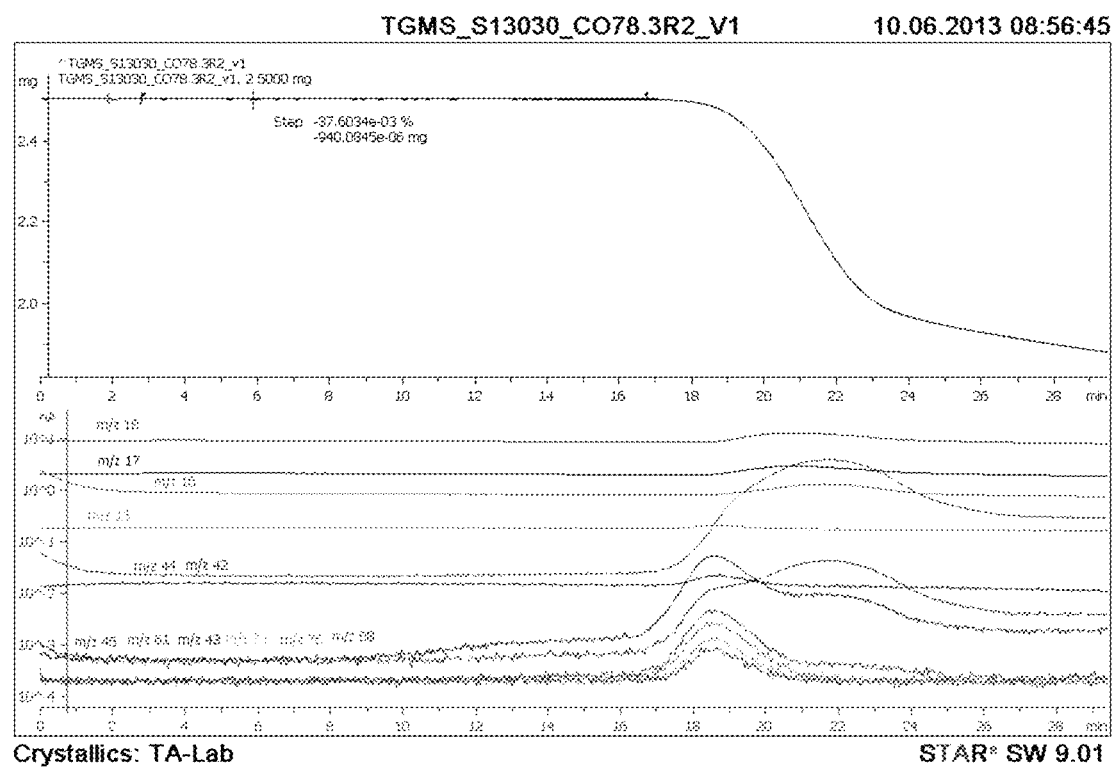
FIG. 2 depicts a thermogravimetric analysis coupled with mass spectroscopy of Form 1.

In one embodiment, provided herein is Form 1 having a thermogravimetric (TGA) thermograph corresponding substantially to the representative TGA thermogram as depicted in FIG. 2. In certain embodiments, the crystalline form exhibits a TGA thermogram comprising no significant mass of the sample between approximately 25° C. and approximately 100° C. when heated from approximately 25° C. to approximately 300° C. Thus, in certain embodiments, the crystalline form has no significant mass when heated from about ambient temperature to about 300° C.

Figure 3:
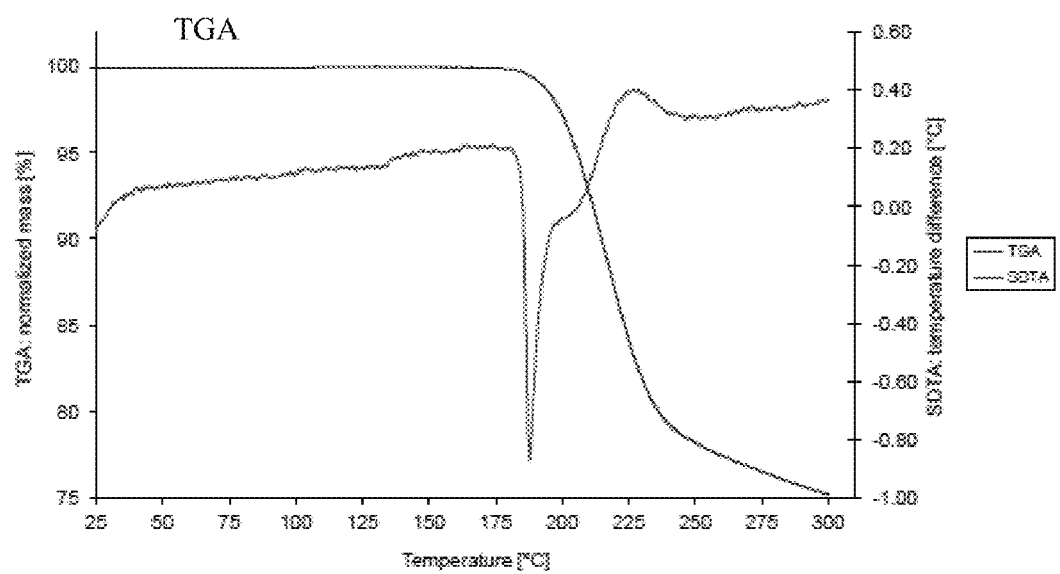
FIG. 3 depicts a thermogravimetrical analysis and single differential thermal analysis of Form 1.

In one embodiment, provided herein is Form 1 having a single differential thermal analysis (SDTA) thermogram as depicted in FIG. 3 comprising an endothermic event with a maximum at about 187.6° C., followed by immediate decomposition, when heated from approximately 25° C. to approximately 300° C.

In still another embodiment, Form 1 is substantially pure. In certain embodiments, the substantially pure Form 1 is substantially free of other solid forms, e.g., amorphous form. In certain embodiments, the purity of the substantially pure Form 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.2 Cocrystal Form 2 Comprising Compound 1 and Fumaric Acid

Provided herein is cocrystal Form 2 comprising Compound 1 and fumaric acid. In one embodiment, provided herein is a solid form comprising Compound 1 and fumaric acid that is substantially crystalline. In one embodiment, provided herein is a solid form comprising a cocrystal comprising Compound 1 and fumaric acid. In one embodiment, provided herein is a solid form comprising (i) a cocrystal comprising Compound 1 and fumaric acid and (ii) an amorphous form of Compound 1. In one embodiment, provided herein is a solid form comprising (i) a cocrystal comprising Compound 1 and fumaric acid and (ii) one or more additional crystal forms of Compound 1. Provided herein are various embodiments, preparations, or modifications of a cocrystal comprising Compound 1 and fumaric acid.

In one embodiment, Form 2 is a hydrated solid form comprising Compound 1 and fumaric acid. Form 2 is a mono-hydrate. In another embodiment, Form 2 is crystalline. In one embodiment, Form 2 is a cocrystal solid form of Compound 1 fumaric salt and fumaric acid in a 1:1 stoichiometric ratio.

In certain embodiments, Form 2 is obtained by cooling evaporative experiments comprising 1) obtaining a close-to saturated solution of Compound 1 and fumaric acid in a ratio (e.g., about 1:1.1) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., about 48 hours); 5) filtering the solution to yield a solid if there is precipitation; and 6) evaporating the solvent to collect a solid if there is no precipitation after step 4. In certain embodiments, Form 2 is obtained by cooling evaporative experiments, comprising 1) obtaining a close-to saturated solution of Compound 1 and fumaric acid in a solvent; 2) heating the solution to about 40° C.); 3) cooling the solution to about 2° C.); 4) keeping the solution at about 2° C. for about 48 hrs; 5) filtering the solution to yield a solid if there is precipitation; and 6) evaporating the solvent to collect a solid if there is no precipitation after step 4. In one embodiment, the solvent is a mixture of methanol and water (50/50). In one embodiment, the molar ratio of Compound 1 and fumaric acid in step 1 is about 1:1.4.

In certain embodiments, a solid form provided herein, e.g., Form 2, is substantially crystalline, as indicated by, e.g., X-ray powder diffraction measurements. In one embodiment, Form 2 has an X-ray powder diffraction pattern substantially as shown in FIG. 1 (the third pattern from bottom). In one embodiment, Form 2 has one or more characteristic X-ray powder diffraction peaks at a two-theta angle of approximately 7.42, 10.38, 13.7, 15.94, 17.9, 18.3, 19.42, 22.42, 23.38, 23.82, 25.46 or 26.78 degrees as depicted in FIG. 1. In a specific embodiment, Form 2 has one, two, three, four, five, six, seven or eight characteristic X-ray powder diffraction peaks at a two-theta angle of approximately 7.42, 10.38, 15.94, 17.9, 18.3, 19.42, 23.82 or 26.78 degrees. In another embodiment, Form 2 has one, two, three or four characteristic X-ray powder diffraction peaks at a two-theta angle of approximately 7.42, 15.94, 18.3 or 23.82 degrees. In another embodiment, Form 2 has one, two, three, four, five, six, seven, eight, nine, ten, eleven or twelve characteristic X-ray powder diffraction peaks as set forth in Table 13.

Figure 7:
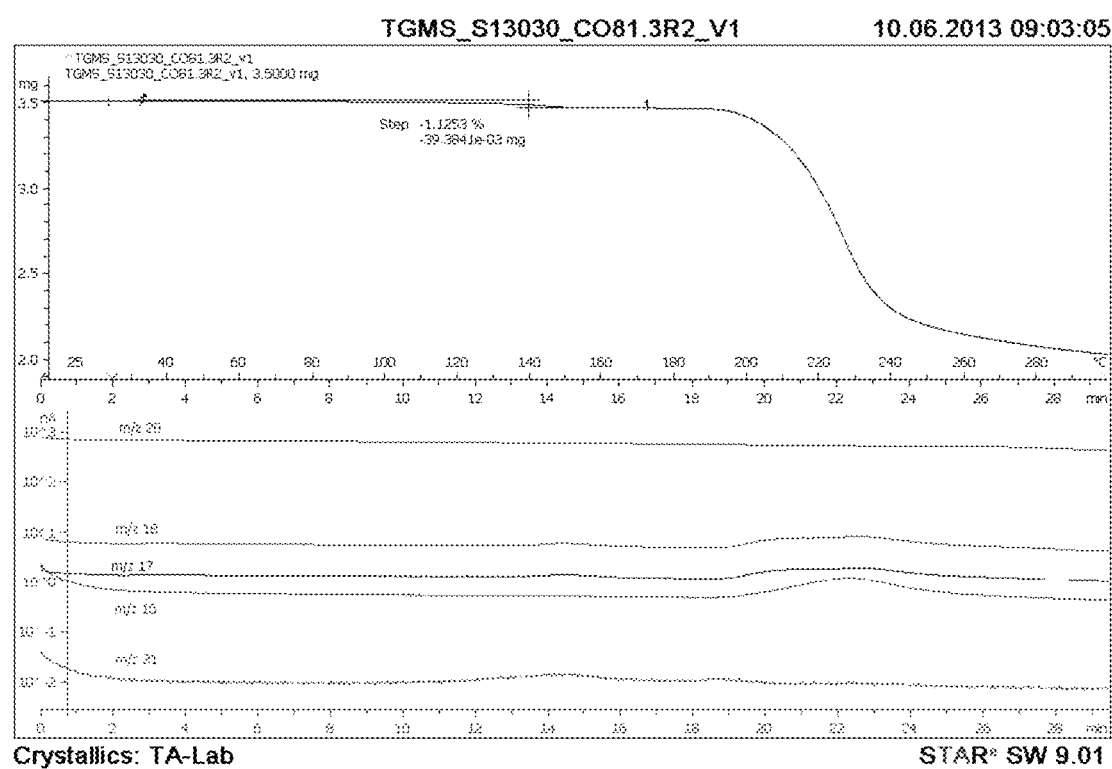
FIG. 7 depicts a thermogravimetric analysis coupled with mass spectroscopy of Form 2.

In one embodiment, provided herein is Form 2 having a thermogravimetric (TGA) thermograph corresponding substantially to the representative TGA thermogram as depicted in FIG. 7. In certain embodiments, the crystalline form exhibits a TGA thermogram comprising a total mass loss of approximately 1.12% of the total mass of the sample between approximately 35° C. and approximately 175° C. when heated from approximately 25° C. to approximately 300° C. Thus, in certain embodiments, the crystalline form loses about 1.12% of its total mass when heated from about ambient temperature to about 300° C.

Figure 8:
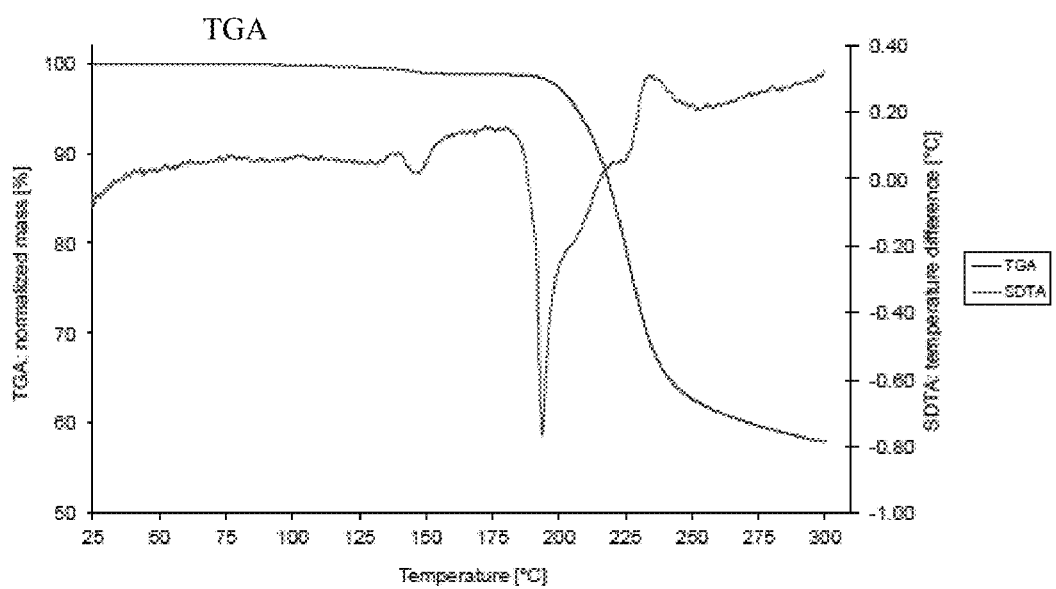
FIG. 8 depicts a thermogravimetrical analysis and single differential thermal analysis of Form 2.

In one embodiment, provided herein is Form 2 having a single differential thermal analysis (SDTA) thermogram as depicted in FIG. 8 comprising an endothermic event with a maximum at about 146° C., followed by an endothermic melt event at about 193.5° C. and then immediate decomposition, when heated from approximately 25° C. to approximately 300° C.

Figure 12:
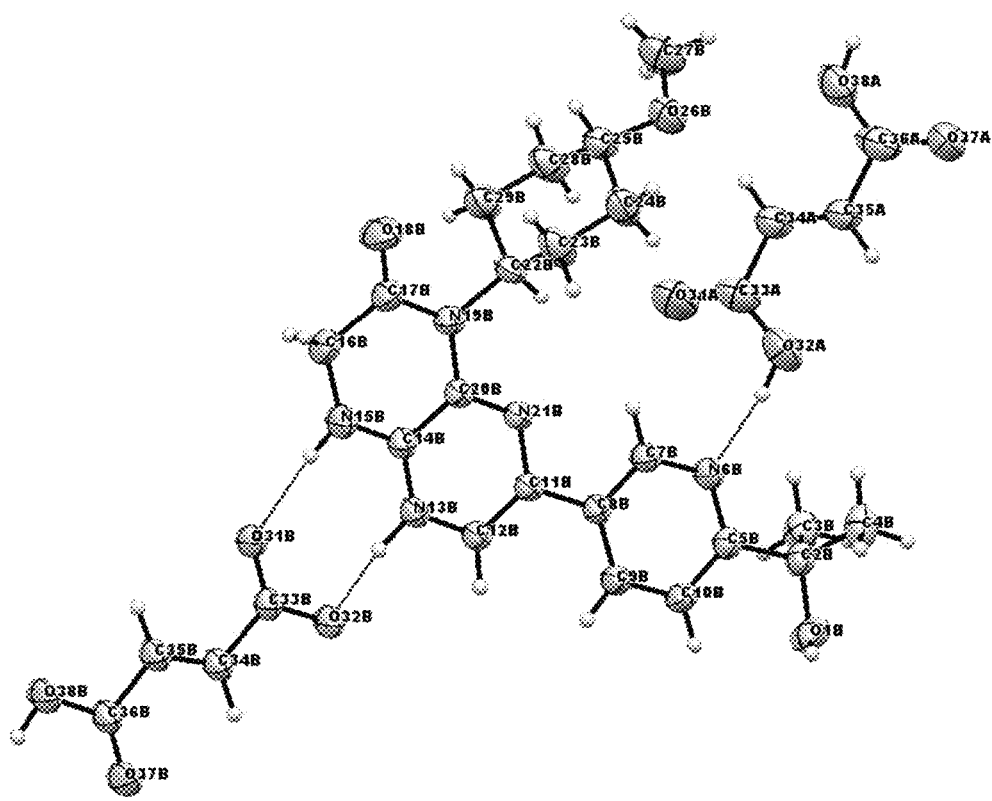
FIG. 12 depicts the molecular structure and atom numbering scheme for protonated Compound 1 and its chemical first co-ordination sphere in Form 2.
Figure 13:
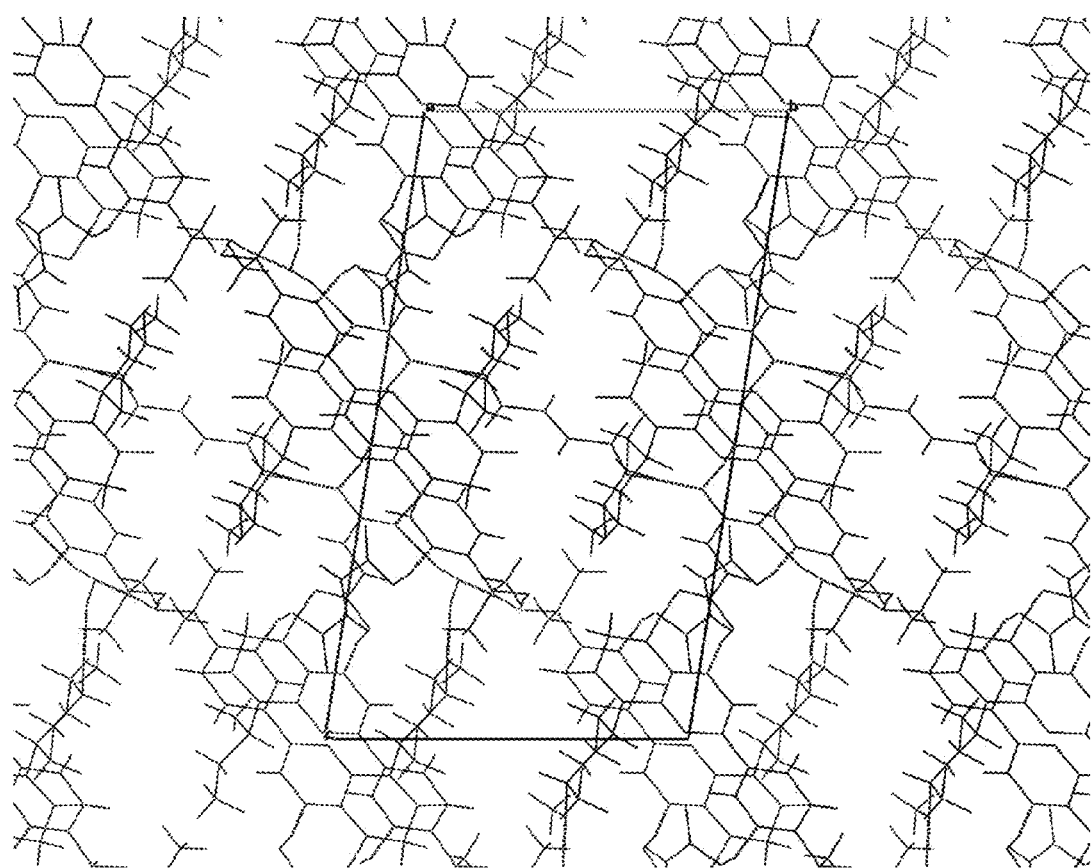
FIG. 13 depicts a crystal packing pattern and H-bond scheme of Form 2.

In one embodiment, a single-crystal X-ray diffraction analysis is employed to determine the crystal structure of Form 2 (see FIG. 12). Table 14 and Table 15 present a summary of the crystallographic data from the crystal-structure determination. In one embodiment, Form 2 has a crystal packing pattern substantially as shown in FIG. 13. In one embodiment, Form 2 is a hydrated solid form crystallizing in a triclinic symmetry with P-1 space group and having a Z equal to 2.

In still another embodiment, Form 2 is substantially pure. In certain embodiments, the substantially pure Form 2 is substantially free of other solid forms, e.g., amorphous form. In certain embodiments, the purity of the substantially pure Form 2 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.3 Cocrystal Form 3 Comprising Compound 1 and Benzoic Acid

Provided herein is cocrystal Form 3 comprising Compound 1 and benzoic acid. In one embodiment, provided herein is a solid form comprising Compound 1 and benzoic acid that is substantially crystalline. In one embodiment, provided herein is a solid form comprising a cocrystal comprising Compound 1 and benzoic acid. In one embodiment, provided herein is a solid form comprising (i) a cocrystal comprising Compound 1 and benzoic acid and (ii) an amorphous form of Compound 1. In one embodiment, provided herein is a solid form comprising (i) a cocrystal comprising Compound 1 and benzoic acid and (ii) one or more additional crystal forms of Compound 1. Provided herein are various embodiments, preparations, or modifications of a cocrystal comprising Compound 1 and benzoic acid.

In one embodiment, Form 3 is a hydrated solid form comprising Compound 1 and benzoic acid. In another embodiment, Form 3 is crystalline.

In certain embodiments, Form 3 is obtained by slurry experiments, comprising 1) obtaining a slurry of Compound 1 and benzoic acid in a ratio in a solvent; 2) stirring the slurry for a period of time; 3) collecting a solid from the slurry by filtration (e.g., centrifuge filtration). In one embodiment, the solvent is water. In one embodiment, the molar ratio of Compound 1 and benzoic acid is about 1:1.1. In one embodiment, the period of time is about 3 days.

Figure 15:
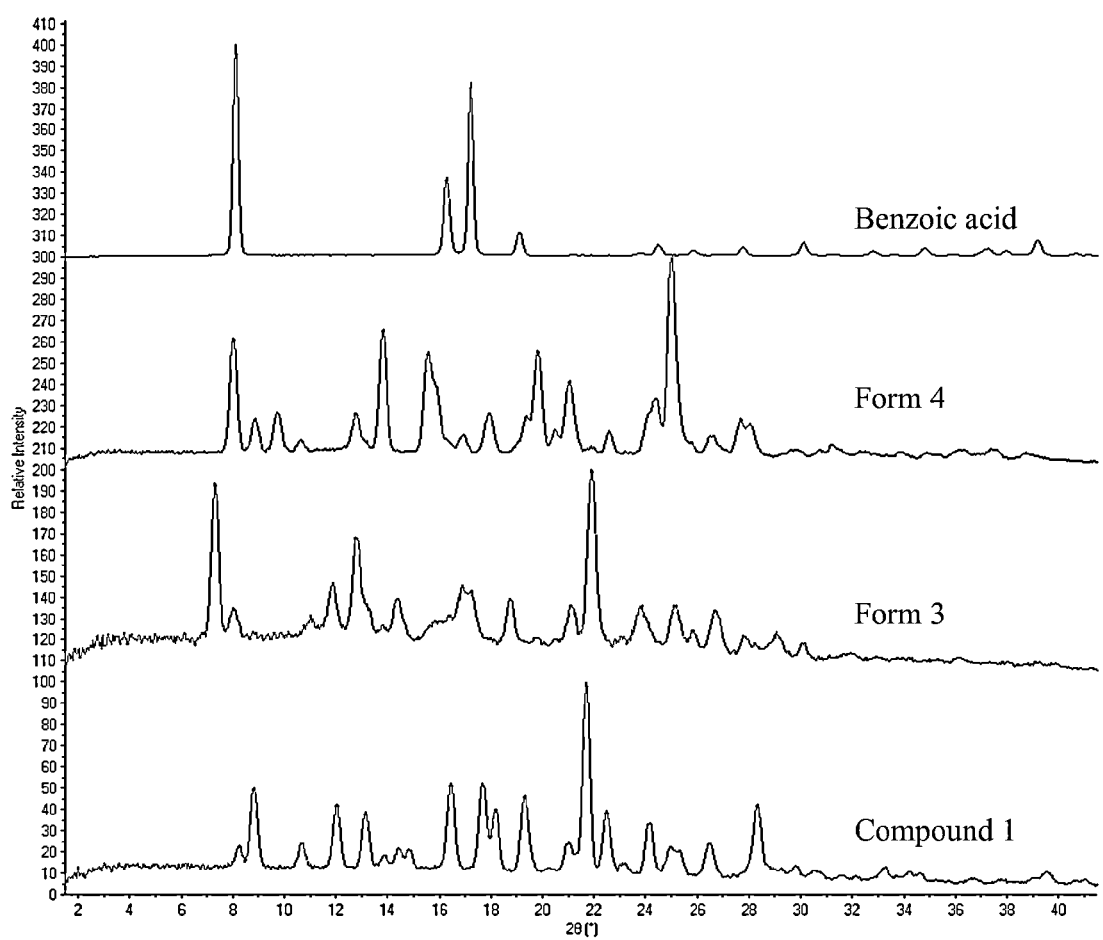
FIG. 15 depicts an X-ray powder diffractogram stack plot of Compound 1, Form 3, Form 4 and benzoic acid.

In certain embodiments, a solid form provided herein, e.g., Form 3, is substantially crystalline, as indicated by, e.g., X-ray powder diffraction measurements. In one embodiment, Form 3 has an X-ray powder diffraction pattern substantially as shown in FIG. 15 (the second pattern from bottom). In one embodiment, Form 3 has one or more characteristic X-ray powder diffraction peaks at a two-theta angle of approximately 7.3, 8.02, 11.86, 12.78, 14.38, 16.9, 18.74, 21.14, 21.9, 23.78, 25.14, 25.82 or 26.74 degrees as depicted in FIG. 15 (the second pattern from bottom). In a specific embodiment, Form 3 has one, two, three, four, five, six, seven or eight characteristic X-ray powder diffraction peaks at a two-theta angle of approximately 7.3, 11.86, 12.78, 16.9, 18.74, 21.9, 25.14 or 26.74 degrees. In another embodiment, Form 3 has one, two, three or four characteristic X-ray powder diffraction peaks at a two-theta angle of approximately 7.3, 11.86, 12.78 or 21.9 degrees. In another embodiment, Form 3 has one, two, three, four, five, six, seven, eight, nine, ten, eleven, twelve or thirteen characteristic X-ray powder diffraction peaks as set forth in Table 16.

Figure 16:
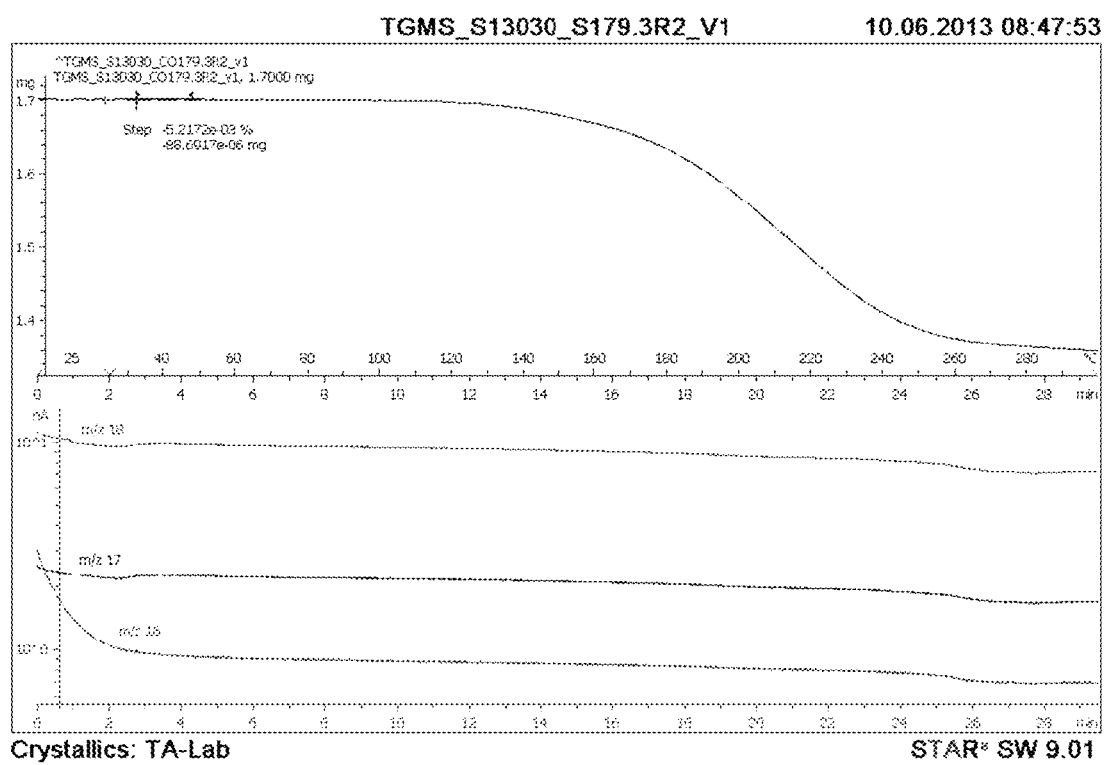
FIG. 16 depicts a thermogravimetric analysis coupled with mass spectroscopy of Form 3.

In one embodiment, provided herein is Form 3 having a thermogravimetric (TGA) thermograph corresponding substantially to the representative TGA thermogram as depicted in FIG. 16. In certain embodiments, the crystalline form exhibits a TGA thermogram comprising no significant mass loss between approximately 25° C. and approximately 100° C. when heated from approximately 25° C. to approximately 300° C.

Figure 17:
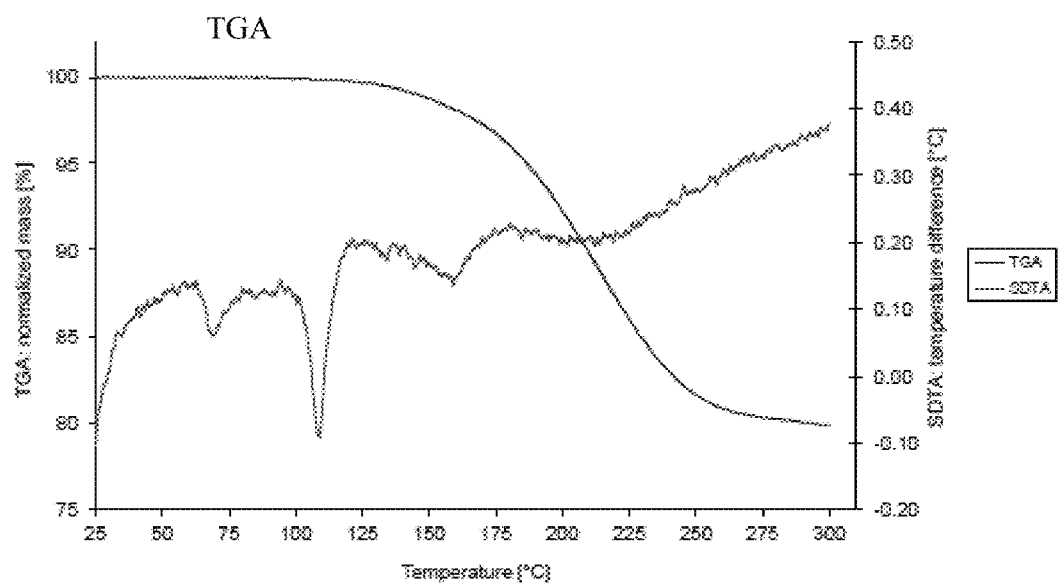
FIG. 17 depicts a thermogravimetrical analysis and single differential thermal analysis of Form 3.

In one embodiment, provided herein is Form 3 having a single differential thermal analysis (SDTA) thermogram as depicted in FIG. 17 comprising three endothermic events with the maximums at about 67.7° C., about 108° C. and about 158° C., respectively, when heated from approximately 25° C. to approximately 300° C.

In still another embodiment, Form 3 is substantially pure. In certain embodiments, the substantially pure Form 3 is substantially free of other solid forms, e.g., amorphous form. In certain embodiments, the purity of the substantially pure Form 3 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.4 Cocrystal Form 4 Comprising Compound 1 and Benzoic Acid

Provided herein is cocrystal Form 4 comprising Compound 1 and benzoic acid. In one embodiment, provided herein is a solid form comprising Compound 1 and benzoic acid that is substantially crystalline. In one embodiment, provided herein is a solid form comprising a cocrystal comprising Compound 1 and benzoic acid. In one embodiment, provided herein is a solid form comprising (i) a cocrystal comprising Compound 1 and benzoic acid and (ii) an amorphous form of Compound 1. In one embodiment, provided herein is a solid form comprising (i) a cocrystal comprising Compound 1 and benzoic acid and (ii) one or more additional crystal forms of Compound 1. Provided herein are various embodiments, preparations, or modifications of a cocrystal comprising Compound 1 and benzoic acid.

In one embodiment, Form 4 is an acetone solvated solid form comprising Compound 1 and benzoic acid. In another embodiment, Form 4 is crystalline.

In certain embodiments, Form 4 is obtained by slurry experiments, comprising 1) obtaining a slurry of Compound 1 and benzoic acid in a ratio in a solvent; 2) stirring the slurry for a period of time; 3) collecting a solid from the slurry by filtration (e.g., centrifuge filtration). In one embodiment, the solvent is a mixture of acetone and water (about 10/90). In one embodiment, the molar ratio of Compound 1 and benzoic acid is about 1:1.1. In one embodiment, the period of time is about 3 days.

In certain embodiments, a solid form provided herein, e.g., Form 4, is substantially crystalline, as indicated by, e.g., X-ray powder diffraction measurements. In one embodiment, Form 4 has an X-ray powder diffraction pattern substantially as shown in FIG. 15 (the third pattern from bottom). In one embodiment, Form 4 has one or more characteristic X-ray powder diffraction peaks at a two-theta angle of approximately 8.02, 8.86, 9.74, 12.78, 13.82, 15.58, 17.94, 19.82, 20.5, 21.02, 22.58, 24.38, 25.02 or 27.66 degrees as depicted in FIG. 15 (the third pattern from bottom). In a specific embodiment, Form 4 has one, two, three, four, five, six, seven or eight characteristic X-ray powder diffraction peaks at a two-theta angle of approximately 8.02, 9.74, 13.82, 15.58, 19.82, 21.02, 24.38 or 25.02 degrees. In another embodiment, Form 4 has one, two, three or four characteristic X-ray powder diffraction peaks at a two-theta angle of approximately 8.02, 13.82, 19.82 or 25.02 degrees. In another embodiment, Form 4 has one, two, three, four, five, six, seven, eight, nine, ten, eleven, twelve, thirteen, fourteen, fifteen or sixteen characteristic X-ray powder diffraction peaks as set forth in Table 17.

Figure 21:
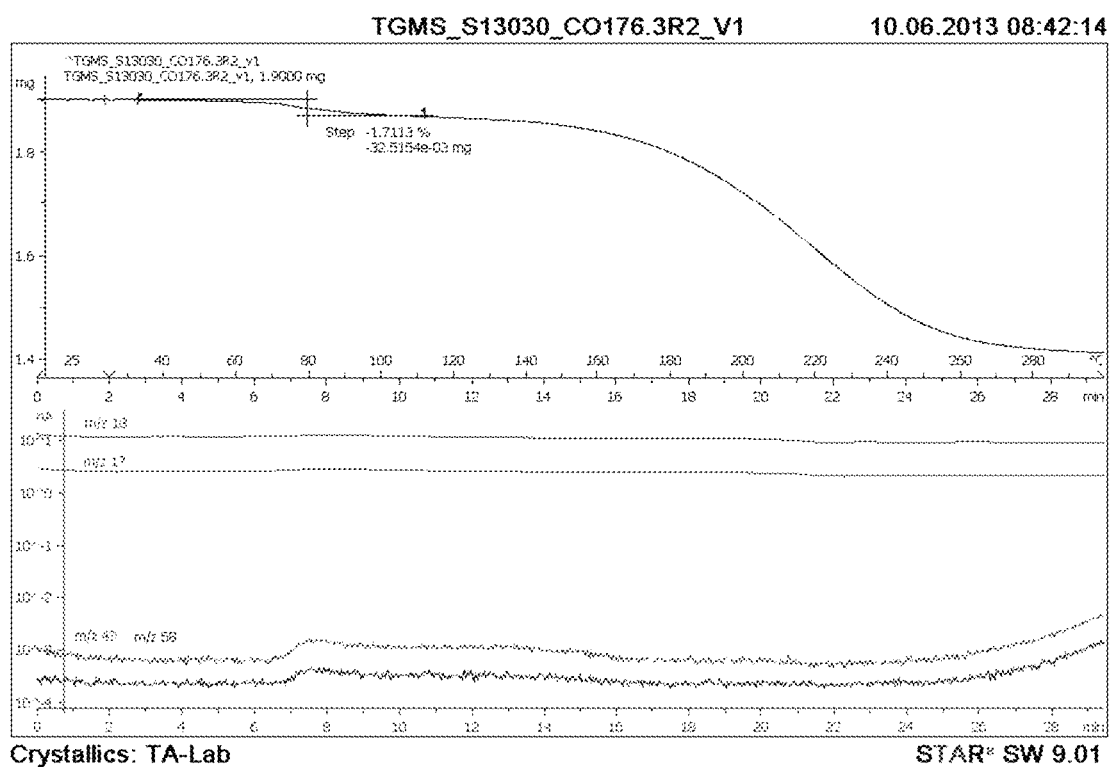
FIG. 21 depicts a thermogravimetric analysis coupled with mass spectroscopy of Form 4.

In one embodiment, provided herein is Form 4 having a thermogravimetric (TGA) thermograph corresponding substantially to the representative TGA thermogram as depicted in FIG. 21. In certain embodiments, the crystalline form exhibits a TGA thermogram comprising a total mass loss of approximately 1.7% of the total mass of the sample between approximately 35° C. and approximately 110° C. when heated from approximately 25° C. to approximately 300° C. Thus, in certain embodiments, the crystalline form loses about 1.7% of its total mass when heated from about ambient temperature to about 300° C.

Figure 22:
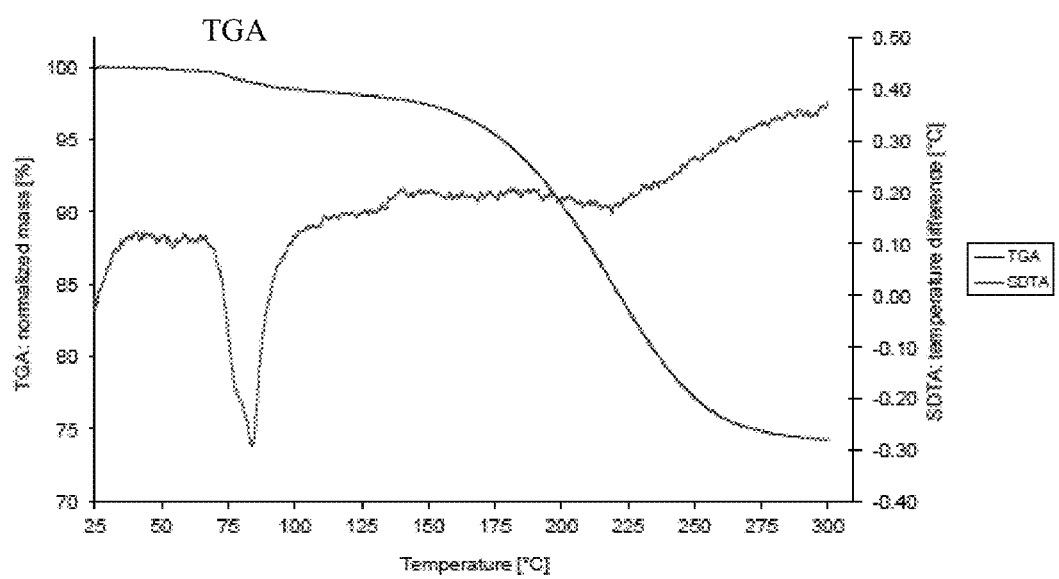
FIG. 22 depicts a thermogravimetrical analysis and single differential thermal analysis of Form 4.

In one embodiment, provided herein is Form 4 having a single differential thermal analysis (SDTA) thermogram as depicted in FIG. 22 comprising an endothermic event with a maximums at about 83.2° C., followed by decomposition starting from about 180° C., when heated from approximately 25° C. to approximately 300° C.

In still another embodiment, Form 4 is substantially pure. In certain embodiments, the substantially pure Form 4 is substantially free of other solid forms, e.g., amorphous form. In certain embodiments, the purity of the substantially pure Form 4 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.5 Cocrystal Form 5 Comprising Compound 1 and Gentisic Acid

Provided herein is cocrystal Form 5 comprising Compound 1 and gentisic acid. In one embodiment, provided herein is a solid form comprising Compound 1 and gentisic acid that is substantially crystalline. In one embodiment, provided herein is a solid form comprising a cocrystal comprising Compound 1 and gentisic acid. In one embodiment, provided herein is a solid form comprising (i) a cocrystal comprising Compound 1 and gentisic acid and (ii) an amorphous form of Compound 1. In one embodiment, provided herein is a solid form comprising (i) a cocrystal comprising Compound 1 and gentisic acid and (ii) one or more additional crystal forms of Compound 1. Provided herein are various embodiments, preparations, or modifications of a cocrystal comprising Compound 1 and gentisic acid.

In one embodiment, Form 5 is an acetone and water solvated solid form comprising Compound 1 and gentisic acid. In another embodiment, Form 5 is crystalline.

In certain embodiments, Form 5 is obtained by slurry experiments, comprising 1) obtaining a slurry of Compound 1 and gentisic acid in a ratio in a solvent; 2) stirring the slurry for a period of time; 3) collecting a solid from the slurry by filtration (e.g., centrifuge filtration). In one embodiment, the solvent is a mixture of acetone and water (about 10/90). In one embodiment, the molar ratio of Compound 1 and gentisic acid is about 1:1.1. In one embodiment, the period of time is about 3 days.

Figure 26:
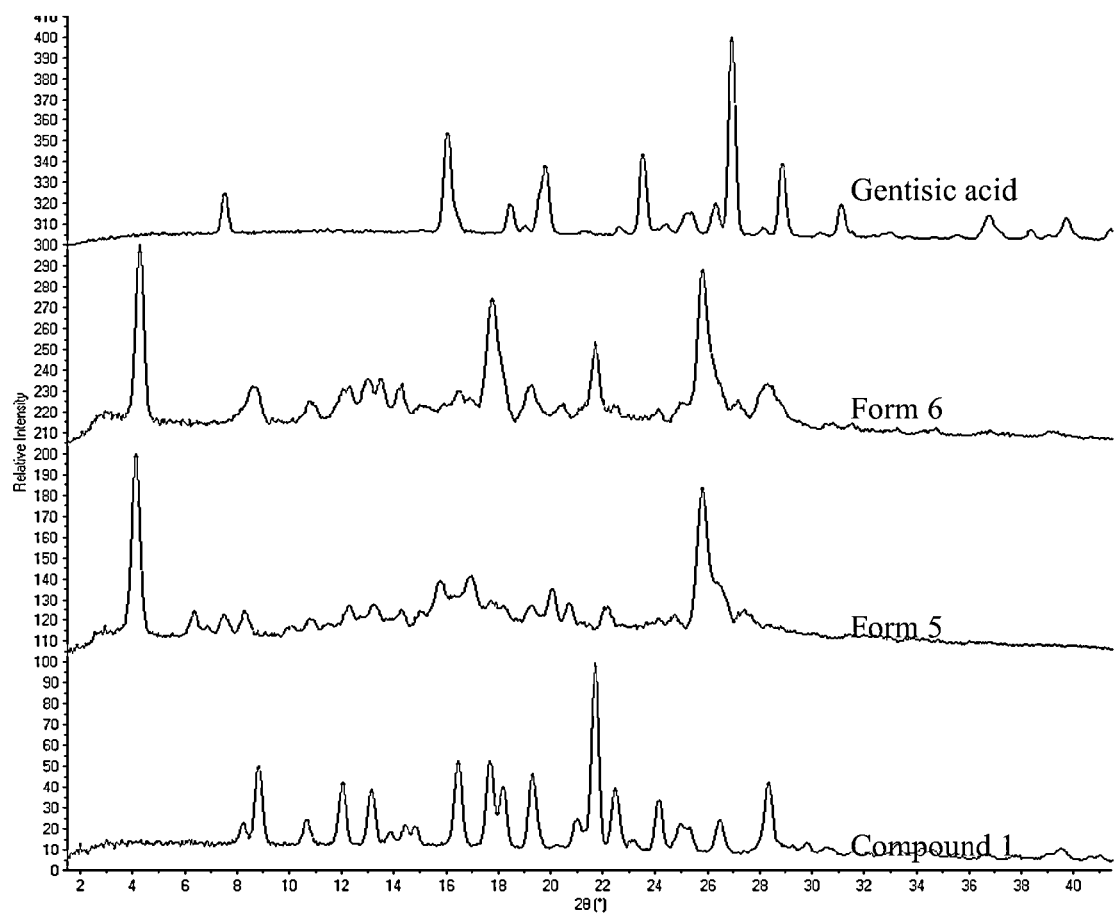
FIG. 26 depicts an X-ray powder diffractogram stack plot of Compound 1, Form 5, Form 6 and gentisic acid.

In certain embodiments, a solid form provided herein, e.g., Form 5, is substantially crystalline, as indicated by, e.g., X-ray powder diffraction measurements. In one embodiment, Form 5 has an X-ray powder diffraction pattern substantially as shown in FIG. 26 (the second pattern from bottom). In one embodiment, Form 5 has one or more characteristic X-ray powder diffraction peaks at a two-theta angle of approximately 4.1, 6.34, 8.3, 15.78, 20.06, 20.7 or 25.78 degrees as depicted in FIG. 26 (the second pattern from bottom). In another embodiment, Form 5 has one, two, three or four characteristic X-ray powder diffraction peaks at a two-theta angle of approximately 4.1, 15.78, 20.06 or 25.78 degrees. In another embodiment, Form 5 has one, two, three, four, five, six or seven characteristic X-ray powder diffraction peaks as set forth in Table 18.

Figure 27:
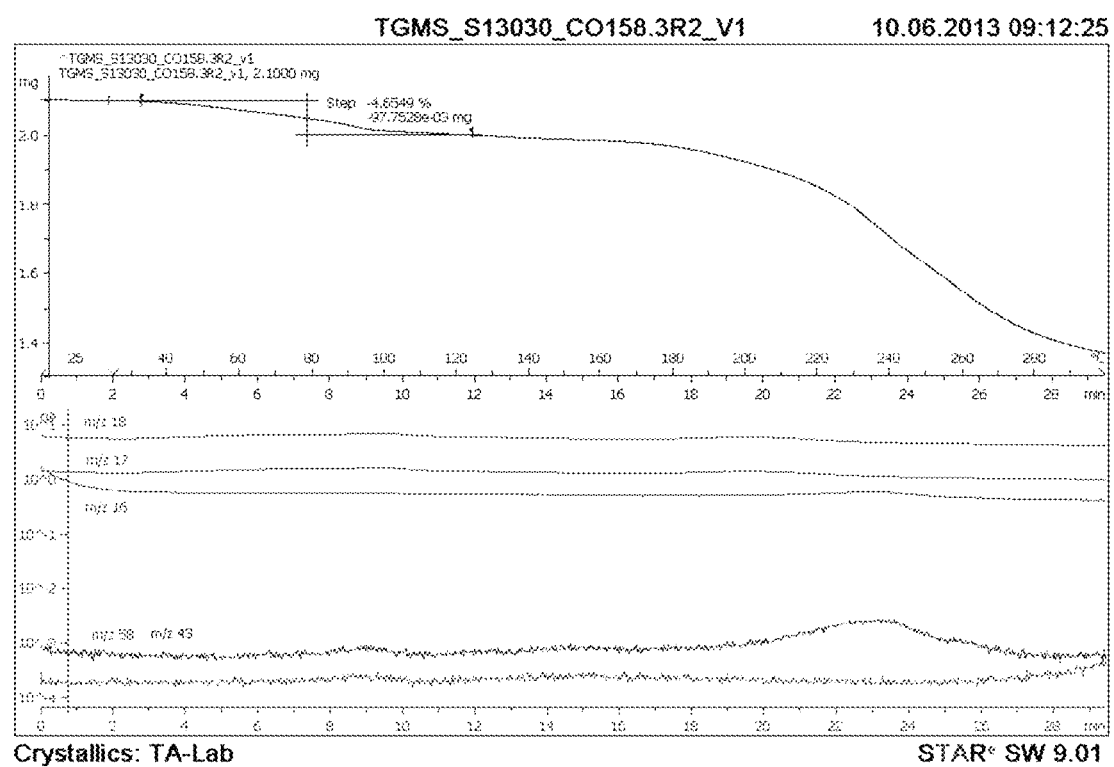
FIG. 27 depicts a thermogravimetric analysis coupled with mass spectroscopy of Form 5.

In one embodiment, provided herein is Form 5 having a thermogravimetric (TGA) thermograph corresponding substantially to the representative TGA thermogram as depicted in FIG. 27. In certain embodiments, the crystalline form exhibits a TGA thermogram comprising a total mass loss of approximately 4.6% of the total mass of the sample between approximately 25° C. and approximately 120° C. when heated from approximately 25° C. to approximately 300° C. Thus, in certain embodiments, the crystalline form loses about 4.6% of its total mass when heated from about ambient temperature to about 300° C.

Figure 28:
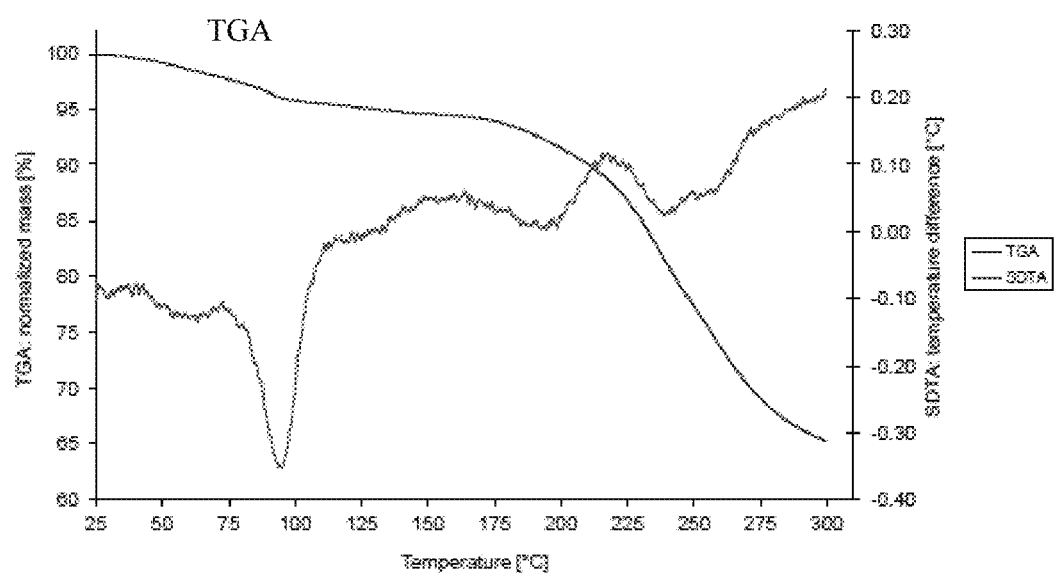
FIG. 28 depicts a thermogravimetrical analysis and single differential thermal analysis of Form 5.

In one embodiment, provided herein is Form 5 having a single differential thermal analysis (SDTA) thermogram as depicted in FIG. 28 comprising an endothermic event with a maximum at about 95.5° C., followed by decomposition starting from 180° C., when heated from approximately 25° C. to approximately 300° C.

In still another embodiment, Form 5 is substantially pure. In certain embodiments, the substantially pure Form 5 is substantially free of other solid forms, e.g., amorphous form. In certain embodiments, the purity of the substantially pure Form 5 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.6 Cocrystal Form 6 Comprising Compound 1 and Gentisic Acid

Provided herein is cocrystal Form 6 comprising Compound 1 and gentisic acid. In one embodiment, provided herein is a solid form comprising Compound 1 and gentisic acid that is substantially crystalline. In one embodiment, provided herein is a solid form comprising a cocrystal comprising Compound 1 and gentisic acid. In one embodiment, provided herein is a solid form comprising (i) a cocrystal comprising Compound 1 and gentisic acid and (ii) an amorphous form of Compound 1. In one embodiment, provided herein is a solid form comprising (i) a cocrystal comprising Compound 1 and gentisic acid and (ii) one or more additional crystal forms of Compound 1. Provided herein are various embodiments, preparations, or modifications of a cocrystal comprising Compound 1 and gentisic acid.

In one embodiment, Form 6 is an acetonitrile solvate comprising Compound 1 and gentisic acid. In another embodiment, Form 6 is crystalline.

In certain embodiments, Form 6 is obtained by slurry experiments, comprising 1) obtaining a slurry of Compound 1 and gentisic acid in a ratio in a solvent; 2) stirring the slurry for a period of time; 3) collecting a solid from the slurry by filtration (e.g., centrifuge filtration). In one embodiment, the solvent is aceonitrile. In one embodiment, the molar ratio of Compound 1 and gentisic acid is about 1:1.1. In one embodiment, the period of time is about 3 days.

In certain embodiments, a solid form provided herein, e.g., Form 6, is substantially crystalline, as indicated by, e.g., X-ray powder diffraction measurements. In one embodiment, Form 6 has an X-ray powder diffraction pattern substantially as shown in FIG. 26 (the third pattern from bottom). In one embodiment, Form 6 has one or more characteristic X-ray powder diffraction peaks at a two-theta angle of approximately 4.26, 13.02, 13.5, 14.22, 17.78, 19.22, 21.7 or 25.82 degrees as depicted in FIG. 26 (the third pattern from bottom). In another embodiment, Form 6 has one, two, three or four characteristic X-ray powder diffraction peaks at a two-theta angle of approximately 4.26, 17.78, 21.7 or 25.82 degrees. In another embodiment, Form 6 has one, two, three, four, five, six, seven or eight characteristic X-ray powder diffraction peaks as set forth in Table 19.

Figure 32:
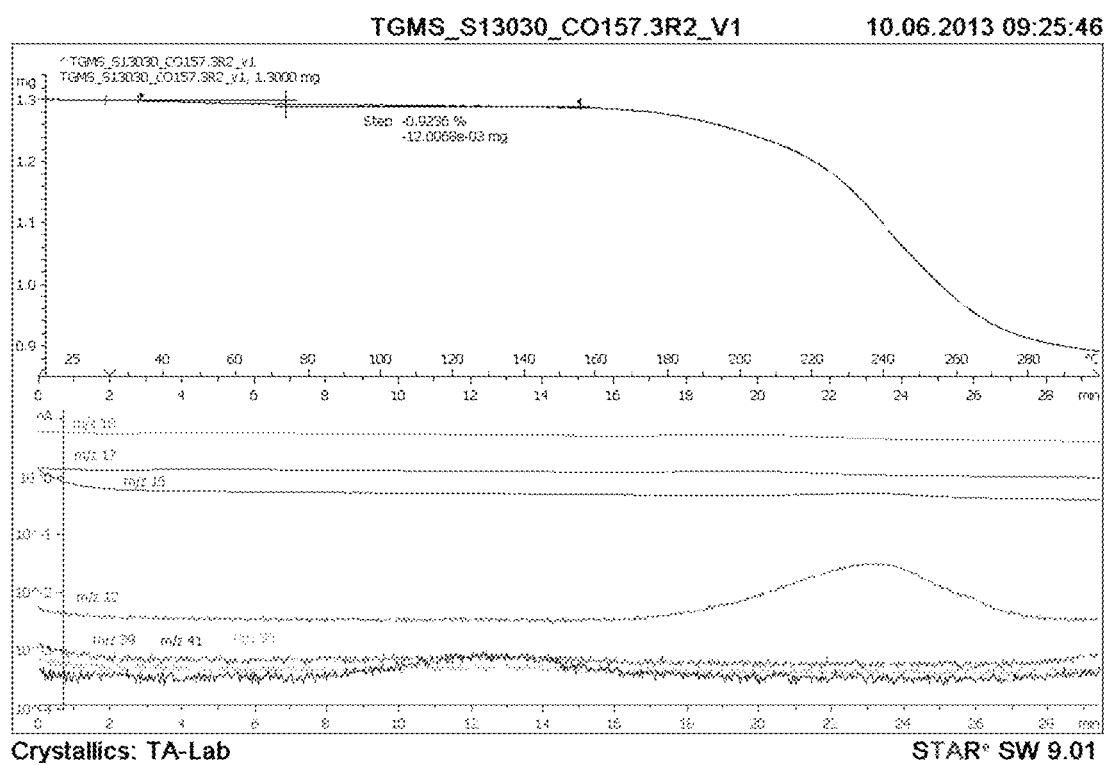
FIG. 32 depicts a thermogravimetric analysis coupled with mass spectroscopy of Form 6.

In one embodiment, provided herein is Form 6 having a thermogravimetric (TGA) thermograph corresponding substantially to the representative TGA thermogram as depicted in FIG. 32. In certain embodiments, the crystalline form exhibits a TGA thermogram comprising a total mass loss of approximately 0.9% of the total mass of the sample between about 70° C. and about 160° C. when heated from approximately 25° C. to approximately 300° C. Thus, in certain embodiments, the crystalline form loses about 0.9% of its total mass when heated from about ambient temperature to about 300° C.

Figure 33:
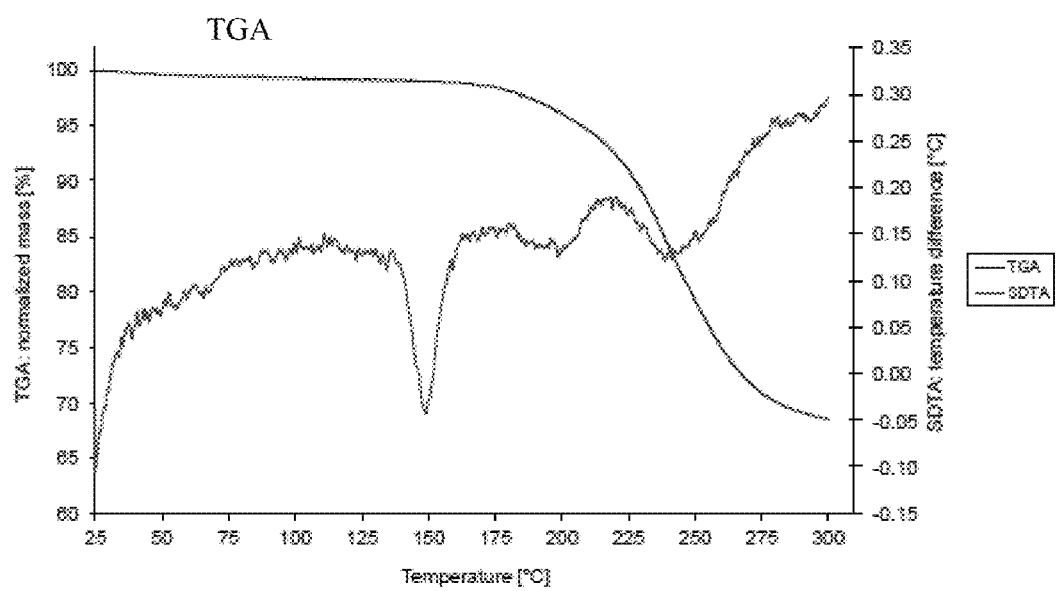
FIG. 33 depicts a thermogravimetrical analysis and single differential thermal analysis of Form 6.

In one embodiment, provided herein is Form 6 having a single differential thermal analysis (SDTA) thermogram as depicted in FIG. 33 comprising an endothermic event with a maximum at about 148° C., followed by immediate decomposition, when heated from approximately 25° C. to approximately 300° C.

In still another embodiment, Form 6 is substantially pure. In certain embodiments, the substantially pure Form 6 is substantially free of other solid forms, e.g., amorphous form. In certain embodiments, the purity of the substantially pure Form 6 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.7 Cocrystal Form 7 Comprising Compound 1 and Maleic Acid

Provided herein is cocrystal Form 7 comprising Compound 1 and maleic acid. In one embodiment, provided herein is a solid form comprising Compound 1 and maleic acid that is substantially crystalline. In one embodiment, provided herein is a solid form comprising a cocrystal comprising Compound 1 and maleic acid. In one embodiment, provided herein is a solid form comprising (i) a cocrystal comprising Compound 1 and maleic acid and (ii) an amorphous form of Compound 1. In one embodiment, provided herein is a solid form comprising (i) a cocrystal comprising Compound 1 and maleic acid and (ii) one or more additional crystal forms of Compound 1. Provided herein are various embodiments, preparations, or modifications of a cocrystal comprising Compound 1 and maleic acid.

In one embodiment, Form 7 is an acetonitrile and water solvate comprising Compound 1 and maleic acid. In another embodiment, Form 7 is crystalline.

In certain embodiments, Form 7 is obtained by slurry experiments, comprising 1) obtaining a slurry of Compound 1 and maleic acid in a ratio in a solvent; 2) stirring the slurry for a period of time; 3) collecting a solid from the slurry by filtration (e.g., centrifuge filtration). In one embodiment, the solvent is aceonitrile. In one embodiment, the molar ratio of Compound 1 and maleic acid is about 1:1.1. In one embodiment, the period of time is about 3 days.

Figure 37:
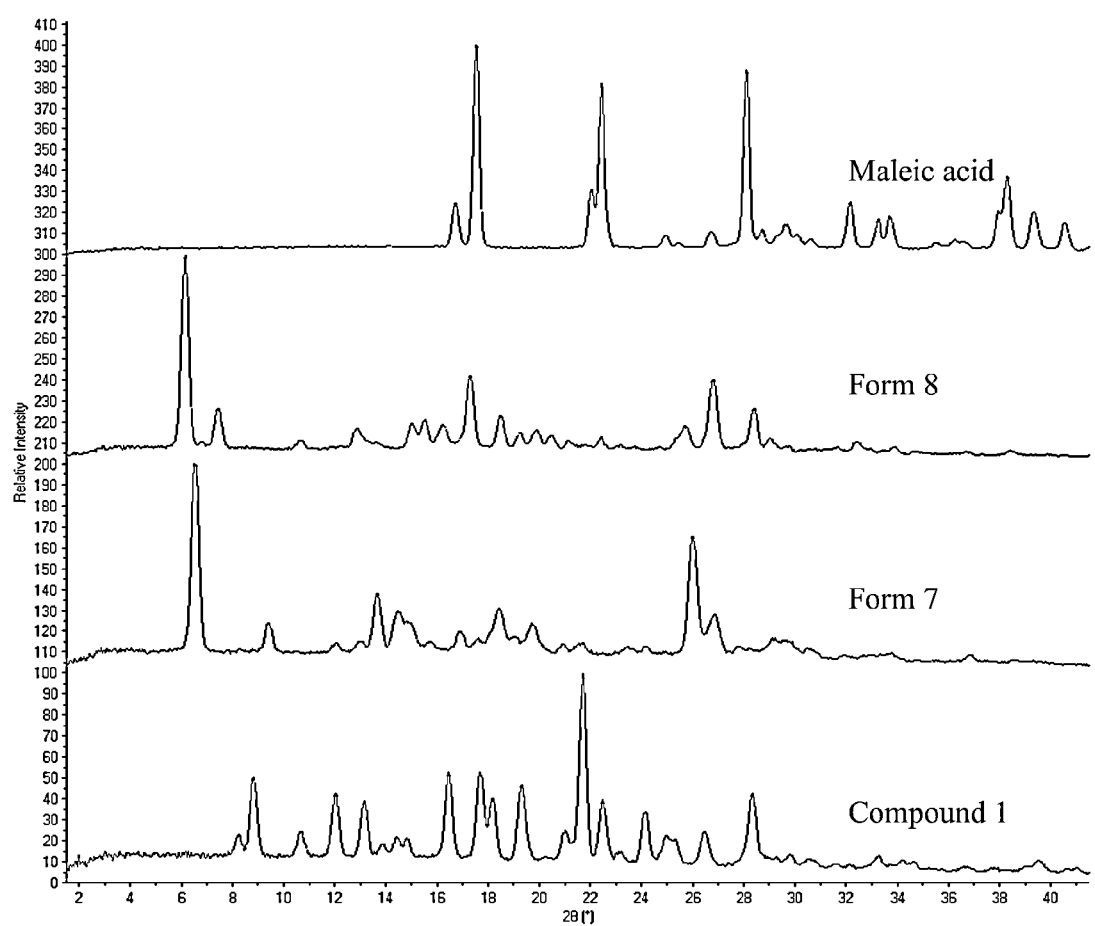
FIG. 37 depicts an X-ray powder diffractogram stack plot of Compound 1, Form 7, Form 8 and maleic acid.

In certain embodiments, a solid form provided herein, e.g., Form 7, is substantially crystalline, as indicated by, e.g., X-ray powder diffraction measurements. In one embodiment, Form 7 has an X-ray powder diffraction pattern substantially as shown in FIG. 37 (the second pattern from bottom). In one embodiment, Form 7 has one or more characteristic X-ray powder diffraction peaks at a two-theta angle of approximately 6.54, 9.42, 13.66, 18.42, 26.02 or 26.82 degrees as depicted in FIG. 37 (the second pattern from bottom). In another embodiment, Form 7 has one, two, three or four characteristic X-ray powder diffraction peaks at a two-theta angle of approximately 6.54, 13.66, 18.42 or 26.02 degrees. In another embodiment, Form 7 has one, two, three, four, five or six characteristic X-ray powder diffraction peaks as set forth in Table 20.

Figure 38:
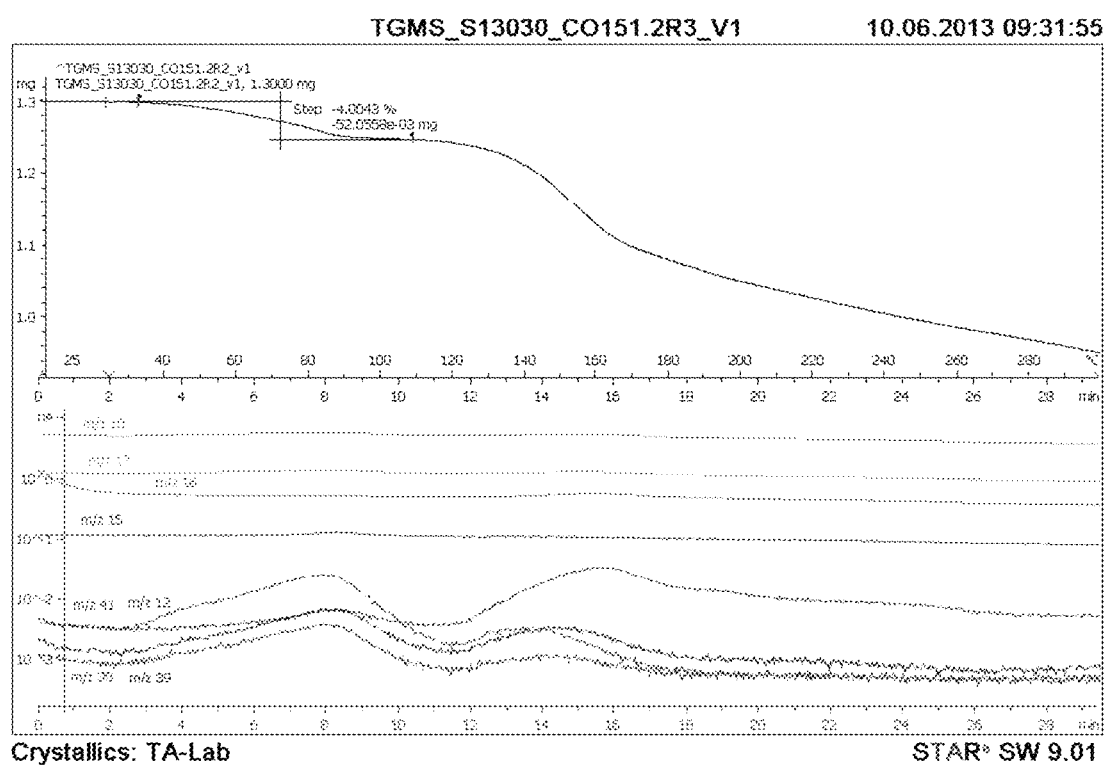
FIG. 38 depicts a thermogravimetric analysis coupled with mass spectroscopy of Form 7.

In one embodiment, provided herein is Form 7 having a thermogravimetric (TGA) thermograph corresponding substantially to the representative TGA thermogram as depicted in FIG. 38. In certain embodiments, the crystalline form exhibits a TGA thermogram comprising a total mass loss of approximately 4% of the total mass of the sample between approximately 35° C. and approximately 110° C. when heated from approximately 25° C. to approximately 300° C. Thus, in certain embodiments, the crystalline form loses about 4% of its total mass when heated from about ambient temperature to about 300° C.

Figure 39:
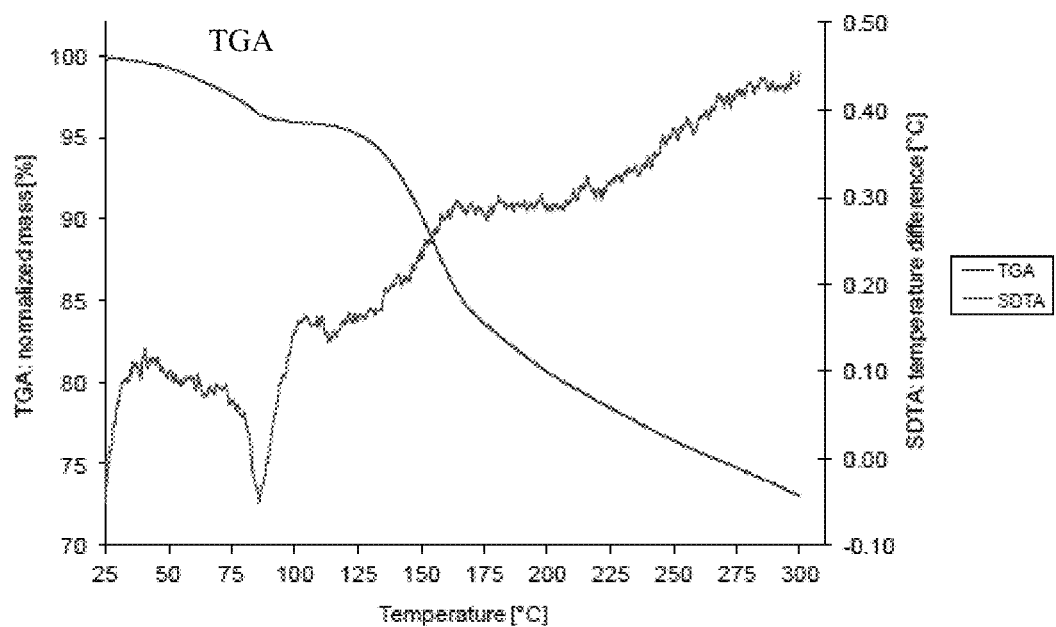
FIG. 39 depicts a thermogravimetrical analysis and single differential thermal analysis of Form 7.

In one embodiment, provided herein is Form 7 having a single differential thermal analysis (SDTA) thermogram as depicted in FIG. 39 comprising an endothermic event with a maximum at about 86° C., followed by decomposition starting from about 115° C., when heated from approximately 25° C. to approximately 300° C.

In still another embodiment, Form 7 is substantially pure. In certain embodiments, the substantially pure Form 7 is substantially free of other solid forms, e.g., amorphous form. In certain embodiments, the purity of the substantially pure Form 7 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.8 Cocrystal Form 8 Comprising Compound 1 and Maleic Acid

Provided herein is cocrystal Form 8 comprising Compound 1 and maleic acid. In one embodiment, provided herein is a solid form comprising Compound 1 and maleic acid that is substantially crystalline. In one embodiment, provided herein is a solid form comprising a cocrystal comprising Compound 1 and maleic acid. In one embodiment, provided herein is a solid form comprising (i) a cocrystal comprising Compound 1 and maleic acid and (ii) an amorphous form of Compound 1. In one embodiment, provided herein is a solid form comprising (i) a cocrystal comprising Compound 1 and maleic acid and (ii) one or more additional crystal forms of Compound 1. Provided herein are various embodiments, preparations, or modifications of a cocrystal comprising Compound 1 and maleic acid.

In one embodiment, Form 8 is an ethyl acetate solvate comprising Compound 1 and maleic acid. In another embodiment, Form 8 is crystalline.

In certain embodiments, Form 8 is obtained by cooling evaporative experiments comprising 1) obtaining a close-to saturated solution of Compound 1 and maleic acid in a ratio (e.g., about 1:1.1) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., about 48 hours); 5) filtering the solution to yield a solid if there is precipitation; and 6) evaporating the solvent to collect a solid if there is no precipitation after step 4. In certain embodiments, Form 2 is obtained by cooling evaporative experiments, comprising 1) obtaining a close-to saturated solution of Compound 1 and maleic acid in a solvent; 2) heating the solution to about 40° C.); 3) cooling the solution to about 2° C.); 4) keeping the solution at about 2° C. for about 48 hrs; 5) filtering the solution to yield a solid if there is precipitation; and 6) evaporating the solvent to collect a solid if there is no precipitation after step 4. In one embodiment, the solvent is ethyl acetate. In one embodiment, the molar ratio of Compound 1 and maleic acid in step 1 is about 1:1.4.

In certain embodiments, a solid form provided herein, e.g., Form 8, is substantially crystalline, as indicated by, e.g., X-ray powder diffraction measurements. In one embodiment, Form 8 has an X-ray powder diffraction pattern substantially as shown in FIG. 37 (the third pattern from bottom). In one embodiment, Form 8 has one or more characteristic X-ray powder diffraction peaks at a two-theta angle of approximately 6.14, 7.42, 15.5, 17.3, 18.46, 26.78 or 28.38 degrees as depicted in FIG. 37 (the third pattern from bottom). In another embodiment, Form 8 has one, two, three or four characteristic X-ray powder diffraction peaks at a two-theta angle of approximately 6.14, 17.3, 26.78 or 28.38 degrees. In another embodiment, Form 8 has one, two, three, four, five, six or seven characteristic X-ray powder diffraction peaks as set forth in Table 21.

Figure 43:
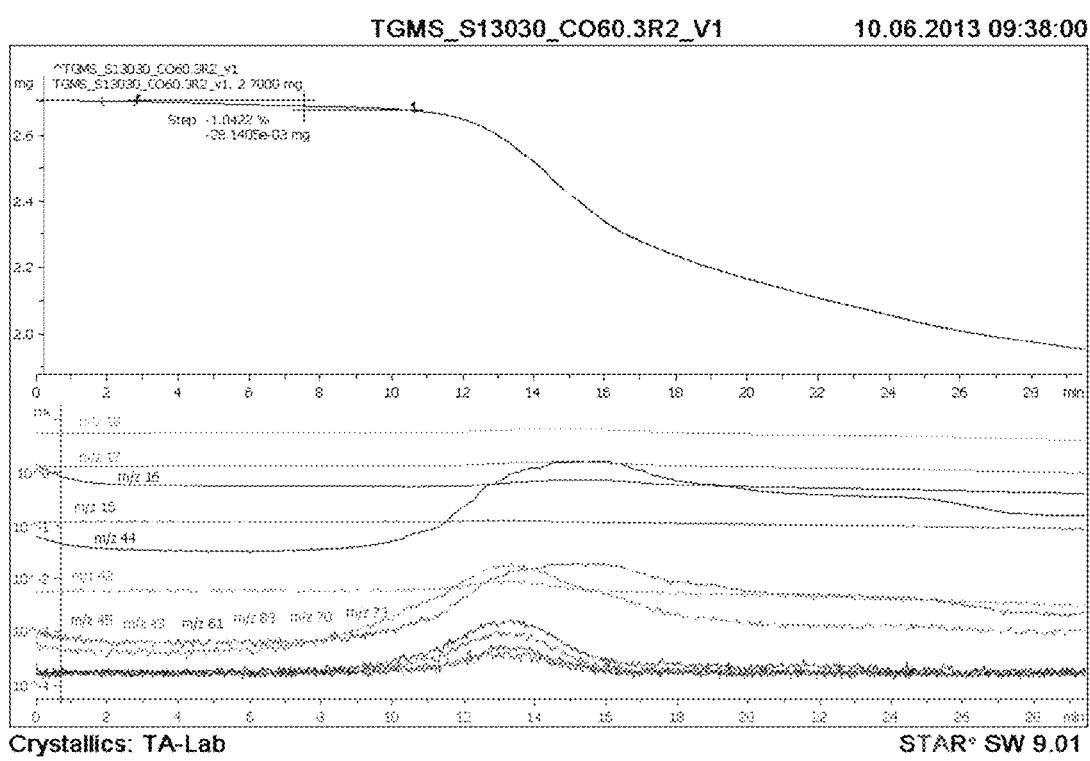
FIG. 43 depicts a thermogravimetric analysis coupled with mass spectroscopy of Form 8.

In one embodiment, provided herein is Form 8 having a thermogravimetric (TGA) thermograph corresponding substantially to the representative TGA thermogram as depicted in FIG. 43. In certain embodiments, the crystalline form exhibits a TGA thermogram comprising a total mass loss of approximately 1% of the total mass of the sample between approximately 35° C. and approximately 110° C. when heated from approximately 25° C. to approximately 300° C. Thus, in certain embodiments, the crystalline form loses about 1% of its total mass when heated from about ambient temperature to about 300° C.

Figure 44:
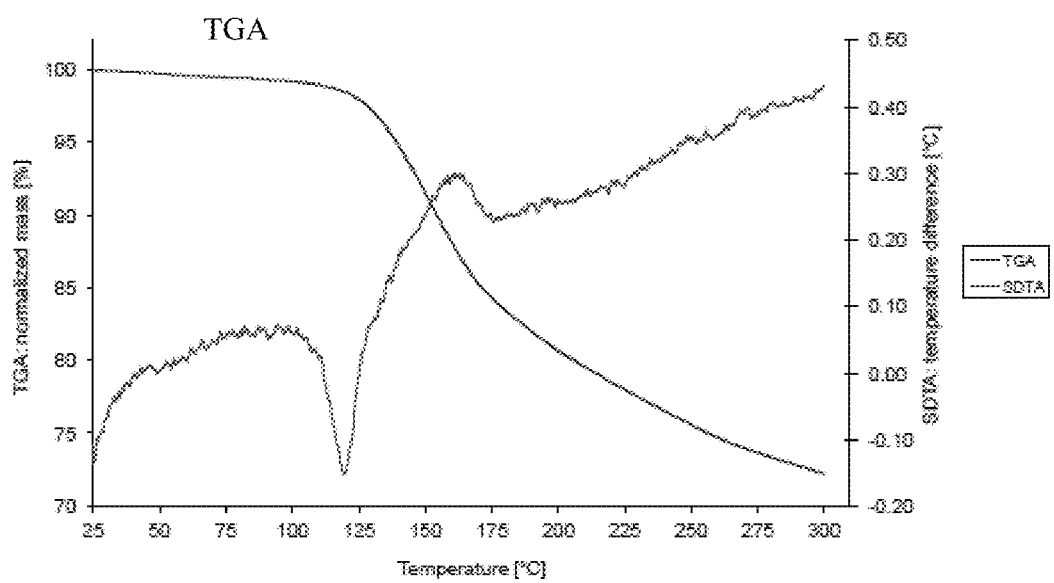
FIG. 44 depicts a thermogravimetrical analysis and single differential thermal analysis of Form 8.

In one embodiment, provided herein is Form 8 having a single differential thermal analysis (SDTA) thermogram as depicted in FIG. 44 comprising an endothermic event with a maximum at about 118.8° C., followed by decomposition, when heated from approximately 25° C. to approximately 300° C.

In still another embodiment, Form 8 is substantially pure. In certain embodiments, the substantially pure Form 8 is substantially free of other solid forms, e.g., amorphous form. In certain embodiments, the purity of the substantially pure Form 8 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.4 Methods of Use

The solid forms and the pharmaceutical compositions provided herein can be used in all the methods provided herein. The solid forms and the pharmaceutical compositions provided herein can be used in the treatment of all diseases, disorders or conditions provided herein.

The solid forms of Compound 1 (e.g., Form 1, Form 2, Form 3, Form 4, Form 5, Form 6, Form 7 or Form 8) have utility as pharmaceuticals to treat or prevent a disease in a subject, e.g., a proliferative disease. Further, the solid forms of Compound 1 (e.g., Form 1, Form 2, Form 3, Form 4, Form 5, Form 6, Form 7 or Form 8) provided herein are active against kinases (e.g., protein kinases), including those involved in cancer, inflammatory conditions, immunological conditions, neurodegenerative diseases, diabetes, obesity, neurological disorders, age-related diseases, and/or cardiovascular conditions. Without being limited by theory, it is thought the solid forms of Compound 1 (e.g., Form 1, Form 2, Form 3, Form 4, Form 5, Form 6, Form 7 or Form 8) provided herein are effective for treating and preventing diseases and conditions due to its ability to modulate (e g., inhibit) kinases that are involved in the etiology of the diseases and conditions. Accordingly, provided herein are uses of the solid forms of Compound 1 (e.g., Form 1, Form 2, Form 3, Form 4, Form 5, Form 6, Form 7 or Form 8) provided herein, including the treatment or prevention of those diseases set forth herein. In certain embodiments, the methods provided herein comprise administering a solid form of Compound 1 (e.g., Form 1, Form 2, Form 3, Form 4, Form 5, Form 6, Form 7 or Form 8) provided herein, wherein the solid form of Compound 1 (e.g., Form 1, Form 2, Form 3, Form 4, Form 5, Form 6, Form 7 or Form 8) is part of a kit provided herein.

In one embodiment, provided herein is a method of treating and preventing a disease or condition in a subject, comprising the administration of an effective amount of the solid form of Compound 1 (e.g., Form 1, Form 2, Form 3, Form 4, Form 5, Form 6, Form 7 or Form 8) provided herein to the subject.

Representative immunological conditions that the solid forms of Compound 1 (e.g., Form 1, Form 2, Form 3, Form 4, Form 5, Form 6, Form 7 or Form 8) provided herein are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Graves disease, encephalomyelitis, Type II diabetes, dermatomyositis, and transplant rejection (e.g., in the treatment of recipients of heart, lung, combined heart-lung, liver, kidney, pancreatic, skin, or corneal transplants; or graft-versus-host disease, such as following bone marrow transplantation).

Representative inflammatory conditions that the solid forms of Compound 1 (e.g., Form 1, Form 2, Form 3, Form 4, Form 5, Form 6, Form 7 or Form 8) provided herein are useful for treating or preventing include, but are not limited to, psoriasis, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, and obesity.

Representative cardiovascular diseases that the solids form of Compound 1 (e.g., Form 1, Form 2, Form 3, Form 4, Form 5, Form 6, Form 7 or Form 8) provided herein are useful for treating or preventing include, but are not limited to, restenosis, Wolf-Parkinson-White Syndrome, stroke, myocardial infarction or ischemic damage to the heart, lung, gut, kidney, liver, pancreas, spleen or brain.

Representative neurodegenerative diseases that the solid forms of Compound 1 (e.g., Form 1, Form 2, Form 3, Form 4, Form 5, Form 6, Form 7 or Form 8) provided herein are useful for treating or preventing include, but are not limited to, Huntington's disease, Alzheimer's disease, Parkinson's disease, dementias caused by tau mutations, spinocerebellar ataxia type 3, motor neuron disease caused by SOD1 mutations, neuronal ceroid lipofucinoses/Batten disease (pediatric neurodegene ration) and HIV-associated encephalitis.

Representative age-related diseases that the solid forms of Compound 1 (e.g., Form 1, Form 2, Form 3, Form 4, Form 5, Form 6, Form 7 or Form 8) provided herein are useful for treating or preventing include, but are not limited to, cancer, obesity, type II diabetes mellitus, autoimmune disease, cardiovascular diseases and neuronal degeneration.

In certain embodiments, the disease or condition is a fibrotic disease or disorder. Thus, in one embodiment, provided herein is a method for treating or preventing a fibrotic disease or disorder in a subject, comprising the administration of an effective amount of the solid form of Compound 1 (e.g., Form 1, Form 2, Form 3, Form 4, Form 5, Form 6, Form 7 or Form 8) provided herein to the subject. In another embodiment, provided herein is a method of treating or preventing scleroderma, idiopathic pulmonary fibrosis, renal fibrosis, cystic fibrosis, myelofibrosis, hepatic fibrosis, steatofibrosis or steatohepatitis in a subject, comprising the administration of an effective amount of the solid form of Compound 1 (e.g., Form 1, Form 2, Form 3, Form 4, Form 5, Form 6, Form 7 or Form 8) provided herein to the subject.

Representative cancers that the solid forms of Compound 1 (e.g., Form 1, Form 2, Form 3, Form 4, Form 5, Form 6, Form 7 or Form 8) provided herein are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. The solid forms of Compound 1 (e.g., Form 1, Form 2, Form 3, Form 4, Form 5, Form 6, Form 7 or Form 8) provided hereinare also useful for treating or preventing solid tumors and bloodborne tumors.

In some embodiments, the cancers within the scope of the methods provided herein include those associated with the pathways involving mTOR, PI3K, or Akt kinases and mutants or isoforms thereof. In some embodiments, the cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas.

In one embodiment, provided herein is a method for treating or preventing a disease or disorder associated with activation of mTOR signaling, comprising the administration of an effective amount of the solid form of Compound 1 (e.g., Form 1, Form 2, Form 3, Form 4, Form 5, Form 6, Form 7 or Form 8) provided herein to a subject in need thereof. Examples of diseases or disorders associated with activation of mTOR signaling include, but are not limited to, tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), LKB1, VHL (von Hippel-Lindau disease) and PKD1 (polycystin-1). Without being limited by theory, it is thought that genetic defects associated with these proteins results in hyperactivation of the mTOR/PI3K/Akt pathway. In certain embodiments, the diseases which are treatable or preventable through inhibition of the mTOR/PI3K/Akt pathway include, but are not limited to, Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, *Proteus* syndrome, and polycystic kidney disease.

In another embodiment, provided herein is a method for treating or preventing a disease or disorder associated with mTOR, PI3K, Akt, and/or DNA-PK signaling, comprising the administration of an effective amount of the solid form of Compound 1 (e.g., Form 1, Form 2, Form 3, Form 4, Form 5, Form 6, Form 7 or Form 8) provided here into a subject in need thereof. Examples of diseases which are treatable or preventable by inhibiting mTOR, PI3K, Akt and/or DNA-PK signaling, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases (including retinitis pigmentosa), solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

In yet another embodiment, provided herein is a method of inhibiting a kinase in a cell expressing the kinase, comprising contacting the cell with an effective amount of the solid form of Compound 1 (e.g., Form 1, Form 2, Form 3, Form 4, Form 5, Form 6, Form 7 or Form 8) provided herein. In one embodiment, the kinase is TOR kinase. In certain embodiments, the cell is in a subject. In certain embodiments, the cell is from a subject.

In yet another embodiment, provided herein is a method of treating or preventing a condition treatable or preventable by the inhibition of a kinase pathway, in one embodiment, the mTOR/PI3K/Akt and/or DNA-PK pathway, comprising administering to a subject in need thereof an effective amount of the solid form of Compound 1 (e.g., Form 1, Form 2, Form 3, Form 4, Form 5, Form 6, Form 7 or Form 8) provided herein. Conditions treatable or preventable by the inhibition of the mTOR/PI3K/Akt pathway include, but are not limited to, solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; sarcomas; tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), and LKB1, VHL (von Hippel-Lindau disease) and PKD1 (polycystin-1); Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, *Proteus* syndrome, and polycystic kidney disease; rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases, including retinitis pigmentosa, solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

Provided herein are methods for treating or preventing a solid tumor, non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided herein to a subject having a solid tumor, non-Hodgkin lymphoma or multiple myeloma. In one embodiment, the solid tumor, non-Hodgkin lymphoma or multiple myeloma, is rapamycin resistant.

In one embodiment, the non-Hodgkin lymphoma is diffuse large B-cell lymphoma (DLBCL), follicular lymphoma (FL), acute myeloid leukemia (AML), mantle cell lymphoma (MCL), or ALK$^+$ anaplastic large cell lymphoma. In one embodiment, the non-Hodgkin lymphoma is advanced solid non-Hodgkin lymphoma.

In other embodiments, the cancer is a solid tumor. In certain embodiments, the solid tumor is a relapsed or refractory solid tumor.

In other embodiments, the solid tumor can be an advanced solid tumor.

In other embodiments, the solid tumor can be a neuroendocrine tumor, glioblastoma multiforme (GBM), hepatocellular carcinoma (HCC), breast cancer, colorectal cancer (CRC), salivary cancer, pancreatic cancer, adenocystic cancer, adrenal cancer, esophageal cancer, renal cancer, leiomyosarcoma, paraganglioma, head and neck squamous cell carcinoma, E-twenty six (ETS) overexpressing castration-resistant prostate cancer or E-twenty six (ETS) overexpressing Ewings sarcoma.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In some embodiments, the neuroendocrine tumor is of non-gut origin, for example a bronchial neuroendocrine tumor, or a neuroendocrine tumor with origin in an organ above the diaphragm, for example, a laryngeal neuroendocrine tumor, a pharyngeal neuroendocrine tumor, or a thyroid neuroendocrine tumor. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the solid tumor is non-small cell lung cancer (NSCLC).

In another embodiments the solid tumor is glioblastoma multiforme (GBM).

In another embodiment, the solid tumor is hepatocellular carcinoma (HCC).

In another embodiment, the solid tumor is breast cancer. In one embodiment, the breast cancer is estrogen receptor positive (ER+, ER+/Her2− or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment, the solid tumor is colorectal cancer.

In another embodiment, the solid tumor is salivary cancer.

In another embodiment, the solid tumor is pancreatic cancer.

In another embodiment, the solid tumor is adenocystic cancer.

In another embodiment, the solid tumor is adrenal cancer.

In another embodiment, the solid tumor is esophageal cancer.

In another embodiment, the solid tumor is renal cancer.

In another embodiment, the solid tumor is leiomyosarcoma.

In another embodiment, the solid tumor is paraganglioma.

In one embodiment, the solid tumor is an advanced solid tumor.

In one embodiment, the advanced solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In some embodiments, the neuroendocrine tumor is of non-gut origin, for example a bronchial neuroendocrine tumor, or a neuroendocrine tumor with origin in an organ above the diaphragm, for example, a laryngeal neuroendocrine tumor, a pharyngeal neuroendocrine tumor, or a thyroid neuroendocrine tumor. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the advanced solid tumor is non-small cell lung cancer (NSCLC).

In another embodiments the advanced solid tumor is glioblastoma multiforme (GBM).

In another embodiment, the advanced solid tumor is hepatocellular carcinoma (HCC).

In another embodiment, the advanced solid tumor is breast cancer. In one embodiment, the advanced solid tumor is estrogen receptor positive (ER+, ER+/Her2− or ER+/Her2+) breast cancer. In one embodiment, the advanced solid tumor is ER+/Her2− breast cancer. In one embodiment, the advanced solid tumor is ER+/Her2+ breast cancer. In one embodiment, the advanced solid tumor is ER−/Her2+ breast cancer. In one embodiment, the advanced solid tumor is triple negative (TN) breast cancer.

In another embodiment, the advanced solid tumor is colorectal cancer.

In another embodiment, the advanced solid tumor is salivary cancer.

In another embodiment, the advanced solid tumor is pancreatic cancer.

In another embodiment, the advanced solid tumor is adenocystic cancer.

In another embodiment, the advanced solid tumor is adrenal cancer.

In another embodiment, the advanced solid tumor is esophageal cancer.

In another embodiment, the advanced solid tumor is renal cancer.

In another embodiment, the advanced solid tumor is leiomyosarcoma.

In another embodiment, the advanced solid tumor is or paraganglioma.

In one embodiment, the non-Hodgkin lymphoma is diffuse large B-cell lymphoma (DLBCL).

In one embodiment, provided herein are methods for achieving a Response Evaluation Criteria in Solid Tumors (RECIST 1.1) (see Eisenhauer E. A., Therasse P., Bogaerts J., et al. New response evaluation criteria in solid tumours: Revised RECIST guideline (version 1.1). European J. Cancer; 2009; (45) 228-247) of complete response, partial response or stable disease in a patient comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

In one embodiment, provided herein are methods for preventing or delaying a Response Evaluation Criteria in Solid Tumors (RECIST 1.1) of progressive disease in a subject, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain.

In certain embodiments, provided herein are methods for decreasing the size of target lesions in a subject compared to pre-treatment, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

In certain embodiments, provided herein are methods for decreasing the size of a non-target lesion in a subject compared to pre-treatment, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

In certain embodiments, provided herein are methods for achieving a reduction in the number of target lesions in a subject compared to pre-treatment, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

In certain embodiments, provided herein are methods for achieving a reduction in the number of non-target lesions in a subject compared to pre-treatment, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

In certain embodiments, provided herein are methods for achieving an absence of all target lesions in a subject, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

In certain embodiments, provided herein are methods for achieving an absence of all non-target lesions in a subject, comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor.

A method of treating a solid tumor, such as an advanced solid tumor, the method comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor, wherein the treatment results in a complete response, partial response or stable disease, as determined by Response Evaluation Criteria in Solid Tumors (RECIST 1.1).

A method of treating a solid tumor, such as an advanced solid tumor, the method comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor, wherein the treatment results in a reduction in target lesion size, a reduction in non-target lesion size and/or the absence of new target and/or non-target lesions, compared to pre-treatment.

A method of treating a solid tumor, such as an advanced solid tumor, the method comprising administering an effective amount of the solid form of Compound 1 (e.g., Form 1, Form 2, Form 3, Form 4, Form 5, Form 6, Form 7 or Form 8) provided herein to a subject having a solid tumor, such as an advanced solid tumor, wherein the treatment results in prevention or retarding of clinical progression, such as cancer-related cachexia or increased pain.

In another embodiment, provided herein are methods for improving the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586.) of a subject comprising administering an effective amount of the solid form of Compound 1 (e.g., Form 1, Form 2, Form 3, Form 4, Form 5, Form 6, Form 7 or Form 8) provided herein to a subject having non-Hodgkin lymphoma. In another embodiment, provided herein are methods to increase Progression Free Survival rates, as determined by Kaplan-Meier estimates. In one embodiment, the treatment results in a complete remission, partial remission or stable disease, as determined by the International Workshop Criteria (IWC) for NHL. In another embodiment, the treatment results in an increase in overall survival, progression-free survival, event-free survival, time to progression, disease-free survival or lymphoma-free survival.

In another embodiment, provided herein are methods for inducing a therapeutic response characterized with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a subject comprising administering an effective amount of the solid form of Compound 1 (e.g., Form 1, Form 2, Form 3, Form 4, Form 5, Form 6, Form 7 or Form 8) provided herein to a subject having multiple myeloma. In one embodiment, the treatment results in a stringent complete response, complete response, or very good partial response, as determined by the International Uniform Response Criteria for Multiple Myeloma (IURC). In another embodiment, the treatment results in an increase in overall survival, progression-free survival, event-free survival, time to progression, or disease-free survival.

In another embodiment, provided herein are methods for inducing a therapeutic response assessed with Response Assessment for Neuro-Oncology (RANO) Working Group for GBM (see Wen P., Macdonald, D R., Reardon, D A., et al. Updated response assessment criteria for highgrade gliomas: Response assessment in neuro-oncology working group. J. Clin. Oncol. 2010; 28: 1963-1972) of a subject comprising administering an effective amount of the solid form of Compound 1 (e.g., Form 1, Form 2, Form 3, Form 4, Form 5, Form 6, Form 7 or Form 8) provided herein to a subject having gliobastoma multiforme.

In another embodiment, provided herein are methods for improving the Eastern Cooperative Oncology Group Performance Status (ECOG) of a subject comprising administering an effective amount of the solid form of Compound 1 (e.g., Form 1, Form 2, Form 3, Form 4, Form 5, Form 6, Form 7 or Form 8) provided herein to a subject having a tumor, such as an advanced solid tumor.

In another embodiment, provided herein are methods for inducing a therapeutic response assessed by Positron Emission Tomography (PET) outcome of a subject comprising administering an effective amount of the solid form of Compound 1 (e.g., Form 1, Form 2, Form 3, Form 4, Form 5, Form 6, Form 7 or Form 8) provided herein to a subject having a tumor, such as an advanced solid tumor. In certain embodiments, provided herein are methods for treating a solid tumor, such as an advanced solid tumor, the methods comprising administering an effective amount of a TOR kinase inhibitor to a patient having a solid tumor, such as an advanced solid tumor, wherein the treatment results in a reduction in tumor metabolic activity, for example, as measured by PET imaging.

In another embodiment, provided herein are methods for inducing a therapeutic response assessed by a reduction in carcinoid syndrome-related symptoms, such as diarrhea and/or flushing, and/or a reduction in endocrine hormone markers, such as chromogranin, gastrin, serotonin, and/or glucagon.

In one embodiment, provided herein are methods for inhibiting phosphorylation of S6RP, 4E-BP1 and/or AKT in a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided herein to said subject. In some such embodiments, the inhibition of phosphorylation is assessed in a biological sample of the subject, such as in circulating blood and/or tumor cells, skin biopsies and/or tumor biopsies or aspirate. In such embodiments, the amount of inhibition of phosphorylation is assessed by comparison of the amount of phospho-S6RP, 4E-BP1 and/or AKT before and after administration of the solid form of Compound 1 (e.g., Form 1, Form 2, Form 3, Form 4, Form 5, Form 6, Form 7 or Form 8) provided herein. In certain embodiments, provided herein are methods for measuring inhibition of phosphorylation of S6RP, 4E-BP1 or AKT in a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided herein to said subject, measuring the amount of phosphorylated S6RP, 4E-BP1 and/or AKT in said subject, and comparing said amount of phosphorylated S6RP, 4E-BP1 and/or AKT to that of said subject prior to administration of an effective amount of the solid form of Compound 1 (e.g., Form 1, Form 2, Form 3, Form 4, Form 5, Form 6, Form 7 or Form 8) provided herein. In some embodiments, the inhibition of phosphorylation of S6RP, 4E-BP1 and/or AKT is assessed in B-cells, T-cells and/or monocytes.

In certain embodiments, provided herein are methods for inhibiting phosphorylation of S6RP, 4E-BP1 and/or AKT in a biological sample of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided herein to said subject and comparing the amount of phosphorylated S6RP, 4E-BP1 and/or AKT in a biological sample of a subject obtained prior to and after administration of said solid form of Compound 1 (e.g., Form 1, Form 2, Form 3, Form 4, Form 5, Form 6, Form 7 or Form 8) provided herein, wherein less phosphorylated S6RP, 4E-BP1 and/or AKT in said biological sample obtained after administration of said solid form of Compound 1 (e.g., Form 1, Form 2, Form 3, Form 4, Form 5, Form 6, Form 7 or Form 8) provided herein relative to the amount of phosphorylated S6RP, 4E-BP 1 and/or AKT in said biological sample obtained prior to administration of said solid form of Compound 1 (e.g., Form 1, Form 2, Form 3, Form 4, Form 5, Form 6, Form 7 or Form 8) or pharmaceutical composition provided herein indicates inhibition. In some embodiments, the inhibition of phosphorylation of S6RP, 4E-BP1 and/or AKT is assessed in B-cells, T-cells and/or monocytes.

In one embodiment, provided herein are methods for inhibiting DNA-dependent protein kinase (DNA-PK) activity in a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided herein to said subject. In some embodiments, DNA-PK inhibition is assessed in the skin of the subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, in one example in a UV light-irradiated skin sample of said subject. In another embodiment, DNA-PK inhibition is assessed in a tumor biopsy or aspirate of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma. In one embodiment, inhibition is assessed by measuring the amount of phosphorylated DNA-PK S2056 (also known as pDNA-PK S2056) before and after administration of the solid form of Compound 1 (e.g., Form 1, Form 2, Form 3, Form 4, Form 5, Form 6, Form 7 or Form 8) provided herein. In certain embodiments, provided herein are methods for measuring inhibition of phosphorylation of DNA-PK S2056 in a skin sample of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided herein to said subject, measuring the amount of phosphorylated DNA-PK S2056 present in the skin sample and comparing said amount of phosphorylated DNA-PK S2056 to that in a skin sample from said subject prior to administration of an effective amount of the solid form of Compound 1 (e.g., Form 1, Form 2, Form 3, Form 4, Form 5, Form 6, Form 7 or Form 8) provided herein. In one embodiment, the skin sample is irradiated with UV light.

In certain embodiments, provided herein are methods for inhibiting DNA-dependent protein kinase (DNA-PK) activity in a skin sample of a subject having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, comprising administering an effective amount of the solid form of Compound 1 (e.g., Form 1, Form 2, Form 3, Form 4, Form 5, Form 6, Form 7 or Form 8) provided here into said subject and comparing the amount of phosphorylated DNA-PK in a biological sample of a subject obtained prior to and after administration of said solid form of Compound 1 (e.g., Form 1, Form 2, Form 3, Form 4, Form 5, Form 6, Form 7 or Form 8) provided herein, wherein less phosphorylated DNA-PK in said biological sample obtained after administration of said solid form of Compound 1 (e.g., Form 1, Form 2, Form 3, Form 4, Form 5, Form 6, Form 7 or Form 8) provided herein relative to the amount of phosphorylated DNA-PK in said biological sample obtained prior to administration of said solid form of Compound 1 (e.g., Form 1, Form 2, Form 3, Form 4, Form 5, Form 6, Form 7 or Form 8) provided herein indicates inhibition.

The solid form of Compound 1 (e.g., Form 1, Form 2, Form 3, Form 4, Form 5, Form 6, Form 7 or Form 8) provided herein can be combined with radiation therapy or surgery. In certain embodiments, the solid form of Compound 1 (e.g., Form 1, Form 2, Form 3, Form 4, Form 5, Form 6, Form 7 or Form 8) provided herein are administered to subject who is undergoing radiation therapy, has previously undergone radiation therapy or will be undergoing radiation therapy. In certain embodiments, the solid form of Compound 1 (e.g., Form 1, Form 2, Form 3, Form 4, Form 5, Form 6, Form 7 or Form 8) provided herein are administered to a subject who has undergone tumor removal surgery (e.g., surgery to remove a GBM tumor).

Further provided herein are methods for treating subjects who have been previously treated for a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma, but are non-responsive to standard therapies, as well as those who have not previously been treated. Further provided herein are methods for treating subjects who have undergone surgery in an attempt to treat the condition at issue, as well as those who have not. Because subjects with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, or paraganglioma), non-Hodgkin lymphoma or multiple myeloma have heterogenous clinical manifestations and varying clinical outcomes, the treatment given to a subject may vary, depending on his/her prognosis.

In certain embodiments, the pharmaceutical compositions provided herein comprising a solid form of Compound 1 can be used for the treatment or prevention of a disease disclosed in U.S. Pat. Appl. Publ. No. 2010/0216781 (see, e.g., paragraphs [0415]-[0437]), the disclosure of which is incorporated herein by reference in its entirety.

In certain embodiments, the pharmacokinetic parameters set forth herein are mean values obtained from multiple subjects.

5.5 Pharmaceutical Compositions

Solid forms of Compound 1 provided herein are useful for the preparation of pharmaceutical compositions, comprising an effective amount of a solid form of Compound 1 and a pharmaceutically acceptable carrier or vehicle. In some embodiments, the pharmaceutical compositions described herein are suitable for oral, parenteral, mucosal, transdermal or topical administration.

In one embodiment, provided herein are pharmaceutical compositions comprising a solid form of Compound 1 and one or more pharmaceutically acceptable excipients or carriers. In one embodiment, the pharmaceutical compositions provided herein comprise Form 1 and one or more pharmaceutically acceptable excipients or carriers. In one embodiment, the pharmaceutical compositions provided herein comprise Form 2 and one or more pharmaceutically acceptable excipients or carriers. In one embodiment, the pharmaceutical compositions provided herein comprise Form 3 and one or more pharmaceutically acceptable excipients or carriers. In one embodiment, the pharmaceutical compositions provided herein comprise Form 4 and one or more pharmaceutically acceptable excipients or carriers. In one embodiment, the pharmaceutical compositions provided herein comprise Form 5 and one or more pharmaceutically acceptable excipients or carriers. In one embodiment, the pharmaceutical compositions provided herein comprise Form 6 and one or more pharmaceutically acceptable excipients or carriers. In one embodiment, the pharmaceutical compositions provided herein comprise Form 7 and one or more pharmaceutically acceptable excipients or carriers. In one embodiment, the pharmaceutical compositions provided herein comprise Form 8 and one or more pharmaceutically acceptable excipients or carriers.

With respect to the pharmaceutical compositions provided herein, each reference to "a solid form of Compound 1" is contemplated as including Form 1, Form 2, Form 3, Form 4, Form 5, Form 6, Form 7, Form 8 and a mixture of solid forms of Compound 1 provided herein.

In one embodiment, the pharmaceutically acceptable excipients and carriers are selected from binders, diluents, disintegrants and lubricants.

In certain embodiments, the binders include, but are not limited to, cellulose (e.g., microcrystalline cellulose, such as AVICEL® PH 101, AVICEL® PH 102 and AVICEL® PH 112) and starch (e.g., pregelatinized starch (STARCH 1500®)). In one embodiment, the binder is cellulose. In another embodiment, the binder is microcrystalline cellulose. In yet another embodiment, the binder is AVICEL® PH 101. In yet another embodiment, the binder is AVICEL® PH 102. In yet another embodiment, the binder is AVICEL® PH 112. In yet another embodiment, the binder is starch. In yet another embodiment, the binder is pregelatinized starch. In still another embodiment, the binder is STARCH 1500®.

In certain embodiments, the diluents include, but are not limited to, lactose (e.g., lactose monohydrate (FAST FLO® 316) and lactose anhydrous), cellulose (e.g., microcrystalline cellulose, such as AVICEL® PH 101, AVICEL® PH 102 and AVICEL® PH 112). In one embodiment, the diluent is lactose. In another embodiment, the diluent is lactose monohydrate. In yet another embodiment, the diluent is FAST FLO® 316. In yet another embodiment, the diluent is lactose anhydrous. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102. In still another embodiment, the diluent is AVICEL® PH 112.

In certain embodiments, the disintegrants include, but are not limited to, starch (e.g., corn starch) and carboxymethyl cellulose (e.g., croscarmellose sodium, such as AC-DI-SOL®). In one embodiment, the disintegrant is starch. In another embodiment, the disintegrant is corn starch. In yet another embodiment, the disintegrant is carboxymethyl cellulose. In yet another embodiment, the disintegrant is croscarmellose sodium. In still another embodiment, the disintegrant is AC-DI-SOL®.

In certain embodiments, the lubricants include, but are not limited to, starch (e.g., corn starch), magnesium stearate, and stearic acid. In one embodiment, the lubricant is starch. In another embodiment, the lubricant is corn starch. In yet another embodiment, the lubricant is magnesium stearate. In still another embodiment, the lubricant is stearic acid.

In another embodiment, the pharmaceutical compositions provided herein comprise a solid form of Compound 1 and one or more pharmaceutically acceptable excipients or carriers, each independently selected from carboxymethyl cellulose, cellulose, lactose, magnesium stearate, starch, and stearic acid.

In another embodiment, the pharmaceutical compositions provided herein comprise a solid form of Compound 1 and one or more pharmaceutically acceptable excipients or carriers, each independently selected from carboxymethyl cellulose, cellulose, lactose, magnesium stearate and starch.

In yet another embodiment, the pharmaceutical compositions provided herein comprise a solid form of Compound 1 and one or more pharmaceutically acceptable excipients or carriers, each independently selected from croscarmellose sodium, microcrystalline cellolose, lactose anhydrous, lactose monohydrate, magnesium stearate, corn starch, pregelatinized starch, and stearic acid.

In yet another embodiment, the pharmaceutical compositions provided herein comprise a solid form of Compound 1 and one or more pharmaceutically acceptable excipients or carriers, each independently selected from croscarmellose sodium, microcrystalline cellolose, lactose anhydrous, lactose monohydrate, magnesium stearate, corn starch and pregelatinized starch.

In certain embodiments, the pharmaceutical compositions provided herein do not comprise stearic acid.

In yet another embodiment, the pharmaceutical compositions provided herein comprise a solid form of Compound 1 and one or more pharmaceutically acceptable excipients or carriers, each independently selected from AC-DI-SOL®, AVICEL PH 1010, AVICEL PH 102®, lactose anhydrous, FAST FLO 316®, magnesium stearate, corn starch, STARCH 1500®, and stearic acid.

In yet another embodiment, the pharmaceutical compositions provided herein comprise a solid form of Compound 1 and one or more pharmaceutically acceptable excipients or carriers, each independently selected from AC-DI-SOL®, AVICEL PH 1010, AVICEL PH 102®, lactose anhydrous, FAST FLO 316®, magnesium stearate, corn starch and STARCH 1500®.

In one embodiment, the pharmaceutical compositions provided herein comprise a solid form of Compound 1, a diluent(s)/binder(s), a disintegrant(s), and a lubricant(s).

In one embodiment, the pharmaceutical compositions provided herein comprise a solid form of Compound 1, stearic acid and lactose monohydrate.

In one embodiment, the pharmaceutical compositions provided herein comprise a solid form of Compound 1 and lactose monohydrate.

In one embodiment, the pharmaceutical compositions provided herein comprise a solid form of Compound 1, stearic acid, lactose monohydrate and microcyrstalline cellulose.

In one embodiment, the pharmaceutical compositions provided herein comprise a solid form of Compound 1, lactose monohydrate and microcyrstalline cellulose.

In another embodiment, the pharmaceutical compositions provided herein comprise a solid form of Compound 1, lactose monohydrate, microcrystalline cellulose, carboxymethyl cellulose, and magnesium stearate.

In another embodiment, the pharmaceutical compositions provided herein comprise a solid form of Compound 1, lactose monohydrate, microcrystalline cellulose, croscarmellose sodium, stearic acid and magnesium stearate.

In another embodiment, the pharmaceutical compositions provided herein comprise a solid form of Compound 1, lactose monohydrate, microcrystalline cellulose, croscarmellose sodium and magnesium stearate.

In still another embodiment, the pharmaceutical compositions provided herein comprise a solid form of Compound 1, FAST FLO 316®, AVICEL PH 102®, AC-DI-SOL®, stearic acid and magnesium stearate.

In still another embodiment, the pharmaceutical compositions provided herein comprise a solid form of Compound 1, FAST FLO 316®, AVICEL PH 112®, AC-DI-SOL® and magnesium stearate.

In one embodiment, the pharmaceutical compositions provided herein comprise about 10-20% by weight of a solid form of Compound 1, about 70-90% by weight of diluent(s)/binder(s), about 1-5% by weight of disintegrant(s), and about 0.1-2% by weight of lubricant(s).

In one embodiment, the pharmaceutical compositions provided herein comprise about 15% by weight of a solid form of Compound 1, about 80% by weight of diluent(s)/binder(s), about 3% by weight of disintegrant(s), and about 1.4% by weight of lubricant(s).

In another embodiment, the pharmaceutical compositions provided herein comprise about 10-20% by weight of a solid form of Compound 1, about 30-60% by weight of lactose, about 20-40% by weight of microcrystalline cellulose, about 1-5% by weight of carboxymethyl cellulose, about 0.1-2% by weight of stearic acid and about 0.5-3% by weight of magnesium stearate.

In another embodiment, the pharmaceutical compositions provided herein comprise about 10-20% by weight of a solid form of Compound 1, about 30-60% by weight of lactose, about 20-40% by weight of microcrystalline cellulose, about 1-5% by weight of carboxymethyl cellulose and about 0.5-3% by weight of magnesium stearate.

In another embodiment, the pharmaceutical compositions provided herein comprise about 15% by weight of a solid form of Compound 1, about 49% by weight of lactose, about 31% by weight of microcrystalline cellulose, about 3% by weight of carboxymethyl cellulose, about 0.4% by weight of stearic acid and about 1% by weight of magnesium stearate.

In another embodiment, the pharmaceutical compositions provided herein comprise about 15% by weight of a solid form of Compound 1, about 49% by weight of lactose, about 31% by weight of microcrystalline cellulose, about 3% by weight of carboxymethyl cellulose and about 1% by weight of magnesium stearate.

In yet another embodiment, the pharmaceutical compositions provided herein comprise about 10-20% by weight of a solid form of Compound 1, about 30-60% by weight of lactose monohydrate, about 20-40% by weight of microcrystalline cellulose, about 1-5% by weight of croscarmellose sodium, about 0.1-2% by weight stearic acid and about 0.5-3% by weight of magnesium stearate.

In yet another embodiment, the pharmaceutical compositions provided herein comprise about 10-20% by weight of a solid form of Compound 1, about 30-60% by weight of lactose monohydrate, about 20-40% by weight of microcrystalline cellulose, about 1-5% by weight of croscarmellose sodium and about 0.5-3% by weight of magnesium stearate.

In yet another embodiment, the pharmaceutical compositions provided herein comprise about 15% by weight of a solid form of Compound 1, about 49% by weight of lactose monohydrate, about 31% by weight of microcrystalline cellulose, about 3% by weight of croscarmellose sodium, about 0.4% by weight of stearic acid and about 1% by weight of magnesium stearate.

In yet another embodiment, the pharmaceutical compositions provided herein comprise about 15% by weight of a solid form of Compound 1, about 49% by weight of lactose monohydrate, about 31% by weight of microcrystalline cellulose, about 3% by weight of croscarmellose sodium and about 1% by weight of magnesium stearate.

In still another embodiment, the pharmaceutical compositions provided herein comprise about 10-20% by weight of a solid form of Compound 1, about 30-60% by weight of FAST FLO 316®, about 20-40% by weight of AVICEL PH 102®, about 1-5% by weight of AC-DI-SOL®, about 0.1-2% by weight of stearic acid and about 0.5-3% by weight of magnesium stearate.

In still another embodiment, the pharmaceutical compositions provided herein comprise about 10-20% by weight of a solid form of Compound 1, about 30-60% by weight of FAST FLO 316®, about 20-40% by weight of AVICEL PH 112®, about 1-5% by weight of AC-DI-SOL® and about 0.5-3% by weight of magnesium stearate.

In still another embodiment, the pharmaceutical compositions provided herein comprise about 15% by weight of a solid form of Compound 1, about 49% by weight of FAST FLO 316®, about 31% by weight of AVICEL PH 102®, about 3% by weight of AC-DI-SOL®, about 0.4% by weight of stearic acid and about 1% by weight of magnesium stearate.

In still another embodiment, the pharmaceutical compositions provided herein comprise about 15% by weight of a solid form of Compound 1, about 49% by weight of FAST FLO 316®, about 31% by weight of AVICEL PH 112®, about 3% by weight of AC-DI-SOL® and about 1% by weight of magnesium stearate.

In one embodiment, the pharmaceutical compositions provided herein comprise a solid form of Compound 1, lactose, starch, carboxymethyl cellulose, stearic acid and magnesium stearate.

In one embodiment, the pharmaceutical compositions provided herein comprise a solid form of Compound 1, lactose, starch, carboxymethyl cellulose and magnesium stearate.

In another embodiment, the pharmaceutical compositions provided herein comprise a solid form of Compound 1, lactose monohydrate, pregelatinized starch, croscarmellose sodium, stearic acid and magnesium stearate.

In another embodiment, the pharmaceutical compositions provided herein comprise a solid form of Compound 1, lactose monohydrate, pregelatinized starch, croscarmellose sodium and magnesium stearate.

In still another embodiment, the pharmaceutical compositions provided herein comprise a solid form of Compound 1, FAST FLO 316®, STARCH 1500®, AC-DI-SOL®, stearic acid and magnesium stearate.

In still another embodiment, the pharmaceutical compositions provided herein comprise a solid form of Compound 1, FAST FLO 316®, STARCH 1500®, AC-DI-SOL® and magnesium stearate.

In one embodiment, the pharmaceutical compositions provided herein comprise about 15% by weight of a solid form of Compound 1, from about 55% to about 80% by weight of diluent(s)/binder(s), from about 20% to about 30% by weight of disintegrant(s), and about 1% by weight of lubricant(s).

In another embodiment, the pharmaceutical compositions provided herein comprise about 15% by weight of a solid form of Compound 1, about 55% by weight of lactose, about 25% by weight of starch, about 3% by weight of carboxymethyl cellulose, about 0.4% by weight of stearic acid and about 1% by weight of magnesium stearate.

In another embodiment, the pharmaceutical compositions provided herein comprise about 15% by weight of a solid form of Compound 1, about 55% by weight of lactose, about 25% by weight of starch, about 3% by weight of carboxymethyl cellulose and about 1% by weight of magnesium stearate.

In yet another embodiment, the pharmaceutical compositions provided herein comprise about 15% by weight of a solid form of Compound 1, about 55% by weight of lactose monohydrate, about 25% by weight of pregelatinized starch, about 3% by weight of croscarmellose sodium, about 0.4% by weight of stearic acid and about 1% by weight of magnesium stearate.

In yet another embodiment, the pharmaceutical compositions provided herein comprise about 15% by weight of a solid form of Compound 1, about 55% by weight of lactose monohydrate, about 25% by weight of pregelatinized starch, about 3% by weight of croscarmellose sodium and about 1% by weight of magnesium stearate.

In still another embodiment, the pharmaceutical compositions provided herein comprise about 15% by weight of a solid form of Compound 1, about 55% by weight of FAST FLO 316®, about 25% by weight of STARCH 1500®, about 3% by weight of AC-DI-SOL®, about 0.4% by weight of stearic acid and about 1% by weight of magnesium stearate.

In still another embodiment, the pharmaceutical compositions provided herein comprise about 15% by weight of a solid form of Compound 1, about 55% by weight of FAST FLO 316®, about 25% by weight of STARCH 1500®, about 3% by weight of AC-DI-SOL® and about 1% by weight of magnesium stearate.

In one embodiment, the pharmaceutical compositions provided herein comprise a solid form of Compound 1, lactose, microcrystalline cellulose, carboxymethyl cellulose, stearic acid and magnesium stearate.

In one embodiment, the pharmaceutical compositions provided herein comprise a solid form of Compound 1, lactose, microcrystalline cellulose, carboxymethyl cellulose and magnesium stearate.

In another embodiment, the pharmaceutical compositions provided herein comprise a solid form of Compound 1, lactose monohydrate, microcrystalline cellulose, croscarmellose sodium, stearic acid and magnesium stearate.

In another embodiment, the pharmaceutical compositions provided herein comprise a solid form of Compound 1, lactose monohydrate, microcrystalline cellulose, croscarmellose sodium and magnesium stearate.

In still another embodiment, the pharmaceutical compositions provided herein comprise a solid form of Compound 1, FAST FLO 316®, AVICEL PH 102®, AC-DI-SOL®, about 0.4% by weight of stearic acid and magnesium stearate.

In still another embodiment, the pharmaceutical compositions provided herein comprise a solid form of Compound 1, FAST FLO 316®, AVICEL PH 112®, AC-DI-SOL® and magnesium stearate.

In one embodiment, the pharmaceutical compositions provided herein comprise about 15% by weight of a solid form of Compound 1, about 80% by weight of diluent(s)/binder(s), about 3% by weight of disintegrant(s), and about 1% by weight of lubricant(s).

In another embodiment, the pharmaceutical compositions provided herein comprise about 15% by weight of a solid form of Compound 1, about 50% by weight of lactose, about 30% by weight of microcrystalline cellulose, about 3% by weight of carboxymethyl cellulose, about 0.4% by weight of stearic acid and about 1% by weight of magnesium stearate.

In another embodiment, the pharmaceutical compositions provided herein comprise about 15% by weight of a solid form of Compound 1, about 50% by weight of lactose, about 30% by weight of microcrystalline cellulose, about 3% by weight of carboxymethyl cellulose and about 1% by weight of magnesium stearate.

In yet another embodiment, the pharmaceutical compositions provided herein comprise about 15% by weight of a solid form of Compound 1, about 50% by weight of lactose monohydrate, about 30% by weight of microcrystalline cellulose, about 3% by weight of croscarmellose sodium, about 0.4% by weight of stearic acid and about 1% by weight of magnesium stearate.

In yet another embodiment, the pharmaceutical compositions provided herein comprise about 15% by weight of a solid form of Compound 1, about 50% by weight of lactose monohydrate, about 30% by weight of microcrystalline cellulose, about 3% by weight of croscarmellose sodium and about 1% by weight of magnesium stearate.

In still another embodiment, the pharmaceutical compositions provided herein comprise about 15% by weight of a solid form of Compound 1, about 50% by weight of FAST FLO 316®, about 30% by weight of AVICEL PH 102®, about 3% by weight of AC-DI-SOL®, about 0.4% by weight of stearic acid and about 1% by weight of magnesium stearate.

In still another embodiment, the pharmaceutical compositions provided herein comprise about 15% by weight of a solid form of Compound 1, about 50% by weight of FAST FLO 316®, about 30% by weight of AVICEL PH 112®, about 3% by weight of AC-DI-SOL® and about 1% by weight of magnesium stearate.

In one embodiment, the pharmaceutical compositions provided herein comprise a solid form of Compound 1, lactose, microcrystalline cellulose, corn starch, carboxymethyl cellulose, stearic acid and magnesium stearate.

In one embodiment, the pharmaceutical compositions provided herein comprise a solid form of Compound 1, lactose, microcrystalline cellulose, corn starch, carboxymethyl cellulose and magnesium stearate.

In another embodiment, the pharmaceutical compositions provided herein comprise a solid form of Compound 1, lactose monohydrate, microcrystalline cellulose, corn starch, croscarmellose sodium, stearic acid and magnesium stearate.

In another embodiment, the pharmaceutical compositions provided herein comprise a solid form of Compound 1, lactose monohydrate, microcrystalline cellulose, corn starch, croscarmellose sodium and magnesium stearate.

In still another embodiment, the pharmaceutical compositions provided herein comprise a solid form of Compound 1, FAST FLO 316®, AVICEL PH 102®, corn starch, AC-DI-SOL®, stearic acid and magnesium stearate.

In still another embodiment, the pharmaceutical compositions provided herein comprise a solid form of Compound 1, FAST FLO 316®, AVICEL PH 102®, corn starch, AC-DI-SOL® and magnesium stearate.

In one embodiment, the pharmaceutical compositions provided herein comprise about 15% by weight of a solid form of Compound 1, from about 85% to about 90% by weight of diluent(s)/binder(s), from about 1% to about 10% by weight of disintegrant(s), and from about 1% to about 6% by weight of lubricants.

In another embodiment, the pharmaceutical compositions provided herein comprise about 15% by weight of a solid form of Compound 1, about 45% by weight of lactose, about 30% by weight of microcrystalline cellulose, about 3% by weight of corn starch, about 3% by weight of carboxymethyl cellulose, about 0.4% by weight of stearic acid and about 1% by weight of magnesium stearate.

In another embodiment, the pharmaceutical compositions provided herein comprise about 15% by weight of a solid form of Compound 1, about 45% by weight of lactose, about 30% by weight of microcrystalline cellulose, about 3% by weight of corn starch, about 3% by weight of carboxymethyl cellulose and about 1% by weight of magnesium stearate.

In yet another embodiment, the pharmaceutical compositions provided herein comprise about 15% by weight of a solid form of Compound 1, about 88% by weight of lactose, about 25% by weight of microcrystalline cellulose, about 4% by weight of corn starch, about 4% by weight of carboxymethyl cellulose, about 0.4% by weight of stearic acid and about 1.5% by weight of magnesium stearate.

In yet another embodiment, the pharmaceutical compositions provided herein comprise about 15% by weight of a solid form of Compound 1, about 88% by weight of lactose, about 25% by weight of microcrystalline cellulose, about 4% by weight of corn starch, about 4% by weight of carboxymethyl cellulose and about 1.5% by weight of magnesium stearate.

In yet another embodiment, the pharmaceutical compositions provided herein comprise about 15% by weight of a solid form of Compound 1, about 45% by weight of lactose monohydrate, about 30% by weight of microcrystalline cellulose, about 3% by weight of corn starch, about 3% by weight of croscarmellose sodium, about 0.4% by weight of stearic acid and about 1% by weight of magnesium stearate.

In yet another embodiment, the pharmaceutical compositions provided herein comprise about 15% by weight of a solid form of Compound 1, about 45% by weight of lactose monohydrate, about 30% by weight of microcrystalline cellulose, about 3% by weight of corn starch, about 3% by weight of croscarmellose sodium and about 1% by weight of magnesium stearate.

In yet another embodiment, the pharmaceutical compositions provided herein comprise about 15% by weight of a solid form of Compound 1, about 88% by weight of lactose monohydrate, about 25% by weight of microcrystalline cellulose, about 4% by weight of corn starch, about 4% by weight of croscarmellose sodium, about 0.4% by weight of stearic acid and about 1.5% by weight of magnesium stearate.

In yet another embodiment, the pharmaceutical compositions provided herein comprise about 15% by weight of a solid form of Compound 1, about 88% by weight of lactose monohydrate, about 25% by weight of microcrystalline cellulose, about 4% by weight of corn starch, about 4% by weight of croscarmellose sodium and about 1.5% by weight of magnesium stearate.

In yet another embodiment, the pharmaceutical compositions provided herein comprise about 15% by weight of a solid form of Compound 1, about 45% by weight of FAST FLO 316®, about 30% by weight of AVICEL PH 102®, about 3% by weight of corn starch, about 3% by weight of AC-DI-SOL®, about 0.4% by weight of stearic acid and about 1% by weight of magnesium stearate.

In yet another embodiment, the pharmaceutical compositions provided herein comprise about 15% by weight of a solid form of Compound 1, about 45% by weight of FAST FLO 316®, about 30% by weight of AVICEL PH 102®, about 3% by weight of corn starch, about 3% by weight of AC-DI-SOL® and about 1% by weight of magnesium stearate.

In still another embodiment, the pharmaceutical compositions provided herein comprise about 15% by weight of a solid form of Compound 1, about 88% by weight of FAST FLO 316®, about 25% by weight of AVICEL PH 102®, about 4% by weight of corn starch, about 4% by weight of AC-DI-SOL®, about 0.4% by weight of stearic acid and about 1.5% by weight of magnesium stearate.

In still another embodiment, the pharmaceutical compositions provided herein comprise about 15% by weight of a solid form of Compound 1, about 88% by weight of FAST FLO 316®, about 25% by weight of AVICEL PH 102®, about 4% by weight of corn starch, about 4% by weight of AC-DI-SOL® and about 1.5% by weight of magnesium stearate.

In one embodiment, the pharmaceutical compositions provided herein comprise a solid form of Compound 1, lactose, microcrystalline cellulose, corn starch, carboxymethyl cellulose, stearic acid, and magnesium stearate.

In one embodiment, the pharmaceutical compositions provided herein comprise a solid form of Compound 1, lactose, microcrystalline cellulose, corn starch, carboxymethyl cellulose and magnesium stearate.

In one embodiment, the pharmaceutical compositions provided herein comprise about 5% by weight of a solid form of Compound 1, about 90% by weight of diluent(s)/binder(s), from about 3% to about 6% by weight of disintegrant(s), and from about 1.5% to about 5% by weight of lubricants.

In another embodiment, the pharmaceutical compositions provided herein comprise about 5% by weight of a solid form of Compound 1, about 60% by weight of lactose, about 30% by weight of microcrystalline cellulose, about 3% by weight of corn starch, about 3% by weight of carboxymethyl cellulose, about 0.5% by weight of stearic acid, and about 1% by weight of magnesium stearate.

In another embodiment, the pharmaceutical compositions provided herein comprise about 5% by weight of a solid form of Compound 1, about 60% by weight of lactose, about 30% by weight of microcrystalline cellulose, about 3% by weight of corn starch, about 3% by weight of carboxymethyl cellulose and about 1% by weight of magnesium stearate.

In yet another embodiment, the pharmaceutical compositions provided herein comprise about 5% by weight of a solid form of Compound 1, about 60% by weight of lactose monohydrate, about 30% by weight of microcrystalline cellulose, about 3% by weight of corn starch, about 3% by weight of croscarmellose sodium, about 0.5% by weight of stearic acid, and about 1% by weight of magnesium stearate.

In yet another embodiment, the pharmaceutical compositions provided herein comprise about 5% by weight of a solid form of Compound 1, about 60% by weight of lactose monohydrate, about 30% by weight of microcrystalline cellulose, about 3% by weight of corn starch, about 3% by weight of croscarmellose sodium and about 1% by weight of magnesium stearate.

In still another embodiment, the pharmaceutical compositions provided herein comprise about 5% by weight of a solid form of Compound 1, about 60% by weight of FAST FLO 316®, about 30% by weight of AVICEL PH 102®, about 3% by weight of corn starch, about 3% by weight of AC-DI-SOL®, about 0.5% by weight of stearic acid, and about 1% by weight of magnesium stearate.

In still another embodiment, the pharmaceutical compositions provided herein comprise about 5% by weight of a solid form of Compound 1, about 60% by weight of FAST FLO 316®, about 30% by weight of AVICEL PH 102®, about 3% by weight of corn starch, about 3% by weight of AC-DI-SOL® and about 1% by weight of magnesium stearate.

In one embodiment, the pharmaceutical compositions provided herein comprise a solid form of Compound 1, lactose, microcrystalline cellulose, carboxymethyl cellulose, stearic acid, and magnesium stearate.

In one embodiment, the pharmaceutical compositions provided herein comprise a solid form of Compound 1, lactose, microcrystalline cellulose, carboxymethyl cellulose and magnesium stearate.

In another embodiment, the pharmaceutical compositions provided herein comprise a solid form of Compound 1, lactose monohydrate, microcrystalline cellulose, croscarmellose sodium, stearic acid, and magnesium stearate.

In another embodiment, the pharmaceutical compositions provided herein comprise a solid form of Compound 1, lactose monohydrate, microcrystalline cellulose, croscarmellose sodium and magnesium stearate.

In still another embodiment, the pharmaceutical compositions provided herein comprise a solid form of Compound 1, FAST FLO 316®, AVICEL PH 102®, AC-DI-SOL®, stearic acid, and magnesium stearate.

In still another embodiment, the pharmaceutical compositions provided herein comprise a solid form of Compound 1, FAST FLO 316®, AVICEL PH 102®, AC-DI-SOL® and magnesium stearate.

In one embodiment, the pharmaceutical compositions provided herein comprise about 12% by weight of a solid form of Compound 1, from about 80% to about 85% by weight of diluent(s)/binder(s), about 3% by weight of disintegrant(s), and about 1.5% by weight of lubricant(s).

In another embodiment, the pharmaceutical compositions provided herein comprise about 12% by weight of a solid form of Compound 1, about 52.5% by weight of lactose, about 30% by weight of microcrystalline cellulose, about 3% by weight of carboxymethyl cellulose, about 0.5% by weight of stearic acid, and about 1% by weight of magnesium stearate.

In another embodiment, the pharmaceutical compositions provided herein comprise about 12% by weight of a solid form of Compound 1, about 52.5% by weight of lactose, about 30% by weight of microcrystalline cellulose, about 3% by weight of carboxymethyl cellulose and about 1% by weight of magnesium stearate.

In yet another embodiment, the pharmaceutical compositions provided herein comprise about 12% by weight of a solid form of Compound 1, about 52.5% by weight of lactose monohydrate, about 30% by weight of microcrystalline cellulose, about 3% by weight of croscarmellose sodium, about 0.5% by weight of stearic acid, and about 1% by weight of magnesium stearate.

In yet another embodiment, the pharmaceutical compositions provided herein comprise about 12% by weight of a solid form of Compound 1, about 52.5% by weight of lactose monohydrate, about 30% by weight of microcrystalline cellulose, about 3% by weight of croscarmellose sodium and about 1% by weight of magnesium stearate.

In still another embodiment, the pharmaceutical compositions provided herein comprise about 12% by weight of a solid form of Compound 1, about 52.5% by weight of FAST FLO 316®, about 30% by weight of AVICEL PH 102®, about 3% by weight of AC-DI-SOL®, about 0.5% by weight of stearic acid, and about 1% by weight of magnesium stearate.

In still another embodiment, the pharmaceutical compositions provided herein comprise about 12% by weight of a solid form of Compound 1, about 52.5% by weight of FAST FLO 316®, about 30% by weight of AVICEL PH 102®, about 3% by weight of AC-DI-SOL® and about 1% by weight of magnesium stearate.

In one embodiment, the pharmaceutical compositions provided herein comprise about 12% by weight of a solid form of Compound 1, about 80% by weight of diluent(s)/binder(s), about 3% by weight of disintegrant(s), and about 4% by weight of lubricant(s).

In another embodiment, the pharmaceutical compositions provided herein comprise about 12% by weight of a solid form of Compound 1, about 63% by weight of lactose, about 18% by weight of microcrystalline cellulose, about 3% by weight of carboxymethyl cellulose, about 3% by weight of stearic acid, and about 1% by weight of magnesium stearate.

In another embodiment, the pharmaceutical compositions provided herein comprise about 12% by weight of a solid form of Compound 1, about 63% by weight of lactose, about 18% by weight of microcrystalline cellulose, about 3% by weight of carboxymethyl cellulose and about 1% by weight of magnesium stearate.

In yet another embodiment, the pharmaceutical compositions provided herein comprise about 12% by weight of a solid form of Compound 1, about 63% by weight of lactose monohydrate, about 18% by weight of microcrystalline cellulose, about 3% by weight of croscarmellose sodium, about 3% by weight of stearic acid, and about 1% by weight of magnesium stearate.

In yet another embodiment, the pharmaceutical compositions provided herein comprise about 12% by weight of a solid form of Compound 1, about 63% by weight of lactose monohydrate, about 18% by weight of microcrystalline cellulose, about 3% by weight of croscarmellose sodium and about 1% by weight of magnesium stearate.

In still another embodiment, the pharmaceutical compositions provided herein comprise about 12% by weight of a solid form of Compound 1, about 63% by weight of FAST FLO 316®, about 18% by weight of AVICEL PH 102®, about 3% by weight of AC-DI-SOL®, about 3% by weight of stearic acid, and about 1% by weight of magnesium stearate.

In still another embodiment, the pharmaceutical compositions provided herein comprise about 12% by weight of a solid form of Compound 1, about 63% by weight of FAST FLO 316®, about 18% by weight of AVICEL PH 102®, about 3% by weight of AC-DI-SOL® and about 1% by weight of magnesium stearate.

In one embodiment, the pharmaceutical compositions provided herein comprise about 15% by weight of a solid form of Compound 1, about 80% by weight of a diluent/binder, about 3% by weight of a disintegrant, and about 1.5% by weight of lubricants.

In another embodiment, the pharmaceutical compositions provided herein comprise about 15% by weight of a solid form of Compound 1, about 50% by weight of lactose, about 30% by weight of microcrystalline cellulose, about 3% by weight of carboxymethyl cellulose, about 0.5% by weight of stearic acid, and about 1% by weight of magnesium stearate.

In another embodiment, the pharmaceutical compositions provided herein comprise about 15% by weight of a solid form of Compound 1, about 50% by weight of lactose, about 30% by weight of microcrystalline cellulose, about 3% by weight of carboxymethyl cellulose and about 1% by weight of magnesium stearate.

In yet another embodiment, the pharmaceutical compositions provided herein comprise about 15% by weight of a solid form of Compound 1, about 50% by weight of lactose monohydrate, about 30% by weight of microcrystalline cellulose, about 3% by weight of croscarmellose sodium, about 0.5% by weight of stearic acid, and about 1% by weight of magnesium stearate.

In yet another embodiment, the pharmaceutical compositions provided herein comprise about 15% by weight of a solid form of Compound 1, about 50% by weight of lactose monohydrate, about 30% by weight of microcrystalline cellulose, about 3% by weight of croscarmellose sodium and about 1% by weight of magnesium stearate.

In still another embodiment, the pharmaceutical compositions provided herein comprise about 15% by weight of a solid form of Compound 1, about 50% by weight of FAST FLO 316®, about 30% by weight of AVICEL PH 102®, about 3% by weight of AC-DI-SOL®, about 0.5% by weight of stearic acid, and about 1% by weight of magnesium stearate.

In still another embodiment, the pharmaceutical compositions provided herein comprise about 15% by weight of a solid form of Compound 1, about 50% by weight of FAST FLO 316®, about 30% by weight of AVICEL PH 102®, about 3% by weight of AC-DI-SOL® and about 1% by weight of magnesium stearate.

In one embodiment, the pharmaceutical compositions provided herein comprise about 17% by weight of Form 1 of a solid form of Compound 1, about 80% by weight of dilent(s)/binder(s), about 3% by weight of disintegrant(s), and about 1% by weight of lubricant(s).

In another embodiment, the pharmaceutical compositions provided herein comprise about 17% by weight of a solid form of Compound 1, about 50% by weight of lactose, about 30% by weight of microcrystalline cellulose, about 3% by weight of carboxymethyl cellulose, and about 1% by weight of magnesium stearate.

In yet another embodiment, the pharmaceutical compositions provided herein comprise about 17% by weight of a solid form of Compound 1, about 50% by weight of lactose monohydrate, about 30% by weight of microcrystalline cellulose, about 3% by weight of croscarmellose sodium, and about 1% by weight of magnesium stearate.

In still another embodiment, the pharmaceutical compositions provided herein comprise about 17% by weight of a solid form of Compound 1, about 50% by weight of FAST FLO 316®, about 30% by weight of AVICEL PH 1010, about 3% by weight of AC-DI-SOL®, and about 1% by weight of magnesium stearate.

In one embodiment, the pharmaceutical compositions provided herein comprise about 17% by weight of a solid form of Compound 1, from about 55% to about 80% by weight of dilent(s)/binder(s), from about 20% to about 30% by weight of disintegrant(s), and about 1% by weight of lubricant(s).

In another embodiment, the pharmaceutical compositions provided herein comprise about 17% by weight of a solid form of Compound 1, about 55% by weight of lactose, about 25% by weight of starch, about 3% by weight of carboxymethyl cellulose, and about 1% by weight of magnesium stearate.

In yet another embodiment, the pharmaceutical compositions provided herein comprise about 17% by weight of a solid form of Compound 1, about 55% by weight of lactose monohydrate, about 25% by weight of pregelatinized starch, about 3% by weight of croscarmellose sodium, and about 1% by weight of magnesium stearate.

In still another embodiment, the pharmaceutical compositions provided herein comprise about 17% by weight of a solid form of Compound 1, about 55% by weight of FAST FLO 316®, about 25% by weight of STARCH 1500®, about 3% by weight of AC-DI-SOL®, and about 1% by weight of magnesium stearate.

In one embodiment, the pharmaceutical compositions provided herein comprise about 17% by weight of a solid form of Compound 1, about 80% by weight of dilent(s)/binder(s), about 3% by weight of disintegrant(s), and about 1% by weight of lubricant(s).

In another embodiment, the pharmaceutical compositions provided herein comprise about 17% by weight of a solid form of Compound 1, about 50% by weight of lactose, about 30% by weight of microcrystalline cellulose, about 3% by weight of carboxymethyl cellulose, and about 1% by weight of magnesium stearate.

In yet another embodiment, the pharmaceutical compositions provided herein comprise about 17% by weight of a solid form of Compound 1, about 50% by weight of lactose monohydrate, about 30% by weight of microcrystalline cellulose, about 3% by weight of croscarmellose sodium, and about 1% by weight of magnesium stearate.

In still another embodiment, the pharmaceutical compositions provided herein comprise about 17% by weight of a solid form of Compound 1, about 50% by weight of FAST FLO 316®, about 30% by weight of AVICEL PH 102®, about 3% by weight of AC-DI-SOL®, and about 1% by weight of magnesium stearate.

In one embodiment, the pharmaceutical compositions provided herein comprise about 17% by weight of a solid form of Compound 1, from about 85% to about 90% by weight of dilent(s)/binder(s), from about 3% to about 9% by weight of disintegrant(s), and from about 1% to about 6% by weight of lubricants.

In another embodiment, the pharmaceutical compositions provided herein comprise about 17% by weight of a solid form of Compound 1, about 45% by weight of lactose, about 30% by weight of microcrystalline cellulose, about 3% by weight of corn starch, about 3% by weight of carboxymethyl cellulose, and about 1% by weight of magnesium stearate.

In yet another embodiment, the pharmaceutical compositions provided herein comprise about 17% by weight of a solid form of Compound 1, about 88% by weight of lactose, about 25% by weight of microcrystalline cellulose, about 4% by weight of corn starch, about 4% by weight of carboxymethyl cellulose, and about 1.5% by weight of magnesium stearate.

In yet another embodiment, the pharmaceutical compositions provided herein comprise about 17% by weight of a solid form of Compound 1, about 45% by weight of lactose monohydrate, about 30% by weight of microcrystalline cellulose, about 3% by weight of corn starch, about 3% by weight of croscarmellose sodium, and about 1% by weight of magnesium stearate.

In yet another embodiment, the pharmaceutical compositions provided herein comprise about 17% by weight of a solid form of Compound 1, about 88% by weight of lactose monohydrate, about 25% by weight of microcrystalline cellulose, about 4% by weight of corn starch, about 4% by weight of croscarmellose sodium, and about 1.5% by weight of magnesium stearate.

In yet another embodiment, the pharmaceutical compositions provided herein comprise about 17% by weight of a solid form of Compound 1, about 45% by weight of FAST FLO 316®, about 30% by weight of AVICEL PH 102®, about 3% by weight of corn starch, about 3% by weight of AC-DI-SOL®, and about 1% by weight of magnesium stearate.

In still another embodiment, the pharmaceutical compositions provided herein comprise about 17% by weight of a solid form of Compound 1, about 88% by weight of FAST FLO 316®, about 25% by weight of AVICEL PH 102®, about 4% by weight of corn starch, about 4% by weight of AC-DI-SOL®, and about 1.5% by weight of magnesium stearate.

In certain embodiments, provided herein are pharmaceutical compositions comprising a solid form of Compound 1 and stearic acid. In certain embodiments, stearic acid is present in an amount of about 0.1-5%, 0.1 to 1%, or 0.4% by weight. Without being limited by theory, it was found that the addition of stearic acid improved lubrication (reduced sticking) without impacting disintegration and compressability.

In certain embodiments, provided herein are pharmaceutical compositions comprising a solid form of Compound 1 and lactose monohydrate. In certain embodiments, lactose monohydrate is present in an amount of about 40-60%, 45-55%, 49.2% or 49.6% by weight. Without being limited by theory, it was found that lactose monohydrate provided better flowability than lactose anhydrous.

In certain embodiments, provided herein are pharmaceutical compositions comprising a solid form of Compound 1 and AVICEL PH 102®. In certain embodiments, AVICEL PH 102® is present in an amount of about 20-40%, 25-35%, or 31% by weight. Without being limited by theory, it was found that AVICEL PH 102® provided better flowability than AVICEL PH 101®.

In certain embodiments, provided herein are pharmaceutical compositions comprising a solid form of Compound 1 and AVICEL PH 112®. In certain embodiments, AVICEL PH 112® is present in an amount of about 20-40%, about 25-35%, or about 31% by weight. It was unexpectedly found that a solid form of Compound 1 is susceptible to hydrolysis. Without being limited by theory, it is thought that AVICEL PH 112®, being a low-moisture grade microcrystalline cellulose, can reduce hydrolysis of a solid form of Compound 1.

In certain embodiments, provided herein are pharmaceutical compositions comprising a solid form of Compound 1, stearic acid, lactose monohydrate and AVICEL PH 102®. In certain embodiments, provided herein are pharmaceutical compositions comprising a solid form of Compound 1, stearic acid (in an amount of about 0.1-5%, 0.1 to 1%, or 0.4% by weight), lactose monohydrate (in an amount of about 40-60%, 45-55%, or 49.2% by weight) and AVICEL PH 102® (in an amount of about 20-40%, 25-35%, or 31% by weight).

In certain embodiments, provided herein are pharmaceutical compositions comprising a solid form of Compound 1, lactose monohydrate and AVICEL PH 102®. In certain embodiments, provided herein are pharmaceutical compositions comprising a solid form of Compound 1, lactose monohydrate (in an amount of about 40-60%, 45-55%, or 49.2% by weight) and AVICEL PH 102® (in an amount of about 20-40%, 25-35%, or 31% by weight).

In certain embodiments, provided herein are pharmaceutical compositions comprising an opaque coating. Without being limited by theory, it was found that a more opaque coating protected the drug product from degradation. In some embodiments, the pharmaceutical composition is formulated as a tablet. In some such embodiments, the tablet is film coated. In some embodiments, the tablet is film coated to a weight gain of 1-8%. In others, the film coating is about 4% by weight of the tablet.

In certain embodiments, provided herein are pharmaceutical compositions comprising a solid form of Compound 1 that do not comprise stearic acid. Without being limited by theory, a lack of picking or sticking of certain tablet formulations by visual observation indicated that acceptable tablet formulations could be produced without the use of stearic acid.

In certain embodiments, provided herein are pharmaceutical compositions as set forth in Table 22-Table 30, Table 33-Table 35, Table 38-Table 40 and Table 43-Table 46, wherein the amounts of the recited components can independently be varied by 1%, 2%, 3%, 4%, 5%, 6%, 7%, 8%, 9%, 10%, 15%, 20% or 25%.

In certain embodiments, provided herein are liquid formulations comprising a solid form of Compound 1, an alcohol and polyethylene glycol. In certain embodiments, the alcohol and polyethylene glycol are present in a ratio of about 80:20 to about 20:80. In certain embodiments, the alcohol and polyethylene glycol are present in a ratio of about 50:50. In certain embodiments, the alcohol is ethanol. In certain embodiments, the polyethylene glycol is PEG 400. In one embodiment, provided herein are capsules filled with a liquid formulation comprising a solid form of Compound 1, an alcohol and polyethylene glycol. In one embodiment, a solid form of Compound 1 is an isotopologue of 7-(6-(2-hydroxypropan-2-yl)pyridin-3-yl)-1-((trans)-4-methoxycyclohexyl)-3,4-dihydropyrazino[2,3-b]pyrazin-2(1H)-one. In some embodiments, the isotopologue is enriched in $^{14}$C.

The pharmaceutical compositions provided herein can be provided in a unit-dosage form or multiple-dosage form. A unit-dosage form, as used herein, refers to physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an individually packaged tablet or capsule. A unit-dosage form may be administered in fractions or multiples thereof. A multiple-dosage form is a plurality of identical unit-dosage forms packaged in a single container to be administered in segregated unit-dosage form. In certain embodiments, the unit dosage forms provided herein comprise about 1 mg to about 100 mg of a solid form of Compound 1. In other embodiments, the unit dosage forms provided herein comprise about 5 mg to about 50 mg of a solid form of Compound 1. In other embodiments, the unit dosage forms provided herein comprise about 1 mg, about 5 mg, about 20 mg, about 45 mg, about 50 mg, about 75 mg or about 100 mg of a solid form of Compound 1. In other embodiments, the unit dosage forms provided herein comprise about 5 mg, about 15 mg, about 20 mg, about 30 mg, about 45 mg, and about 50 mg of a solid form of Compound 1.

In certain embodiments, provided herein are methods for preparing a composition provided herein, comprising: (i) weighing out the desired amount of a solid form of Compound 1 (such as Form 1, Form 2, Form 3, Form 4, Form 5, Form 6, Form 7 or Form 8) thereof and the desired amount of excipients (such as lactose monohydrate, croscarmellose sodium and microcrystalline cellulose); (ii) mixing or blending a solid form of Compound 1 and the excipients; (iii) passing the mixture of a solid form of Compound 1 and excipients through a screen (such as an 18 mesh or 1000 μm screen); (iv) mixing or blending a solid form of Compound 1 and the excipients after passage through the screen; (v) weighing out the desired amount of lubricating agents (such as stearic acid and/or magnesium stearate); (vi) passing the lubricating agents through a screen (such as a 30 mesh or 600 μm screen); (vii) mixing or blending a solid form of Compound 1, the excipients and the lubricating agents; (viii) compressing the mixture of a solid form of Compound 1, the excipients and the lubricating agents (such as into a tablet form); and (ix) coating the compressed mixture of a solid form of Compound 1, the excipients and the lubricating agents with a coating agent (such as Opadry pink, yellow or beige).

In certain embodiments, provided herein are methods for preparing a composition provided herein, comprising: (i) weighing out the desired amount of a solid form of Compound 1 (such as Form 1, Form 2, Form 3, Form 4, Form 5, Form 6, Form 7 or Form 8) thereof and the desired amount of excipients (such as lactose monohydrate, croscarmellose sodium and microcrystalline cellulose); (ii) mixing or blending a solid form of Compound 1 and the excipients; (iii) passing the mixture of a solid form of Compound 1 and excipients through a screen (such as an 18 mesh or 1000 μm screen); (iv) mixing or blending a solid form of Compound 1 and the excipients after passage through the screen; (v) weighing out the desired amount of lubricating agents (such as stearic acid and/or magnesium stearate); (vi) passing the lubricating agents through a screen (such as a 60 mesh or 250 μm screen); (vii) mixing or blending a solid form of Compound 1, the excipients and the lubricating agents; (viii) compressing the mixture of a solid form of Compound 1, the excipients and the lubricating agents (such as into a tablet form); and (ix) coating the compressed mixture of a solid form of Compound 1, the excipients and the lubricating agents with a coating agent (such as Opadry pink, yellow or beige).

In certain embodiments, provided herein are methods for preparing a composition provided herein, comprising: (i) weighing out the desired amount of a solid form of Compound 1 and the desired amount of excipients (such as lactose monohydrate, croscarmellose sodium and microcrystalline cellulose); (ii) passing the excipients through a screen (such as an 18 mesh or 1000 μm screen); (iii) mixing or blending (such as at 26 revolutions per minute for 20 minutes) a solid form of Compound 1 (such as Form 1, Form 2, Form 3, Form 4, Form 5, Form 6, Form 7 or Form 8) thereof and the excipients; (iv) passing the mixture of a solid form of Compound 1 and excipients through a screen (such as an 18 mesh or 1000 μm screen); (v) mixing or blending (such as at 26 revolutions per minute for 10 minutes) a solid form of Compound 1 and the excipients; (vi) weighing out the desired amount of lubricating agents (such as stearic acid and/or magnesium stearate); (vii) passing the lubricating agents through a screen (such as a 30 mesh or 600 μm screen); (viii) mixing or blending (such as at 26 revolutions per minute for 3 minutes) a solid form of Compound 1, the excipients and the lubricating agents; (ix) compressing the mixture of a solid form of Compound 1, the excipients and the lubricating agents (such as into a tablet form); and (x) coating the compressed mixture of a solid form of Compound 1, the excipients and the lubricating agents with a coating agent (such as Opadry pink, yellow or beige).

In certain embodiments, provided herein are methods for preparing a composition provided herein, comprising: (i) weighing out the desired amount of a solid form of Compound 1 and the desired amount of excipients (such as lactose monohydrate, croscarmellose sodium and microcrystalline cellulose); (ii) passing the excipients through a screen (such as an 18 mesh or 1000 μm screen); (iii) mixing or blending (such as at 26 revolutions per minute for 20 minutes) a solid form of Compound 1 (such as Form 1, Form 2, Form 3, Form 4, Form 5, Form 6, Form 7 or Form 8) thereof and the excipients; (iv) passing the mixture of a solid form of Compound 1 and excipients through a screen (such as an 18 mesh or 1000 μm screen); (v) mixing or blending (such as at 26 revolutions per minute for 10 minutes) a solid form of Compound 1 and the excipients; (vi) weighing out the desired amount of lubricating agents (such as stearic acid and/or magnesium stearate); (vii) passing the lubricating agents through a screen (such as a 60 mesh or 250 μm screen); (viii) mixing or blending (such as at 26 revolutions per minute for 3 minutes) a solid form of Compound 1, the excipients and the lubricating agents; (ix) compressing the mixture of a solid form of Compound 1, the excipients and the lubricating agents (such as into a tablet form); and (x) coating the compressed mixture of a solid form of Compound 1, the excipients and the lubricating agents with a coating agent (such as Opadry pink, yellow or beige).

In certain embodiments, the pharmaceutical compositions provided herein comprise Form 1, including substantially pure Form 1.

In certain embodiments, the pharmaceutical compositions provided herein comprise Form 2, including substantially pure Form 2.

In certain embodiments, the pharmaceutical compositions provided herein comprise Form 3, including substantially pure Form 3.

In certain embodiments, the pharmaceutical compositions provided herein comprise Form 4, including substantially pure Form 4.

In certain embodiments, the pharmaceutical compositions provided herein comprise Form 5, including substantially pure Form 5.

In certain embodiments, the pharmaceutical compositions provided herein comprise Form 6, including substantially pure Form 6.

In certain embodiments, the pharmaceutical compositions provided herein comprise Form 7, including substantially pure Form 7.

In certain embodiments, the pharmaceutical compositions provided herein comprise Form 8, including substantially pure Form 8.

Further provided herein are kits comprising a pharmaceutical composition of a solid form of Compound 1 provided herein. In particular embodiments, provided herein are kits comprising a unit dosage form of a solid form of Compound 1 provided herein. In certain embodiments of the kits provided herein, a solid form of Compound 1 is provided as Form 1. In certain embodiments of the kits provided herein, a solid form of Compound 1 is provided as Form 2. In certain embodiments of the kits provided herein, a solid form of Compound 1 is provided as Form 3. In certain embodiments of the kits provided herein, a solid form of Compound 1 is provided as Form 4. In certain embodiments of the kits provided herein, a solid form of Compound 1 is provided as Form 5. In certain embodiments of the kits provided herein, a solid form of Compound 1 is provided as Form 6. In certain embodiments of the kits provided herein, a solid form of Compound 1 is provided as Form 7. In certain embodiments of the kits provided herein, a solid form of Compound 1 is provided as Form 8.

6. EXAMPLES

The following Examples are presented by way of illustration, not limitation. The following abbreviations are used in descriptions and examples:

2MXETOH: 2-Methoxyethanol
AAC: Accelerated aging conditions (48 hours at 40° C. and 75% RH)
ACN: Acetonitril
Am: Amorphous
AmPhos: p-Dimethylamino phenyldibutylphosphine
API: Active Pharmaceutical Ingredient
AS: ID for anti-solvent crystallization experiment
Boc: tert-Butoxycarbonyl
dba: Dibenzylidene acetone
DCM: Dichloromethane
DIPEA: N,N-Diisopropylethylamine
DMF: N,N-Dimethylformide
DMSO: Dimethylsulfoxide
DSC: Differential Scanning calorimetry
ECP: ID for evaporative experiment
EDTA: Ethylenediamine tetraacetate
ESI: Electronspray ionization
EtOH: Ethanol
FTIR: Fourier Transform Infra Red Spectroscopy
GRP: Grinding experiment
HF: ID for hot-filtration crystallization experiment
HPLC: High performance liquid chromatography
IPA: 2-Propanol
LCMS: Liquid Chromatography with Mass Spectroscopy
MeOH: Methanol
mp: Melting point
MS: Mass spectrometry
Ms: Mesylate or methanesulfonyl
MTBE: tert-Butyl methyl ether
MTBE: methyl tert-butyl ether
NBS: N-Bromosuccinimide
NMP: N-Methyl-2-pyrrolidone
NMP: N-methylpyrrolidinone
NMR: Nuclear magnetic resonance
PSU: ID for cooling-evaporative crystallization experiment
QSA: ID for Phase 1 experiments
RH: Relative Humidity
RT: Room Temperature
S: Solvent
SDTA: Single Differential Thermal Analysis
SLP: ID for slurry experiment
SM: Starting material
TA: Thermal Analysis
TCP: ID for thermocycling and reflux experiment
Tf: triflate or trifluoromethanesulfonyl
TFA: Trifluoroacetic acid
TFE: 2,2,2-Trifluoroethanol
TGA: Thermogravimetric Analysis
TGA-MS/TGMS: Thermogravimetric Analysis coupled with Mass Spectroscopy
THF: Tetrahydrofuran
TLC: Thin layer chromatography
VDL: ID for vapor diffusion into solutions experiment
VDS: ID for vapor diffusion onto solids experiment
XRPD: X-Ray Powder Diffraction

6.1 Analytical Methods

XRPD patterns were obtained using the Crystallics T2 high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings. Data collection was carried out at room temperature using monochromatic $CuK_\alpha$ radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second frame) with an exposure time of 90 s for each frame. No background subtraction or curve smoothing was applied to the XRPD patterns. The carrier material used during XRPD analysis was transparent to X-rays and contributed only slightly to the background.

DSC analyses were performed on a DSC822e instrument (Mettler-Toledo GmbH, Switzerland). The DSC822e was calibrated for temperature and enthalpy with a small piece of indium (m.p. is 156.6° C.; ΔHf is 28.45 J/g). Samples were sealed in standard 40 µl aluminum pans, pin-holed and heated in the DSC from 25° C. to 300° C., at a heating rate of 10° C./min. Dry $N_2$ gas, at a flow rate of 50 ml/min was used to purge the DSC equipment during measurement. The cycling DSC's were measured in standard 40 µl aluminum pans, pin-holed and heated in the DSC from 25° C. to 190° C., then cooled back to 25° C. The heating and cooling rate was 10° C./min. Dry N$_2$ gas, at a flow rate of 50 ml/min was used to purge the DSC equipment during measurement.

TGA/SDTA analysis was adopted to determine mass loss caused by solvent or water loss from crystals. Monitoring the sample weight, during heating in a TGA/SDTA851e instrument (Mettler-Toledo GmbH, Switzerland), results in a weight vs. temperature curve. The TGA/SDTA851e was calibrated for temperature with indium and aluminum. Samples were weighed into 100 μL aluminum crucibles and sealed. The seals were pin-holed and the crucibles heated in the TGA from 25° C. to 300° C. at a heating rate of 10° C./min. Dry N$_2$ gas was used for purging. The gases evolved from the TGA samples were analyzed by a mass spectrometer Omnistar GSD 301 T2 (Pfeiffer Vacuum GmbH, Germany). The latter is a quadrupole mass spectrometer, which analyses masses in the range of 0-200 amu.

Digital images were automatically collected for all the wells of each well-plate, employing a Philips PCVC 840K CCD camera controlled by Crystallics Photoslider software.

FTIR spectra were recorded on a ThermoFischer Scientific FT-IR: Nicolet 6700.

Morphology analysis of the samples was carried out on an Olympus microscope. Small amounts of samples were dispersed in mineral oil on a glass slide with cover slips and viewed with 20× or 50× magnification.

Hygroscopicity was determined on a Surface Measurement Systems DVS. Typically a sample size of 2-10 mg was loaded into the DVS instrument sample pan and the sample was analyzed on a DVS automated sorption analyzer at room temperature. The relative humidity was increased from 0% to 90% RH at 10% RH step then 95% RH. The relative humidity was then decreased in a similar manner to accomplish a full adsorption/desorption cycle. For selected hydrated forms, the analysis started at 50% RH and increased to 90% RH at 10% RH step. The relative humidity was then decreased in a similar manner to 0% RH followed by increasing to 50% RH.

High Performance Liquid Chromatography (HPLC) was performed according to the conditions in Table 1 and gradient program in Table 2.

TABLE 1

High Performance Liquid Chromatography (HPLC) experimental conditions

| Manufacturer | Agilent |
|---|---|
| HPLC | HP1200sl |
| UV-detector | HP DAD |
| MS-detector | HP1100 API-ES MSD VL-type |
| Column | Waters Sunfire C18 (100 × 4.6 mm; 3.5 μm) |
| Column Temperature | 40° C. |
| Mobile Phase A | 10 mM ammonium acetate |
| Mobile Phase B | Acetonitrile 100% |
| Flow Rate | 1.0 ml/min |
| Post time | 1 min |
| UV-Detector | DAD |
| Range | 200-400 nm |
| Wavelength | 220 nm |
| Slit width | 4 nm |
| Time | 0-17 min |
| MS-Detector | MSD |
| Scan | positive |
| Mass Range | 70-1000 amu |
| Fragmentator | 70 |
| Time | 0-20 min |

TABLE 1-continued

High Performance Liquid Chromatography (HPLC) experimental conditions

| Manufacturer | Agilent |
|---|---|
| Autosampler: | |
| Temperature | Not controlled |
| Injection mode | loop |
| Injection volume | 5 μL |
| Needle wash | 2/3; Acetonitrile/H$_2$O (v/v) |
| Dilution solvent | Acetonitrile |

TABLE 2

High Performance Liquid Chromatography (HPLC) experimental gradient program

| Time (mins) | % A | % B |
|---|---|---|
| 0 | 90 | 10 |
| 16 | 10 | 90 |
| 20 | 10 | 90 |
| 21 | 90 | 10 |

The compound integrity is expressed as a peak-area percentage, calculated from the area of each peak in the chromatogram, except the 'injection peak', and the total peak-area, as follows:

$$peak-area\% = \frac{peak-area}{total-area} * 100\%$$

The peak-area percentage of the compound of interest is employed as an indication of the purity of the component in the sample.

Crystal16® multiple-reactor system (Avantium Technologies) holds 16 (4×4) standard HPLC glass vials (11.5 mm diameter, flat bottomed, 1.8 mL volume). A unit consists of four independently heated aluminum reactor blocks encased in a robust bench top setup. These blocks are electrically heated and cooled by a combination of Peltier elements and a cryostat. In order to prevent condensation of water on the reactor blocks and electronics during runs at temperatures below 10° C., the Crystal16® system provides an inlet for a dry purge gas (typically nitrogen). Operating Parameters are provided in Table 3.

TABLE 3

Operating Parameters of Crystal16 ® multiple-reactor system

| Temperature range | −15° C. to 150° C. |
|---|---|
| Heating/cooling | Individually programmable per reactor block |
| Temperature profile | Unlimited heating/cooling/hold steps per run programmable |
| Temperature control accuracy | 0.1° C. |
| Heating/cooling ramps | Programmable between 0° C. and 20° C./min |
| Stirrer speed (magnetic stirrer bars) | Programmable from 0-1250 rpm |
| Turbidity measurement | Per individual reactor in transmission |

6.2 Summary of Cocrystal Formation Screen

A total of 314 cocrystal formation experiments were divided over four different crystallization methods. Based on the chemical structure of Compound 1, 10 different coformers were selected (Table 5). The cocrystal formation experiments were performed as described in §6.3.

Physical stability of all samples was studied by exposing all solids to accelerated ageing conditions (40° C./75% RH for 48 hours) followed by re-analysis by XRPD and digital imaging. After exposure to accelerated ageing conditions, all solids were re-classified on the basis of their new XRPD patterns. The assignment of solid forms was primarily based on the XRPD analysis.

The cocrystals formed with fumaric acid (Form 1 and Form 2), benzoic acid (Form 3 and Form 4), gentisic acid (Form 5 and Form 6) and maleic acid (Form 7 and Form 8) appear to be stable at accelerated aging conditions (40° C. and 75% RH, 48 hours). TGMS, FTIR and HPLC analysis of the potential cocrystals from fumaric acid, benzoic acid, gentisic acid and maleic acid confirmed that these XRPD patterns belong to new cocrystals of Compound 1. Of those cocrystals only the crystal with fumaric acid (Form 1) is a non-solvated anhydrous cocrystal. More complex crystal structures for instance were found in the other fumaric acid cocrystal (Form 2), which turned out to be a monohydrate of the fumaric acid cocrystal of Compound 1. The above described results clearly demonstrates that co-crystals between Compound 1 and both aliphatic and aromatic carboxylic acids can be formed. Concluding remarks per analysis of these solids are given in Table 4.

TABLE 4

Summary table of the analytical experiments, results and conclusions of the cocrystals of Compound 1

|  | Form 1 | Form 2 | Form 3 | Form 4 |
| --- | --- | --- | --- | --- |
| XRPD | Unique pattern | Unique pattern | Unique pattern | Unique pattern |
| TGMS | No significant mass loss | 1.12% mass loss (water) | 5% mass loss (water) | 1.7% mass loss (acetone) |
| SDTA | Single melting point ($T_{peak}$ is 187.6° C.) | Endothermic dehydration event ($T_{peak}$ is 146° C.) Single melting point ($T_{peak}$ is 193.5° C.) | Series of endothermic events- individual events not interpreted | Single melting point ($T_{peak}$ is 83.2° C.) |
| HPLC | Highly pure Cmpd 1 (100%) | Highly pure Cmpd 1 (98.9%) | Highly pure Cmpd 1 (99.9%) | Highly pure Cmpd 1 (99.5%) |
| FTIR | Changes in the spectrum as compared to that of Compound 1-1800-1600 cm$^{-1}$ shifts (tertiary amines) | Changes in the spectrum as compared to that of Cmpd 1-1800-1600 cm$^{-1}$ shift doubled (tertiary amines) | Changes in the spectrum as compared to that of Cmpd 1-1800-1600 cm$^{-1}$ shifts (tertiary amines) | Changes in the spectrum as compared to that of Cmpd 1-1800-1600 cm$^{-1}$ shifts (tertiary amines) |
| Conclusion | Cocrystal of Cmpd 1 with fumaric acid | Monohydrate cocrystal of Cmpd 1 fumarate salt | Cocrystal of Cmpd 1 with benzoic acid | Cocrystal of Cmpd 1 with benzoic acid |
|  | Form 5 | Form 6 | Form 7 | Form 8 |
| XRPD | Unique pattern | Unique pattern | Unique pattern | Unique pattern |
| TGMS | 4.6% mass loss (water and acetone) | 0.9% mass loss (acetonitrile) | 4% mass loss (water and acetonitrile) | 1% mass loss (ethylacetate) |
| SDTA | Single melting point ($T_{peak}$ is 95.5° C.) | Single melting point ($T_{peak}$ is 148° C.) | Single melting point ($T_{peak}$ is 86° C.) | Single melting point ($T_{peak}$ is 118.8° C.) |
| HPLC | Highly pure Cmpd 1 (99.3%) | Pure Cmpd 1 (96.55%) | Highly pure Cmpd 1 (98.3%) | Low purity Cmpd 1 (87.2%) |
| FTIR | Changes in the spectrum as compared to that of Cmpd 1-1800-1600 cm$^{-1}$ shifts (tertiary amines) | Changes in the spectrum as compared to that of Cmpd 1-1800-1400 cm$^{-1}$ shifts (tertiary amines, but also presence of an impurity) | Changes in the spectrum as compared to that of Cmpd 1-1800-1600 cm$^{-1}$ shifts (tertiary amines) | Changes in the spectrum as compared to that of Cmpd 1-1800-1600 cm$^{-1}$ shifts (tertiary amines) |
| Conclusion | Cocrystal of Cmpd 1 with gentisic acid although high solvent content | Cocrystal of Cmpd 1 with gentisic acid | Cocrystal of Cmpd 1 with maleic acid although high solvent content | Cocrystal of Cmpd 1 with maleic acid, although not preferred because of high impurity levels |

Figure 5:
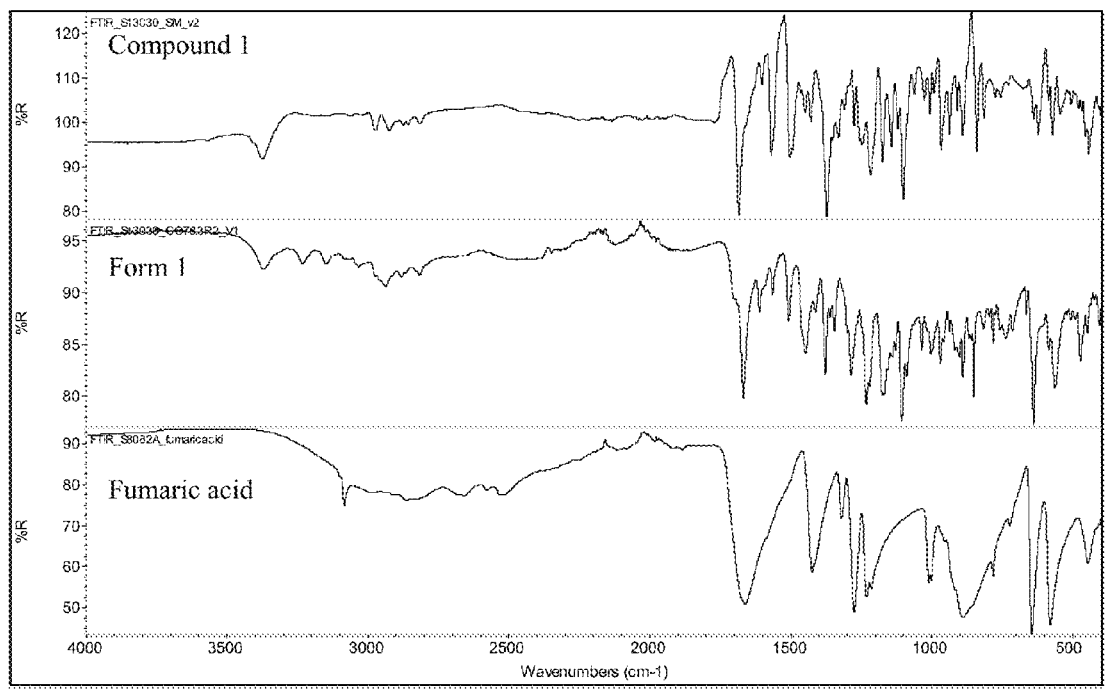
FIG. 5 depicts a fourier transform infrared spectroscopy (FTIR) overlay of Compound 1, Form 1 and fumaric acid.
Figure 6:
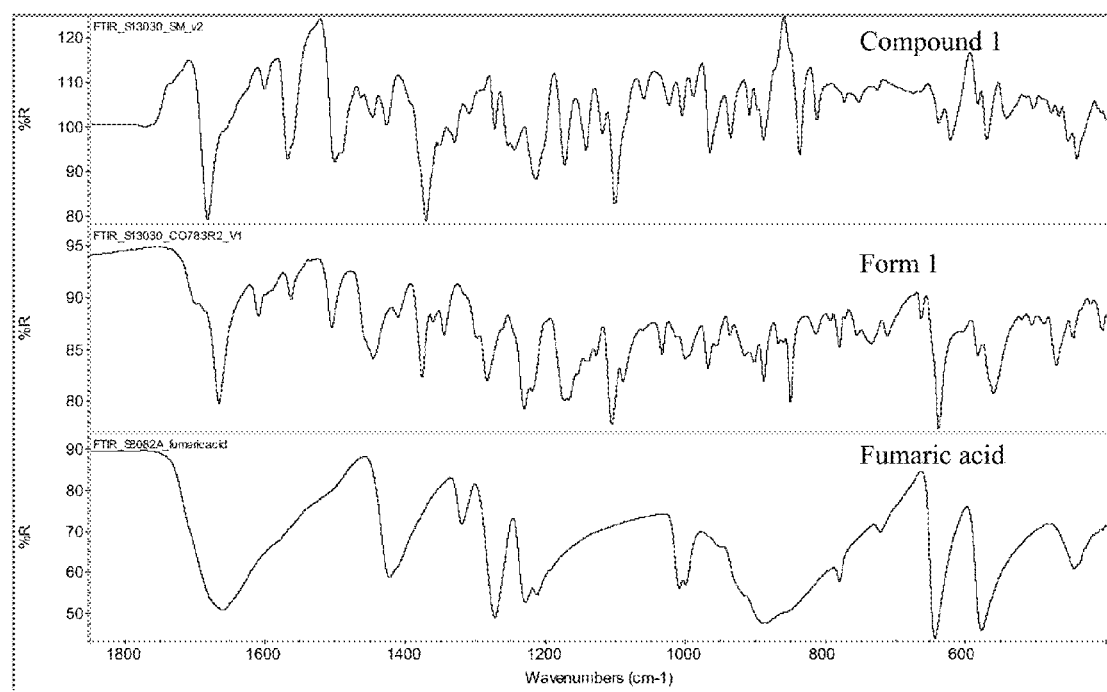
FIG. 6 depicts a FTIR overlay of Compound 1, Form 1 and fumaric acid in the region of 1800-400 $cm^{-1}$.

Form 1 is believed to be a cocrystal of Compound 1 free base with a 1:1 stoichiometry as concluded by the single molecule of fumaric acid identified by FT-IR (see FIG. 5 and FIG. 6—shift between 1800-1600 cm$^{-1}$). Form 2 crystal structure was determined by single crystal X-ray diffraction. In contrast with Form 1, Form 2 appears to be a fumaric acid cocrystal of Compound 1 fumarate salt, which has also one molecule of water per unit. The FT-IR spectrum (see FIG. 10 and FIG. 11) clearly shows a doubled shift at around 1800-1600 cm$^{-1}$ indicating the interaction of two molecules of fumaric acid with the nitrogens of Compound 1. TGMS analysis of Form 4, Form 6 and Form 7 revealed that these co-crystals are solvated (see FIG. 21, FIG. 32 and FIG. 38). HPLC analysis of Form 6 and Form 8, showed the presence of an impurity with a retention time of 6.05 min in HPLC analysis (see FIG. 34 and FIG. 45). Further research is needed to identify the nature and cause of the impurity. Although the XRPD pattern of Form 3 is unique, the SDTA signal does not support the presence of a single solid phase. The FTIR spectra (see FIG. 19 and FIG. 20) of Form 3 showed peak shifts; however, their interpretation is rather complicated. LCMS analysis of Form 3 showed that Compound 1 is present in the sample, which is 99.9% pure (see FIG. 18).

6.3 Experimental Methods

In total, 324 experiments were performed, including 126 cooling evaporative experiments, 66 slurry experiments, 66 powder in saturated solution experiments and 66 grinding experiments. In all methods, 11 solvents (see Table 6) and 10 coformers were tested (see Table 5), including 6 blank experiments per method. The coformers and the solvents used were the same for all four methods, while the solvents per method differed due to differences in solubility of Compound 1 in the solvents. The coformers have been selected on the basis of their H-bonding capability, diversity, pharmaceutical acceptability and solubility in the proposed solvents. An overview of the combination of methods and solvents used is provided in Table 5 and Table 6. The solvents used in the polymorph screen were either HPLC or reagent grade.

TABLE 5

Coformers used in the cocrystal screen

| # | Cocrystal former |
|---|---|
| 1 | Meglumine |
| 2 | Nicotinamide |
| 3 | Tromethamine |
| 4 | L-Lysine |
| 5 | Maleic acid |
| 6 | Gentisic acid |
| 7 | Fumaric acid |
| 8 | Glutamic acid |
| 9 | Benzoic acid |
| 10 | L-Arginine |

TABLE 6

Solvents used in the cocrystal screen

| # | Solvents |
|---|---|
| 1 | Ethanol |
| 2 | Ethanol/water (10/90) |
| 3 | Ethanol/water (50/50) |
| 4 | Methanol/water (50/50) |
| 5 | Tetrahydrofuran/water (50/50) |
| 6 | Acetonitrile |
| 7 | Ethyl acetate |
| 8 | Acetone and water (10/90) |
| 9 | Cyclohexane |
| 10 | p-xylene |
| 11 | Water |

6.3.1 Cooling Evaporative Experiments

The cooling evaporative experiments employed 4 coformers, 6 solvents and two Compound 1:coformer ratios (see Table 8). Compound 1 free base (the starting material) and coformers were solid dosed in 1.8 mL experimental vials. A suitable volume of solvent was added to reach a close-to saturated solution. Following, the HPLC vials were capped and placed in the Crystal16® system to undergo the temperature profile as described in Table 7. Also 6 control experiments were performed. At the end of the temperature profile, the solids were separated from the liquids, dried and analyzed by XRPD and digital imaging. The mother liquids after separation of solids were evaporated and the remaining solids analyzed by XRPD and digital imaging too.

Subsequently, all solids were placed in a climate chamber at 40° C. and 75% RH for 70 hours and again analyzed by XRPD and digital imaging.

TABLE 7

Temperature profiles ($T_{profile}$) for the cocrystallization experiments

| $T_{start}$ (° C.) | Heating rate (° C./min) | $T_{max}$ (° C.) | Hold (minute) | Cooling rate (° C./h) | $T_{end}$ (° C.) | Age time (h) |
|---|---|---|---|---|---|---|
| 20 | 10 | 40 | 60 | 1 | 2 | 48 |

TABLE 8

Experimental conditions of the cocrystal cooling evaporation experiments

| Coformer | Solvent | Mass of Cmpd 1 (mg) | Mass of Coformer (mg) | Solvent volume (µL) | Molar Ratio (Cmpd 1:Co-former) | Dissolved before $T_{profile}$ | Solids after $T_{profile}$ |
|---|---|---|---|---|---|---|---|
| Maleic acid | EtOH | 30.4 | 10.30 | 750 | 1:1.1 | No | No |
| | EtOH/Water (50/50) | 30.8 | 9.80 | 400 | | Yes | No |
| | MeOH/Water (50/50) | 29.8 | 9.70 | 400 | | Yes | No |
| | THF/Water (50/50) | 30.9 | 10.00 | 400 | | Yes | No |
| | Acetonitrile | 29.5 | 9.60 | 1000 | | No | Yes |
| | Ethyl acetate | 29.5 | 9.70 | 1000 | | No | Yes |
| | EtOH | 29.7 | 35.60 | 750 | 1:4 | Yes | No |

TABLE 8-continued

Experimental conditions of the cocrystal cooling evaporation experiments

| Coformer | Solvent | Mass of Cmpd 1 (mg) | Mass of Coformer (mg) | Solvent volume (μL) | Molar Ratio (Cmpd 1:Co-former) | Dissolved before $T_{profile}$ | Solids after $T_{profile}$ |
|---|---|---|---|---|---|---|---|
| | EtOH/Water (50/50) | 29.9 | 35.80 | 400 | | Yes | No |
| | MeOH/Water (50/50) | 30.3 | 36.60 | 400 | | Yes | No |
| | THF/Water (50/50) | 30.1 | 35.70 | 400 | | Yes | No |
| | Acetonitrile | 30.2 | 35.30 | 1000 | | No | Yes |
| | Ethyl acetate | 29.9 | 35.70 | 1000 | | No | Yes |
| Gentisic acid (2,5-Dihydroxy benzoic acid) | EtOH | 29.5 | 12.80 | 750 | 1:1.1 | No | Yes |
| | EtOH/Water (50/50) | 29.5 | 13.50 | 400 | | No | No |
| | MeOH/Water (50/50) | 29.9 | 12.80 | 400 | | No | Yes |
| | THF/Water (50/50) | 30.9 | 13.50 | 400 | | No | No |
| | Acetonitrile | 29.7 | 13.00 | 1000 | | No | Yes |
| | Ethyl acetate | 30.9 | 13.50 | 1000 | | No | No |
| | EtOH | 30.5 | 47.50 | 750 | 1:4 | No | No |
| | EtOH/Water (50/50) | 30.1 | 48.20 | 400 | | No | Yes |
| | MeOH/Water (50/50) | 29.7 | 47.40 | 400 | | No | Yes |
| | THF/Water (50/50) | 31 | 47.20 | 400 | | No | No |
| | Acetonitrile | 30.2 | 47.80 | 1000 | | No | Yes |
| | Ethyl acetate | 30.4 | 47.20 | 1000 | | No | Yes |
| Fumaric acid | EtOH | 30.2 | 9.80 | 750 | 1:1.1 | No | Yes |
| | EtOH/Water (50/50) | 30.2 | 9.90 | 400 | | No | Yes |
| | MeOH/Water (50/50) | 30.6 | 10.00 | 400 | | No | Yes |
| | THF/Water (50/50) | 29.9 | 10.10 | 400 | | No | No |
| | Acetonitrile | 29.8 | 10.00 | 1000 | | No | Yes |
| | Ethyl acetate | 30 | 10.20 | 1000 | | No | Yes |
| | EtOH | 30.1 | 35.20 | 750 | 1:4 | No | Yes |
| | EtOH/Water (50/50) | 31 | 35.20 | 400 | | No | Yes |
| | MeOH/Water (50/50) | 30.3 | 35.30 | 400 | | No | Yes |
| | THF/Water (50/50) | 30.1 | 35.80 | 400 | | Yes | No |
| | Acetonitrile | 30.4 | 35.60 | 1000 | | No | Yes |
| | Ethyl acetate | 30 | 35.80 | 1000 | | No | Yes |
| Benzoic acid | EtOH | 30.4 | 10.80 | 750 | 1:1.1 | No | No |
| | EtOH/Water (50/50) | 30.8 | 10.40 | 400 | | No | No |
| | MeOH/Water (50/50) | 29.8 | 10.70 | 400 | | No | No |
| | THF/Water (50/50) | 30.9 | 10.60 | 400 | | No | No |
| | Acetonitrile | 29.5 | 10.50 | 1000 | | No | Yes |
| | Ethyl acetate | 29.5 | 10.60 | 1000 | | No | No |
| | EtOH | 29.7 | 37.50 | 750 | 1:4 | No | No |
| | EtOH/Water (50/50) | 29.9 | 37.60 | 400 | | No | No |
| | MeOH/Water (50/50) | 30.3 | 38.00 | 400 | | No | Yes |
| | THF/Water (50/50) | 30.1 | 38.00 | 400 | | No | No |
| | Acetonitrile | 30.2 | 37.70 | 1000 | | No | No |
| | Ethyl acetate | 29.9 | 37.50 | 1000 | | No | No |
| none | EtOH | 30.2 | — | 750 | — | No | Yes |
| | EtOH/Water (50/50) | 30.2 | — | 400 | | No | No |
| | MeOH/Water (50/50) | 30.6 | — | 400 | | No | Yes |
| | THF/Water (50/50) | 29.9 | — | 400 | | Yes | No |
| | Acetonitrile | 29.8 | — | 1000 | | No | Yes |
| | Ethyl acetate | 30 | — | 1000 | | No | Yes |

Volume of solvent is 1000 μL.

6.3.2 Cocrystal Formation Slurry Experiments

Compound 1 free base was solid dosed in 1.8 mL scale experimental vials. The coformer was added at a ratio of 1:1.1 (Compound 1:coformer). The solvent and a stirring bar were added to the vials. The experiments used 4 coformers and 6 solvents (see Table 9) and 6 control experiments without coformer were also performed. Then, the vials were capped and stirred at ambient conditions for 3 days. After the solids were separated from the liquids, the solids were analyzed wet by XRPD and digital imaging. Subsequently, both the solids and mother liquors were dried and evaporated under vacuum at ambient temperature (10 mbar for 24 hours). The solids obtained were then analyzed by XRPD and digital imaging. Subsequently, the solids were incubated in a climate chamber at 40° C. and 75% RH for 48 hours and again analyzed by XRPD and digital imaging.

TABLE 9

Experimental conditions of the cocrystal slurry experiments

| Coformer | Solvent | Mass of Cmpd 1 (mg) | Mass of Coformer (mg) | Dissolved before $T_{profile}$ | Solids after $T_{profile}$ |
|---|---|---|---|---|---|
| Maleic acid | Acetonitrile | 31.0 | 9.50 | No | Yes |
| | Acetone/water (10/90) | 29.4 | 10.00 | No | No |
| | Cyclohexane | 29.9 | 10.00 | No | Yes |
| | p-Xylene | 31.1 | 9.80 | No | Yes |
| | Water | 30.7 | 10.00 | No | No |
| | Ethanol/water (10/90) | 30.7 | 10.00 | No | No |
| Gentisic acid (2,5-Dihydroxy benzoic acid) | Acetonitrile | 30.8 | 13.10 | No | Yes |
| | Acetone/water (10/90) | 29.2 | 13.00 | No | Yes |
| | Cyclohexane | 30.1 | 13.40 | No | Yes |
| | p-Xylene | 30.8 | 13.50 | No | Yes |

TABLE 9-continued

Experimental conditions of the cocrystal slurry experiments

| Coformer | Solvent | Mass of Cmpd 1 (mg) | Mass of Coformer (mg) | Dissolved before T$_{profile}$ | Solids after T$_{profile}$ |
|---|---|---|---|---|---|
| | Water | 31.1 | 13.40 | No | Yes |
| | Ethanol/water (10/90) | 31.0 | 13.20 | No | Yes |
| Fumaric acid | Acetonitrile | 31.2 | 10.40 | No | Yes |
| | Acetone/water (10/90) | 31.1 | 10.20 | No | Yes |
| | Cyclohexane | 30.2 | 10.30 | No | Yes |
| | p-Xylene | 30.8 | 10.10 | No | Yes |
| | Water | 30.5 | 10.00 | No | Yes |
| | Ethanol/water (10/90) | 29.2 | 10.00 | No | Yes |
| Benzoic acid | Acetonitrile | 30.5 | 10.70 | No | Yes |
| | Acetone/water (10/90) | 29.7 | 11.00 | No | Yes |
| | Cyclohexane | 30.5 | 10.20 | No | Yes |
| | p-Xylene | 30.8 | 10.80 | No | Yes |
| | Water | 29.2 | 11.00 | No | Yes |
| | Ethanol/water (10/90) | 30.3 | 10.30 | No | Yes |
| none | Acetonitrile | 30.8 | — | No | Yes |
| | Acetone/water (10/90) | 30.7 | — | No | Yes |
| | Cyclohexane | 29.1 | — | No | Yes |
| | p-Xylene | 29.8 | — | No | Yes |
| | Water | 30.8 | — | No | Yes |
| | Ethanol/water (10/90) | 29.2 | — | No | Yes |

Volume of solvent is 500 µL.

6.3.3 Powder in Saturated Solutions Experiments

In these experiments 4 coformers and 6 solvents were tested (see Table 10). In each solvent, saturated solutions of Compound 1 were prepared. To the saturated solutions the solid coformers were added until the coformer did not dissolve anymore or precipitation occurred. The samples remained for 4 hours at ambient temperature with stirring. In addition, 6 control experiments were performed. Subsequently, the solids were separated from the liquids. The solids were dried and mother liquors were evaporated under vacuum. All obtained solids were then analyzed by XRPD and digital imaging. Subsequently, the solids were placed in a climate chamber at 40° C. and 75% RH for 3 days after which they were analyzed by XRPD and digital imaging again.

TABLE 10

Experimental conditions for the powder in saturated solutions experiments

| Coformer | Solvent | Mass of Cmpd 1 (mg) | Mass of Coformer (mg) | Solvent volume (µL) | Dissolved before T$_{profile}$ | Solids after T$_{profile}$ |
|---|---|---|---|---|---|---|
| Maleic acid | EtOH | 30.0 | 20.00 | 950 | No | No |
| | EtOH/Water (50/50) | 30.0 | 20.00 | 1000 | No | No |
| | MeOH/Water (50/50) | 30.0 | 20.00 | 1000 | No | No |
| | THF/Water (50/50) | 30.0 | 20.00 | 250 | No | Yes |
| | Acetonitrile | 30.0 | 20.00 | 1000 | No | Yes |
| | Ethyl acetate | 30.0 | 20.00 | 1000 | No | Yes |
| Gentisic acid (2,5-Dihydroxy benzoic acid) | EtOH | 30.0 | 20.00 | 950 | No | Yes |
| | EtOH/Water (50/50) | 30.0 | 20.00 | 1000 | No | No |
| | MeOH/Water (50/50) | 30.0 | 20.00 | 1000 | No | Yes |
| | THF/Water (50/50) | 30.0 | 20.00 | 250 | No | Yes |
| | Acetonitrile | 30.0 | 20.00 | 1000 | No | Yes |
| | Ethyl acetate | 30.0 | 20.00 | 1000 | No | Yes |
| Fumaric acid | EtOH | 30.0 | 20.00 | 950 | No | Yes |
| | EtOH/Water (50/50) | 30.0 | 20.00 | 1000 | No | Yes |
| | MeOH/Water (50/50) | 30.0 | 20.00 | 1000 | No | Yes |
| | THF/Water (50/50) | 30.0 | 20.00 | 250 | No | Yes |
| | Acetonitrile | 30.0 | 20.00 | 1000 | No | Yes |
| | Ethyl acetate | 30.0 | 20.00 | 1000 | No | Yes |
| Benzoic acid | EtOH | 30.0 | 20.00 | 950 | No | No |
| | EtOH/Water (50/50) | 30.0 | 20.00 | 1000 | No | No |
| | MeOH/Water (50/50) | 30.0 | 20.00 | 1000 | No | No |
| | THF/Water (50/50) | 30.0 | 20.00 | 250 | No | No |
| | Acetonitrile | 30.0 | 20.00 | 1000 | No | Yes |
| | Ethyl acetate | 30.0 | 20.00 | 1000 | No | No |
| | Ethyl acetate | 30.0 | 20.00 | 1000 | No | Yes |
| none | EtOH | 30.0 | — | 950 | No | No |
| | EtOH/Water (50/50) | 30.0 | — | 1000 | No | No |
| | MeOH/Water (50/50) | 30.0 | — | 1000 | No | No |
| | THF/Water (50/50) | 30.0 | — | 250 | No | No |
| | Acetonitrile | 30.0 | — | 1000 | No | No |
| | Ethyl acetate | 30.0 | — | 1000 | No | No |

Volume of solvent is 1000 µL; Molar ratio of Compound 1 and coformer is 1:1.

6.3.4 Grinding Experiments 66 single-solvent-drop grinding experiments were performed using 4 coformers and 6 solvents. Moreover 6 control experiments were performed. Compound 1 free base was weighed into metal grinding vials, containing two stainless steel grinding balls. The coformers and solvents were added (see Table 11). The molar ratio of compound 1 free base and the coformer is 1:1.1. The experiments were shaken for 1 hour at a frequency of 30 Hz. After the 1-hour shaking, the samples were analyzed by XRPD and digital imaging. Subsequently the samples were exposed to accelerated aging conditions (40° C., 75% RH) for 3 days and re-analyzed by XRPD and digital imaging.

TABLE 11

Conditions of grinding experiments

| Coformer | Solvent | Mass of Cmpd 1 (mg) | Mass of Coformer (mg) | Solids after $T_{profile}$ |
|---|---|---|---|---|
| Maleic acid | Acetonitrile | 29.4 | 9.90 | Yes |
| | Acetone/Water (10/90) | 31.3 | 9.80 | No |
| | Cyclohexane | 30.8 | 10.10 | Yes |
| | p-Xylene | 29.8 | 10.00 | Yes |
| | Water | 30.2 | 10.40 | Yes |
| | Ethanol/Water (10/90) | 30.8 | 10.20 | Yes |
| Gentisic acid (2,5-Dihydroxy benzoic acid) | Acetonitrile | 30.8 | 13.30 | Yes |
| | Acetone/Water (10/90) | 31.3 | 13.50 | Yes |
| | Cyclohexane | 31.2 | 13.40 | Yes |
| | p-Xylene | 29.2 | 13.30 | Yes |
| | Water | 30.5 | 13.30 | Yes |
| | Ethanol/Water (10/90) | 30.0 | 13.50 | Yes |
| Fumaric acid | Acetonitrile | 30.5 | 10.20 | Yes |
| | Acetone/Water (10/90) | 31.3 | 10.20 | Yes |
| | Cyclohexane | 30.2 | 10.20 | Yes |
| | p-Xylene | 30.9 | 10.20 | Yes |
| | Water | 29.8 | 10.20 | Yes |
| | Ethanol/Water (10/90) | 31.3 | 10.20 | Yes |
| Benzoic acid | Acetonitrile | 29.8 | 10.70 | Yes |
| | Acetone/Water (10/90) | 29.9 | 10.70 | Yes |
| | Cyclohexane | 30.6 | 10.50 | Yes |
| | p-Xylene | 30.4 | 10.80 | Yes |
| | Water | 30.1 | 10.30 | Yes |
| | Ethanol/Water (10/90) | 30.2 | 10.30 | Yes |
| none | Acetonitrile | 29.8 | — | Yes |
| | Acetone/Water (10/90) | 30.7 | — | Yes |
| | Cyclohexane | 30.7 | — | Yes |
| | p-Xylene | 30.6 | — | Yes |
| | Water | 30.4 | — | Yes |
| | Ethanol/Water (10/90) | 29.8 | — | Yes |

Volume of solvent is 10 μL.

6.3.5 Cocrystal Solid Form 1

Form 1 was prepared in cooling evaporative experiments when fumaric acid was used as the coformer and ethyl acetate was used as the solvent. Form 1 is an anhydrous cocrystal form of Compound 1 and fumaric acid in a 1:1 stoichiometric ratio.

FIG. 1 provides an overlay of XRPD patterns of Compound 1, Form 1, Form 2 and fumaric acid (from bottom to top). A list of X-Ray Diffraction Peaks for Form 1 is provided below in Table 12.

TABLE 12

X-Ray Diffraction Peaks for Form 1

| Two-theta angle (°) | d Space (Å) | Relative Intensity (%) |
|---|---|---|
| 7.14 | 12.37 | 62.24 |
| 11.42 | 7.74 | 24.68 |
| 12.82 | 6.9 | 20.15 |

TABLE 12-continued

X-Ray Diffraction Peaks for Form 1

| Two-theta angle (°) | d Space (Å) | Relative Intensity (%) |
|---|---|---|
| 14.66 | 6.04 | 8.32 |
| 16.1 | 5.5 | 9.11 |
| 22.7 | 3.91 | 89.49 |
| 25.5 | 3.49 | 15.76 |

FIG. 2 and FIG. 3 provide TGMS data and TGA/SDTA data of Form 1, respectively. No mass loss of the sample was observed between 25° C. and 100° C. when heated from 25° C. to 300° C. According to the SDTA signal in FIG. 3, an endothermic melt event was observed at 187.6° C., followed by immediate decomposition.

Figure 4:
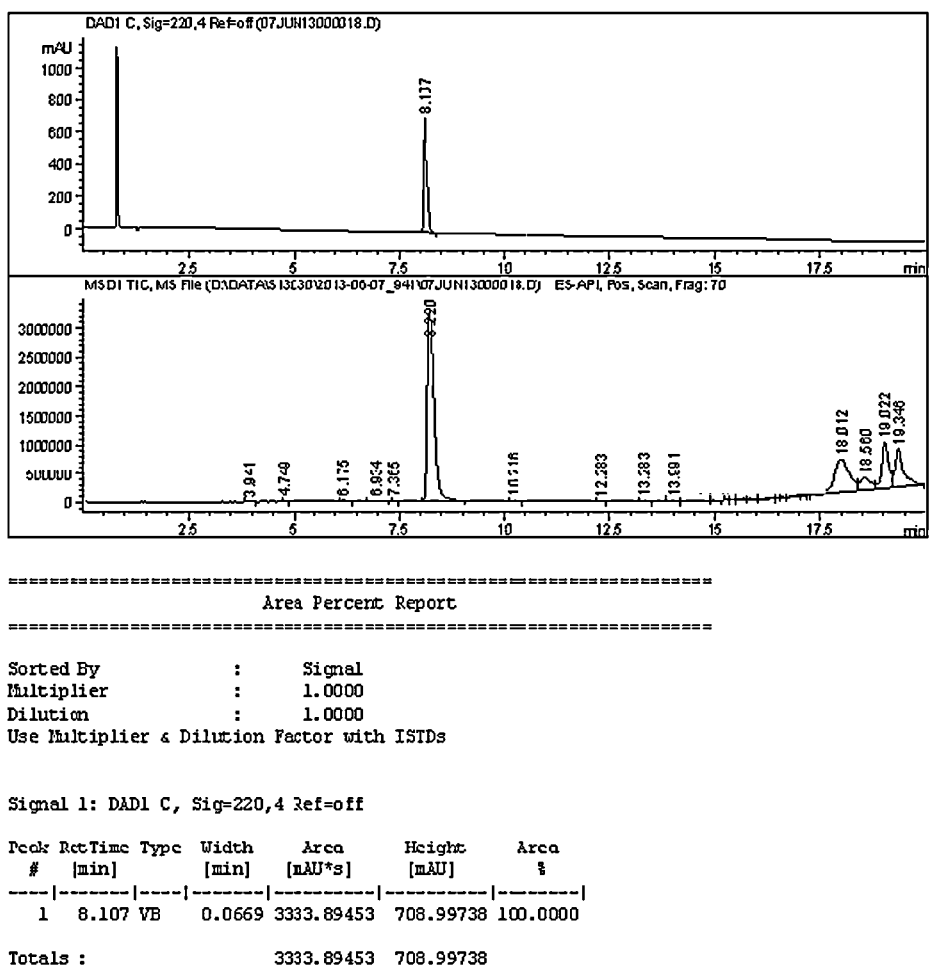
FIG. 4 depicts high performance liquid chromatography coupled with mass spectrometry of Form 1.

FIG. 4 provides HPLC and MS data of Form 1. The peak retention time is 8.1 minutes. HPLC data indicates that the sample purity is 100.0% (area %).

FIG. 5 provides an FTIR overlay of Compound 1 (top), Form 1 (middle) and fumaric acid (bottom). The overlay indicates that the main shifts take place in the spectra in the region 1800-1500 $cm^{-1}$ and 1600-1400 $cm^{-1}$.

FIG. 6 provides an FTIR overlay of Compound 1 (top), Form 1 (middle) and fumaric acid (bottom) in the region of 1800-400 $cm^{-1}$. The overlay emphasizes the area between 1800-1500 $cm^{-1}$ and 1600-1400 $cm^{-1}$ corresponding to tertiary amines shifts where the H-bonding is taking place between the coformer and Compound 1.

6.3.6 Cocrystal Solid Form 2

Form 2 was prepared in cooling evaporative experiments when fumaric acid was used as the coformer and a mixture of methanol and water (50/50) was used as the solvent. Form 2 is a monohydrated cocrystal form of Compound 1 and fumaric acid.

FIG. 1 provides an overlay of XRPD patterns of Compound 1, Form 1, Form 2 and fumaric acid (from bottom to top). A list of X-Ray Diffraction Peaks for Form 2 is provided below in Table 13. Form 2 appears to be a fumaric acid co-crystal of Compound 1 fumarate salt, which has also one molecule of water per unit.

TABLE 13

X-Ray Diffraction Peaks for Form 2

| Two-theta angle (°) | d Space (Å) | Relative Intensity (%) |
|---|---|---|
| 7.42 | 11.9 | 44.47 |
| 10.38 | 8.51 | 12.43 |
| 13.7 | 6.46 | 8.85 |
| 15.94 | 5.55 | 14.52 |
| 17.9 | 4.95 | 10.79 |
| 18.3 | 4.84 | 23.68 |
| 19.42 | 4.57 | 12.54 |
| 22.42 | 3.96 | 9.8 |
| 23.38 | 3.8 | 7.15 |
| 23.82 | 3.73 | 58.81 |
| 25.46 | 3.49 | 8.34 |
| 26.78 | 3.33 | 12.38 |

FIG. 7 and FIG. 8 provide TGMS data and TGA/SDTA data of Form 2. A mass loss of 1.12% by weight of the sample corresponding to water was observed between 35° C. and 175° C. during an endothermic event with $T_{peak}$ at 146° C. suggesting the solvated nature of the sample, when heated from 25° C. to 300° C. According to the SDTA signal in FIG. 8, an endothermic melt event was observed at 193.5° C., followed by immediate decomposition.

Figure 9:
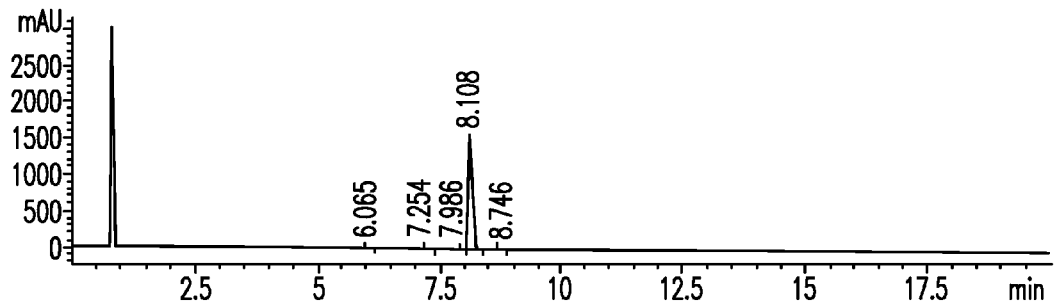
FIG. 9 depicts high performance liquid chromatography coupled with mass spectrometry of Form 2.
Figure 9:
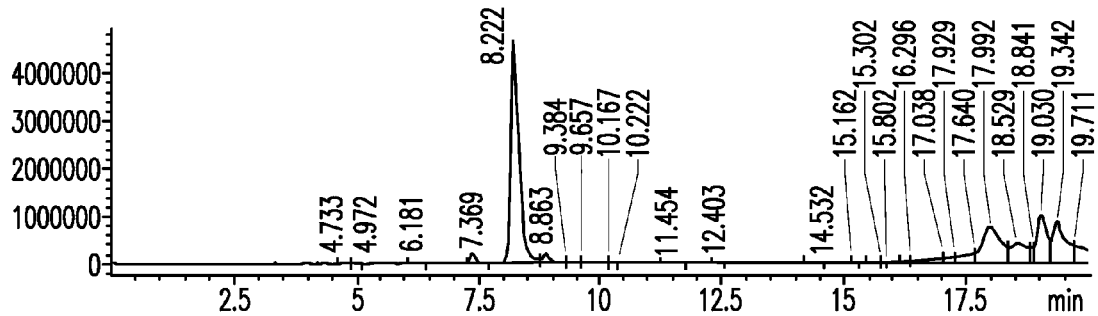

FIG. 9 provides HPLC and MS data of Form 2. The peak retention time is 8.1 minutes. The HPLC data indicates that the sample purity is 98.9% (area %).

Figure 10:
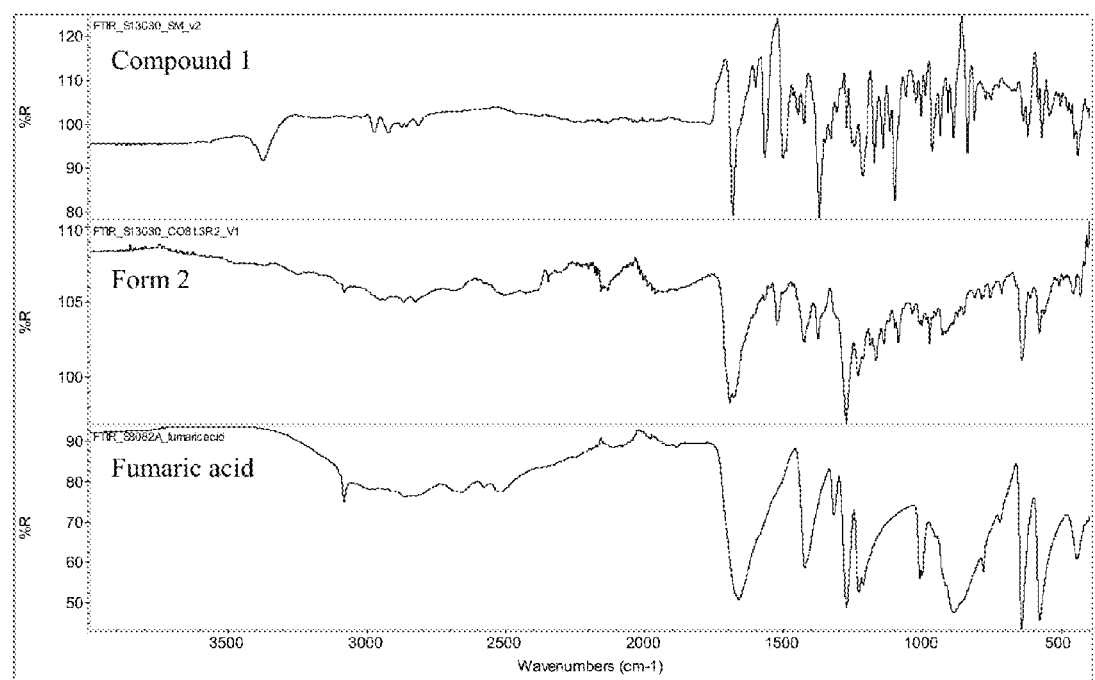
FIG. 10 depicts a fourier transform infrared spectroscopy (FTIR) overlay of Compound 1, Form 2 and fumaric acid.

FIG. 10 provides an FTIR overlay of Compound 1 (top), Form 2 (middle) and fumaric acid (bottom). The overlay indicates that the main shifts take place in the spectra in the region 1800-1500 $cm^{-1}$ and 1600-1400 $cm^{-1}$.

Figure 11:
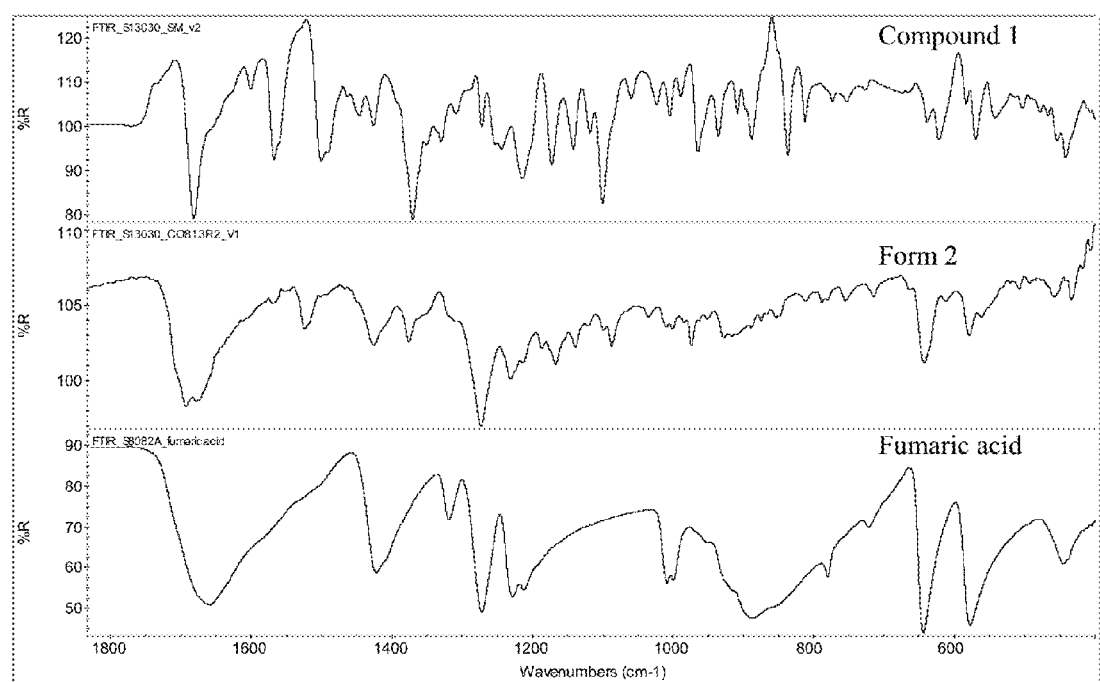
FIG. 11 depicts a FTIR overlay of Compound 1, Form 2 and fumaric acid in the region of 1800-400 $cm^{-1}$.

FIG. 11 provides an FTIR overlay of Compound 1 (top), Form 2 (middle) and fumaric acid (bottom) in the region of 1800-400 $cm^{-1}$. The overlay emphasizes the area between 1800-1500 $cm^{-1}$ and 1600-1400 $cm^{-1}$ corresponding to tertiary amines shifts where the H-bonding is taking place between the coformer and Compound 1. FIG. 10 and FIG. 11 clearly show a doubled shift at around 1800-1600 $cm^{-1}$ indicating the interaction of two molecules of fumaric acid with the nitrogens of Compound 1.

The crystal structure of Form 2 was successfully determined from the single crystal X-ray diffraction data. Compound 1 is protonated and forms a fumarate salt; the salt is also H-bonded with another molecule of fumaric acid forming a fumarate co-crystal of a fumarate salt. Moreover, a water molecule was also determined forming H-bonds with Compound 1. FIG. 12 provides a representative way of the bonds formed by Compound 1 with fumaric acid and water. FIG. 12 depicts the molecular structure and atom numbering scheme for protonated Compound 1 and its chemical first co-ordination sphere with nitrogen 13(b) being protonated (see FIG. 12).

The crystal structure of Form 2 comprises of 5 chemically different components: Compound 1 as free base, Compound 1 with protonated nitrogen atom named nitrogen 13(b), fumaric acid, fumarate anion and water. These components exist in the following ratio: 1 (Compound 1):1 (Compound 1·H$^+$):1.5 (fumaric acid):1 (fumaric acid anion):1 (water).

FIG. 13 shows the crystal packing and H-bond scheme of Form 2. Different components found in the asymmetric unit are marked by different colors (Compound 1·H$^+$-green, Compound 1—red, fumaric acid-blue, fumaric acid anion—orange and water—purple).

The H-bond pattern is presented below in Table 14. The closed packing has almost no void for solvent molecules besides water. The fumaric acid bonds to Compound 1 tertiary nitrogens to form the fumarate co-crystal. The fumarate salt is also formed at a nitrogen atom (N13b).

TABLE 14

Hydrogen bonds formed by Form 2

| D-H . . . A | D-H [Å] | H . . . A [Å] | D . . . A [Å] | D-H . . . A [°] |
|---|---|---|---|---|
| O(1A)-H(1A) . . . O(1) | 0.83(3) | 1.96(3) | 2.779(2) | 173(2) |
| N(15A)-H(15A) . . . O(37B)$^i$ | 0.89(2) | 2.03(2) | 2.916(2) | 172(2) |
| O(1B)-H(1B) . . . O(1A) | 0.88(3) | 1.96(3) | 2.825(2) | 169(2) |
| N(13B)-H(13B) . . . O(32B) | 0.98(2) | 1.65(2) | 2.619(2) | 172(2) |
| N(15B)-H(15B) . . . O(31B) | 0.88(2) | 1.94(2) | 2.810(2) | 172(2) |
| O(38A)-H(38A) . . . N(6A)$^{ii}$ | 0.89(4) | 1.88(4) | 2.736(2) | 162(3) |
| O(32A)-H(32A) . . . N(6B) | 0.91(4) | 1.81(4) | 2.713(2) | 170(3) |
| O(38B)-H(38B) . . . N(13A)$^{iii}$ | 0.93(3) | 1.72(3) | 2.636(2) | 168(2) |
| O(31C)-H(31C) . . . O(32B)$^{iv}$ | 0.90(3) | 1.72(3) | 2.616(2) | 175(3) |
| O(1)-HW1 . . . O(31B)$^{iv}$ | 0.87(3) | 1.96(3) | 2.808(2) | 164(3) |
| O(1)-HW2 . . . O(26A)$^v$ | 0.85(4) | 2.03(4) | 2.854(2) | 164(3) |

Symmetry transformations:
$^i$x − 1, y − 1, z − 1;
$^{ii}$x − 1, y + 1, z;
$^{iii}$x + 1, y + 1, z + 1;
$^{iv}$2 − x, 2 − y, 1 − z;
$^v$x, y + 1, z Table 15 shows that Form 2 is crystallizing in a triclinic symmetry with P-1 space group and having a Z equal to 2.

TABLE 15

Crystal structure data of Form 2

| | |
|---|---|
| Empirical formula | $C_{21}H_{28}N_5O_3^+ \cdot C_4H_3O_4^- \cdot C_{21}H_{27}N_5O_3 \cdot 1.5 (C_4H_4O_4) \cdot H_2O$ |
| F.W. | 1103.15 |
| T [K] | 296(2) |
| λ [Å] | 0.71073 |
| Crystal system | Triclinic |
| Space group | P-1 |
| Unit cell dimensions | |
| a [Å] | 11.0259(6) |
| b [Å] | 12.0731(6) |
| c [Å] | 21.0851(9) |
| α [°] | 98.862(3) |
| β [°] | 91.681(3) |
| γ [°] | 94.433(3) |
| V [Å] | 2762.6(2) |
| Z | 2 |
| $D_c$ [g/cm$^3$] | 1.326 |
| μ [mm$^{-1}$] | 0.100 |
| F(000) | 1168 |
| Crystal size [mm$^3$] | 0.35 × 0.32 × 0.25 |
| θ range for data collection [°] | 3 to 32.7 |
| Reflections collected | 28571 |
| Independent reflections | 19825 [$R_{int}$ is 0.0275] |
| Completeness to θ is 32.7° [%] | 97.8 |
| Max. and min. transmission | 0.9753 and 0.9657 |
| Data/restraints/parameters | 19825/0/1006 |
| Goodness-of-fit on F$^2$ | 1.035 |
| Final R indices [I > 2 (I)] | R1 is 0.0685, wR2 is 0.1682 |
| R indices (all data) | R1 is 0.1082, wR2 is 0.2022 |

Figure 14:
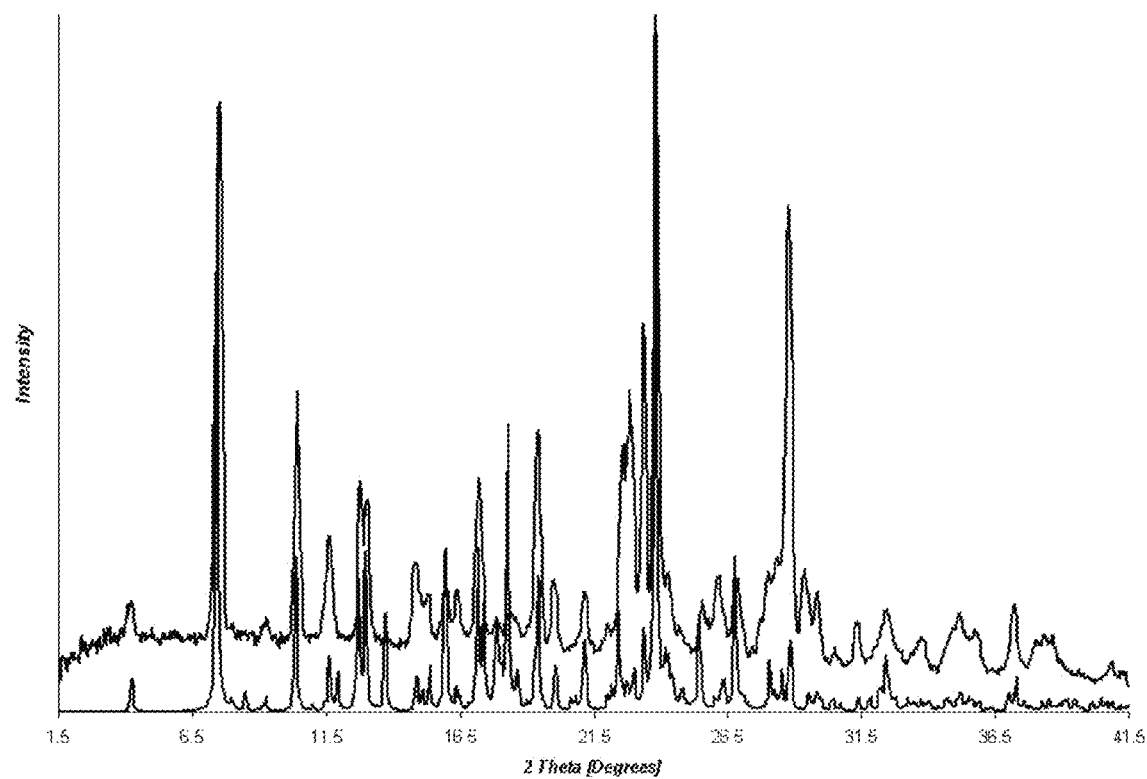
FIG. 14 depicts an overlay of the simulated XRPD pattern (bottom) and the experimental XRPD pattern (top) of Form 2.

FIG. 14 shows an overlay between the experimental data (red) recorded for Form 2 and the simulated XRPD data (black) from the determined crystal structure. The fit emphasizes the successful crystal structure determination of Form 2.

6.3.7 Cocrystal Solid Form 3

Form 3 was prepared in slurry experiments when benzoic acid was used as the coformer and water was used as the solvent. Form 3 is a hydrated cocrystal form of Compound 1 and benzoic acid.

FIG. 15 provides an overlay of XRPD patterns of Compound 1, Form 3, Form 4 and benzoic acid (from bottom to top). A list of X-Ray Diffraction Peaks for Form 3 is provided below in Table 16.

TABLE 16

X-Ray Diffraction Peaks for Form 3

| Two-theta angle (°) | d Space (Å) | Relative Intensity (%) |
|---|---|---|
| 7.3 | 12.1 | 69.57 |
| 8.02 | 11.01 | 14.1 |
| 11.86 | 7.45 | 24.84 |
| 12.78 | 6.92 | 46.84 |
| 14.38 | 6.15 | 18.41 |
| 16.9 | 5.24 | 24.27 |
| 18.74 | 4.73 | 20.06 |
| 21.14 | 4.2 | 18.24 |
| 21.9 | 4.05 | 80.08 |
| 23.78 | 3.74 | 18.47 |
| 25.14 | 3.54 | 19.88 |
| 25.82 | 3.45 | 8.81 |
| 26.74 | 3.33 | 18.86 |

FIG. 16 and FIG. 17 provide TGMS data and TGA/SDTA data of Form 3. between 25° C. and 100° C. when heated from 25° C. to 300° C. According to the SDTA signal in FIG. 17, three endothermic melt event were observed at 67.7° C., 108° C. and 158° C. indicating a possible dehydration step followed by melting and decomposition.

Figure 18:
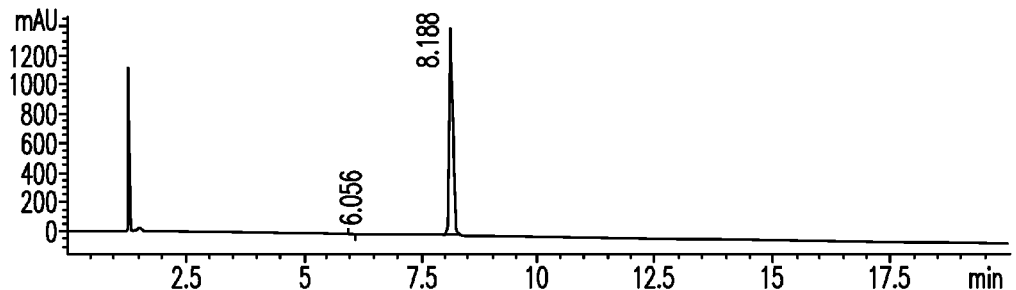
FIG. 18 depicts high performance liquid chromatography coupled with mass spectrometry of Form 3.
Figure 18:
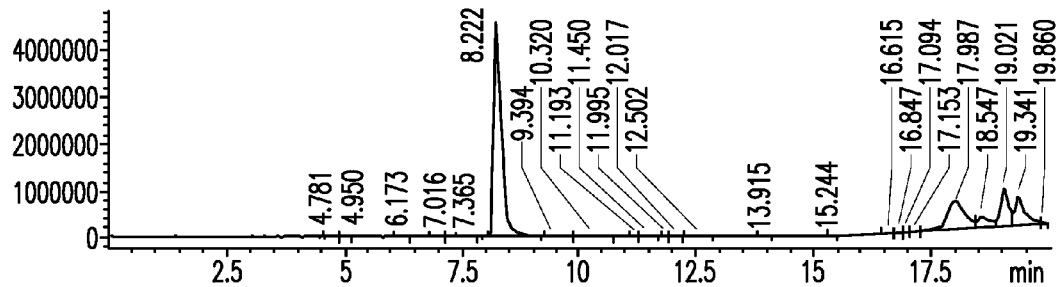

FIG. 18 provides HPLC and MS data of Form 3. The peak retention time is 8.1 minutes. The HPLC data indicates that the sample purity is 99.9% (area %).

Figure 19:
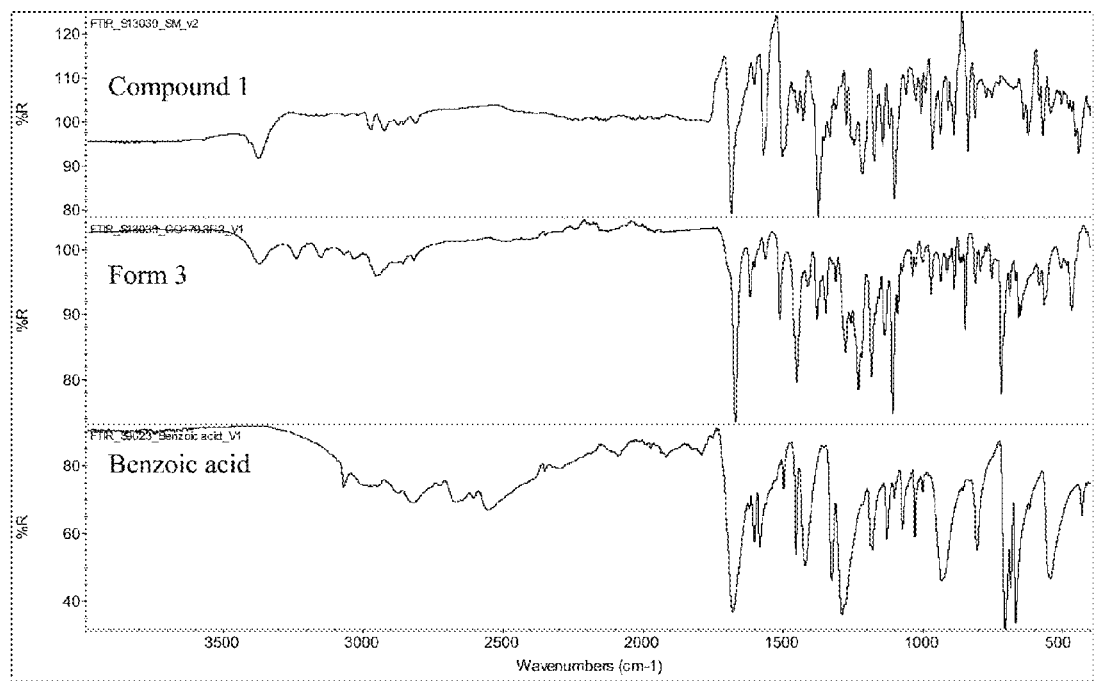
FIG. 19 depicts a FTIR overlay of Compound 1, Form 3 and benzoic acid.

FIG. 19 provides an FTIR overlay of Compound 1 (top), Form 3 (middle) and benzoic acid (bottom). The overlay indicates that the main shifts take place in the spectra in the region 1800-1500 cm$^{-1}$ and 1600-1400 cm$^{-1}$.

Figure 20:
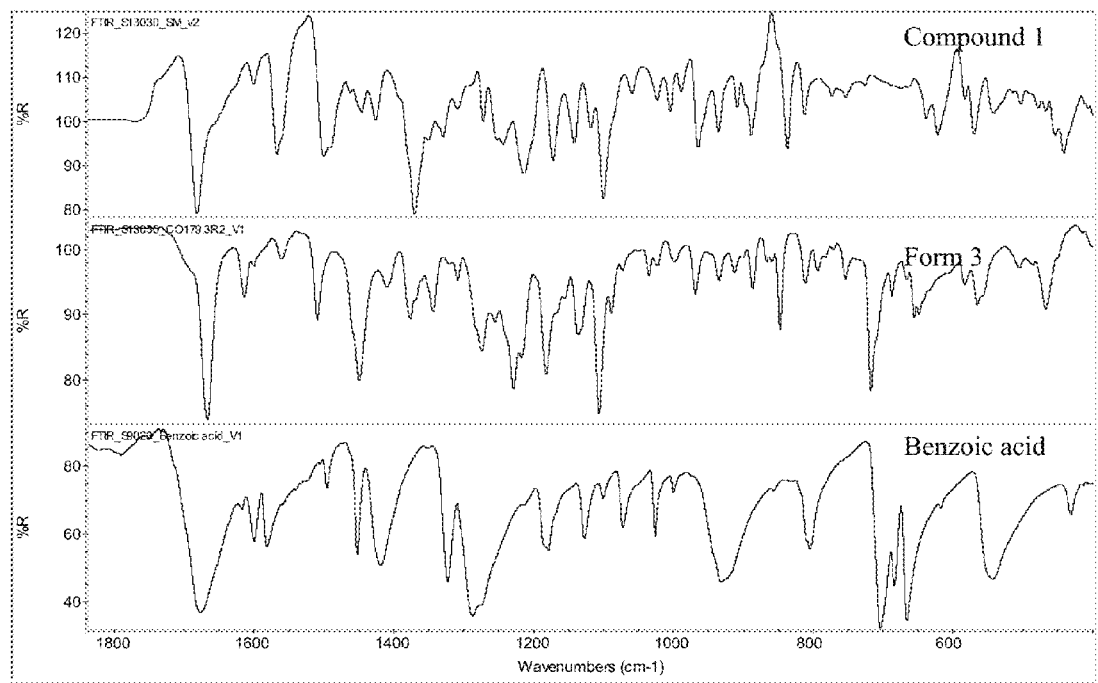
FIG. 20 depicts a FTIR overlay of Compound 1, Form 3 and benzoic acid in the region of 1800-400 cm$^{-1}$.

FIG. 20 provides an FTIR overlay of Compound 1 (top), Form 3 (middle) and benzoic acid (bottom) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.8 Cocrystal Solid Form 4

Form 4 was prepared in slurry experiments when benzoic acid was used as the coformer and a mixture of acetone and water (10/90) was used as the solvent. Form 4 is an acetone solvated cocrystal form of Compound 1 and benzoic acid.

FIG. 15 provides an overlay of XRPD patterns of Compound 1, Form 3, Form 4 and benzoic acid (from bottom to top). A list of X-Ray Diffraction Peaks for Form 4 is provided below in Table 17.

TABLE 17

X-Ray Diffraction Peaks for Form 4

| Two-theta angle (°) | d Space (Å) | Relative Intensity (%) |
|---|---|---|
| 8.02 | 11.01 | 52.13 |
| 8.86 | 9.97 | 14.72 |
| 9.74 | 9.07 | 18.4 |
| 12.78 | 6.92 | 17.12 |
| 13.82 | 6.4 | 54.86 |
| 15.58 | 5.68 | 45.57 |
| 17.94 | 4.94 | 18 |
| 19.82 | 4.47 | 46.44 |
| 20.5 | 4.33 | 10.22 |
| 21.02 | 4.22 | 32.95 |
| 22.58 | 3.93 | 9.81 |
| 24.38 | 3.65 | 25.92 |
| 25.02 | 3.55 | 90.27 |
| 27.66 | 3.22 | 15.92 |

FIG. 21 and FIG. 22 provide TGMS data and TGA/SDTA data of Form 4. A mass loss of 1.7% corresponding to acetone was observed between 35° C. and 110° C. during an endothermic event with T$_{peak}$ at 83.2° C., suggesting the solvated nature of the sample, when heated from 25° C. to 300° C. According to the SDTA signal in FIG. 22, an endothermic melt event was observed at 83.2° C., followed by decomposition starting from 180° C.

Figure 23:
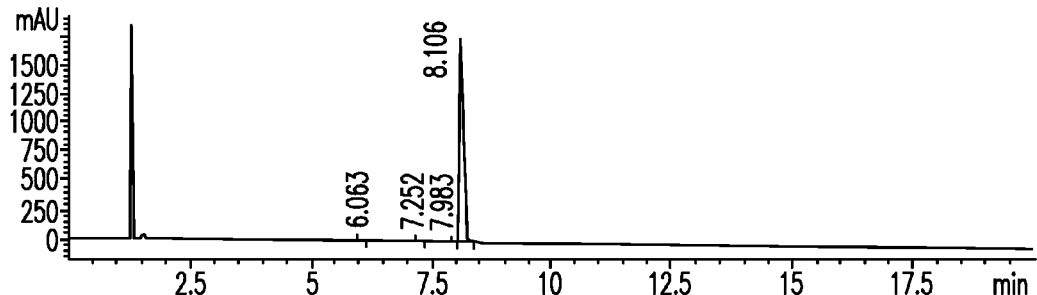
FIG. 23 depicts high performance liquid chromatography coupled with mass spectrometry of Form 4.
Figure 23:
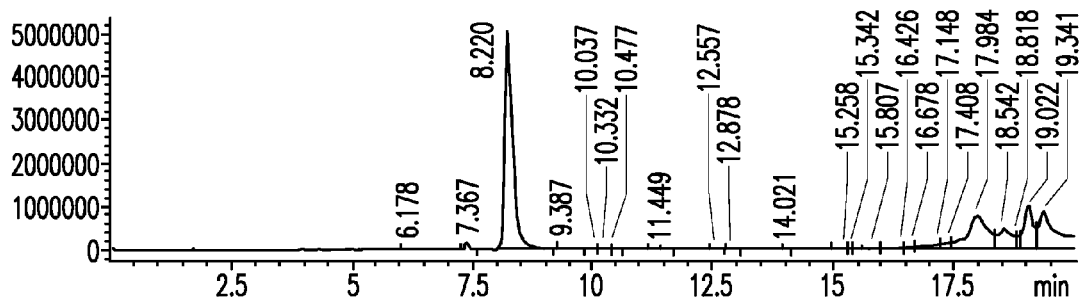

FIG. 23 provides HPLC and MS data of Form 4. The peak retention time is 8.1 minutes. The HPLC data indicates that the sample purity is 99.4% (area %).

Figure 24:
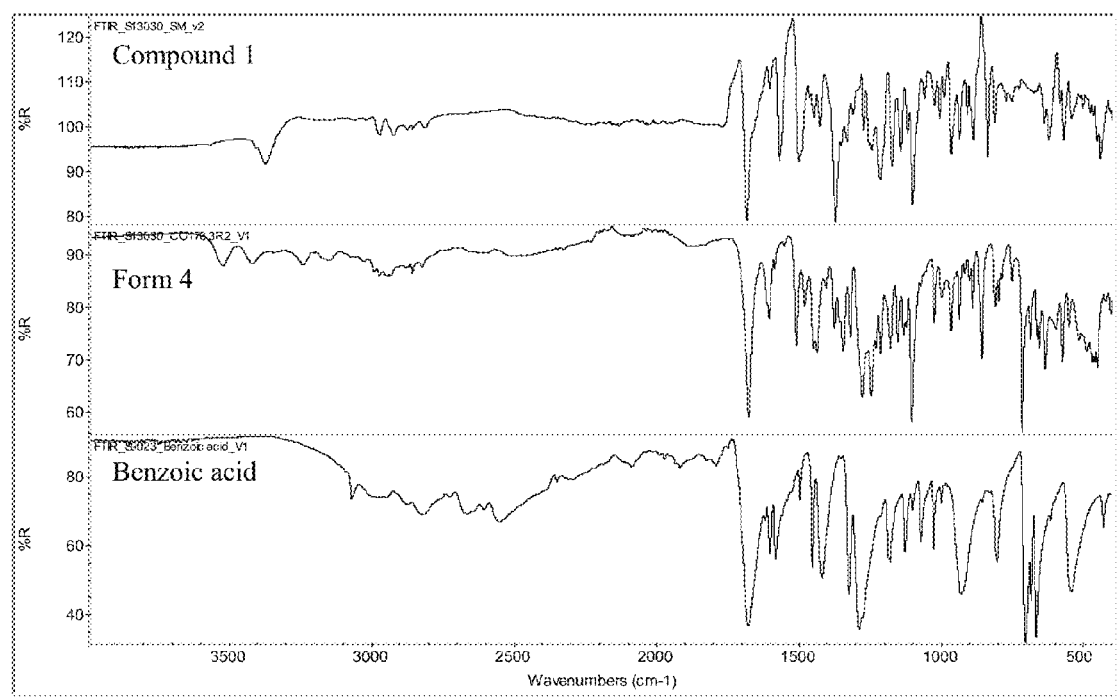
FIG. 24 depicts a FTIR overlay of Compound 1, Form 4 and benzoic acid.

FIG. 24 provides an FTIR overlay of Compound 1 (top), Form 4 (middle) and benzoic acid (bottom). The overlay indicates that the main shifts take place in the spectra in the region 1800-1500 cm$^{-1}$ and 1600-1400 cm$^{-1}$.

Figure 25:
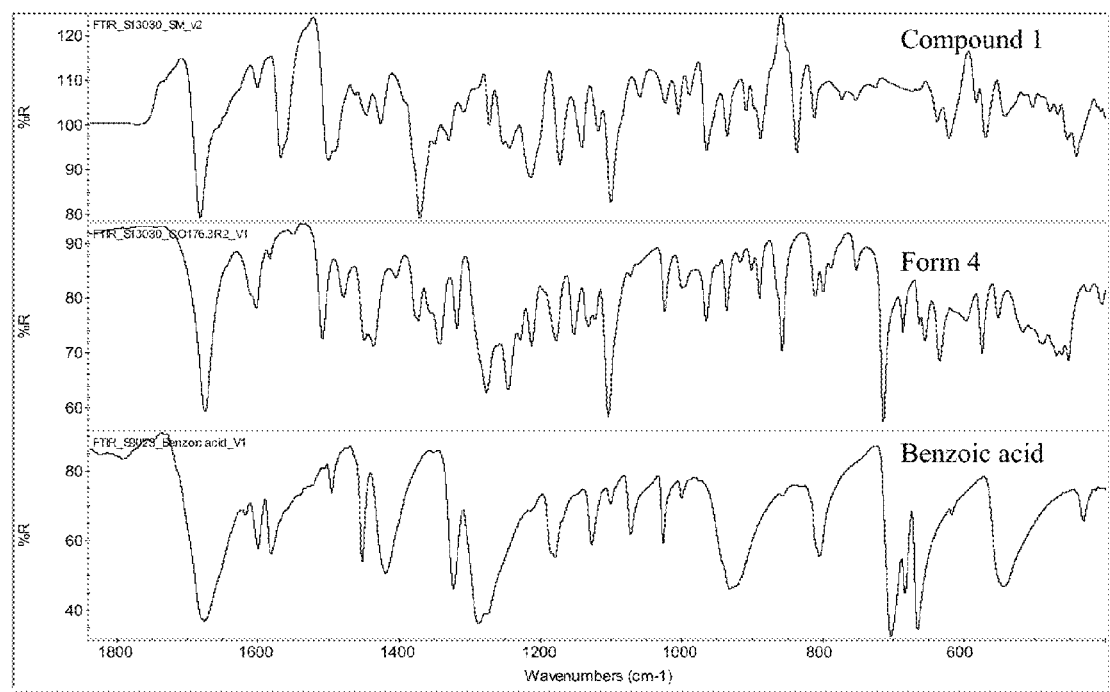
FIG. 25 depicts a FTIR overlay of Compound 1, Form 4 and benzoic acid in the region of 1800-400 cm$^{-1}$.

FIG. 25 provides an FTIR overlay of Compound 1 (top), Form 4 (middle) and benzoic acid (bottom) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.9 Cocrystal Solid Form 5

Form 5 was prepared in slurry experiments when gentisic acid was used as the coformer and a mixture of acetone and water (10/90) was used as the solvent. Form 5 is an acetone and water solvated cocrystal form of Compound 1 and gentisic acid.

FIG. 26 provides an overlay of XRPD patterns of Compound 1, Form 5, Form 6 and gentisic acid (from bottom to top). A list of X-Ray Diffraction Peaks for Form 5 is provided below in Table 18.

TABLE 18

X-Ray Diffraction Peaks for Form 5

| Two-theta angle (°) | d Space (Å) | Relative Intensity (%) |
|---|---|---|
| 4.1 | 21.53 | 82.42 |
| 6.34 | 13.92 | 11.62 |
| 8.3 | 10.64 | 11.9 |
| 15.78 | 5.61 | 21.32 |
| 20.06 | 4.42 | 18.44 |
| 20.7 | 4.29 | 11.59 |
| 25.78 | 3.45 | 66.24 |

FIG. 27 and FIG. 28 provide TGMS data and TGA/SDTA data of Form 5. A mass loss of 4.6% between 25° C. and 120° C. corresponding to water and acetone was observed suggesting the solvated nature of the sample, when heated from 25° C. to 300° C. According to the SDTA signal in FIG. 28, an endothermic melt event was observed at 95.5° C., followed by decomposition starting from 180° C.

Figure 29:
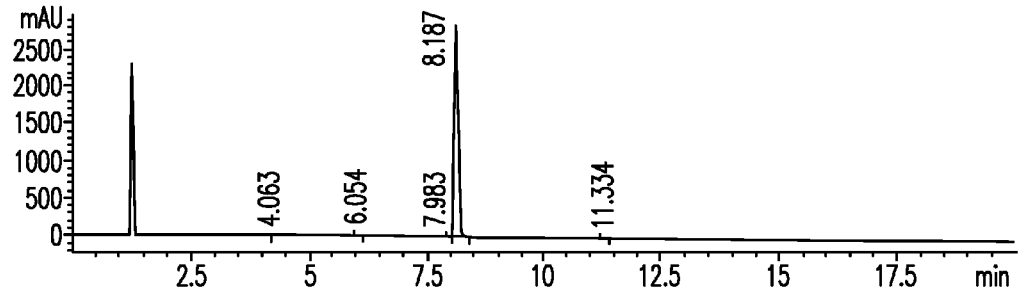
FIG. 29 depicts high performance liquid chromatography coupled with mass spectrometry of Form 5.
Figure 29:
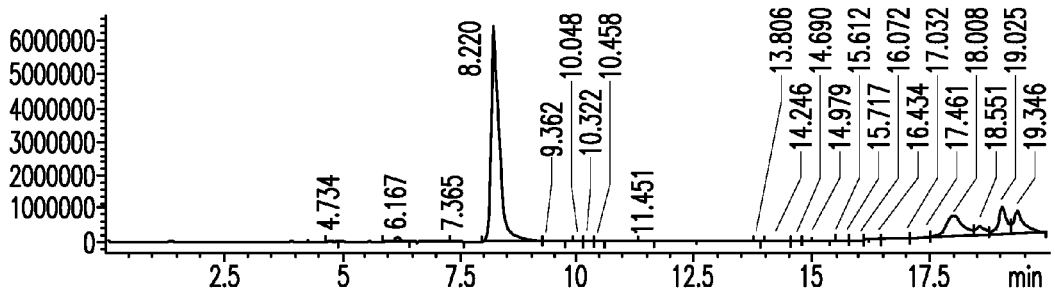

FIG. 29 provides HPLC and MS data of Form 5. The peak retention time is 8.1 minutes. The HPLC data indicates that the sample purity is 99.4% (area %).

Figure 30:
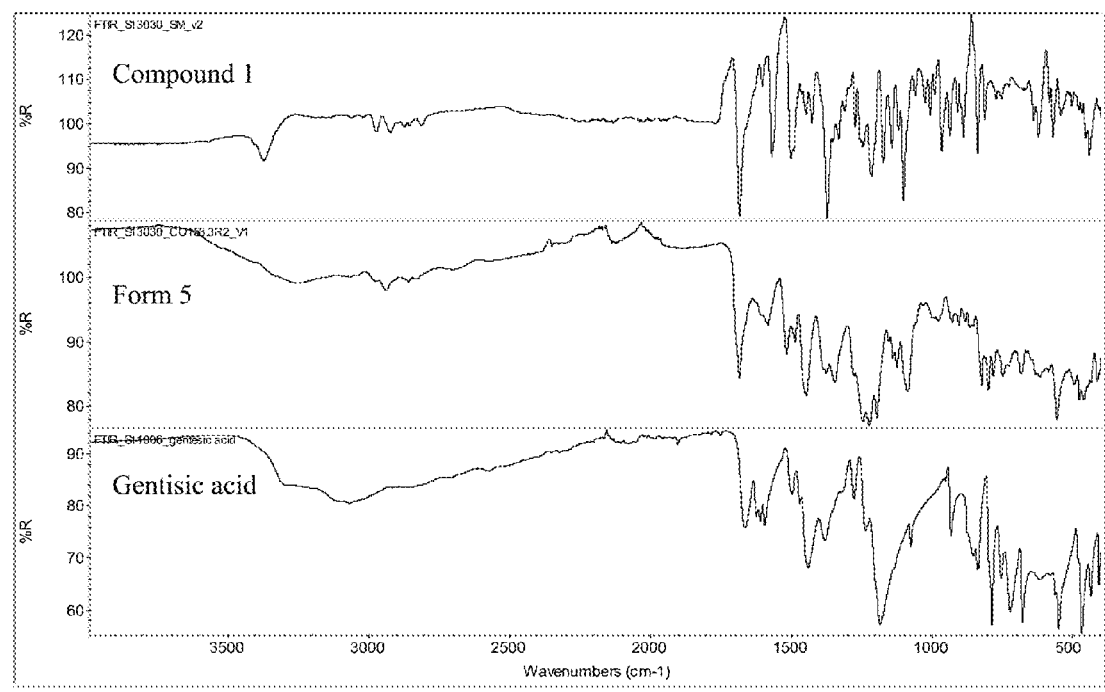
FIG. 30 depicts a fourier transform infrared spectroscopy (FTIR) overlay of Compound 1, Form 5 and gentisic acid.

FIG. 30 provides an FTIR overlay of Compound 1 (top), Form 5 (middle) and gentisic acid (bottom). The overlay indicates that the main shifts take place in the spectra in the region 1800-1500 cm$^{-1}$ and 1600-1400 cm$^{-1}$.

Figure 31:
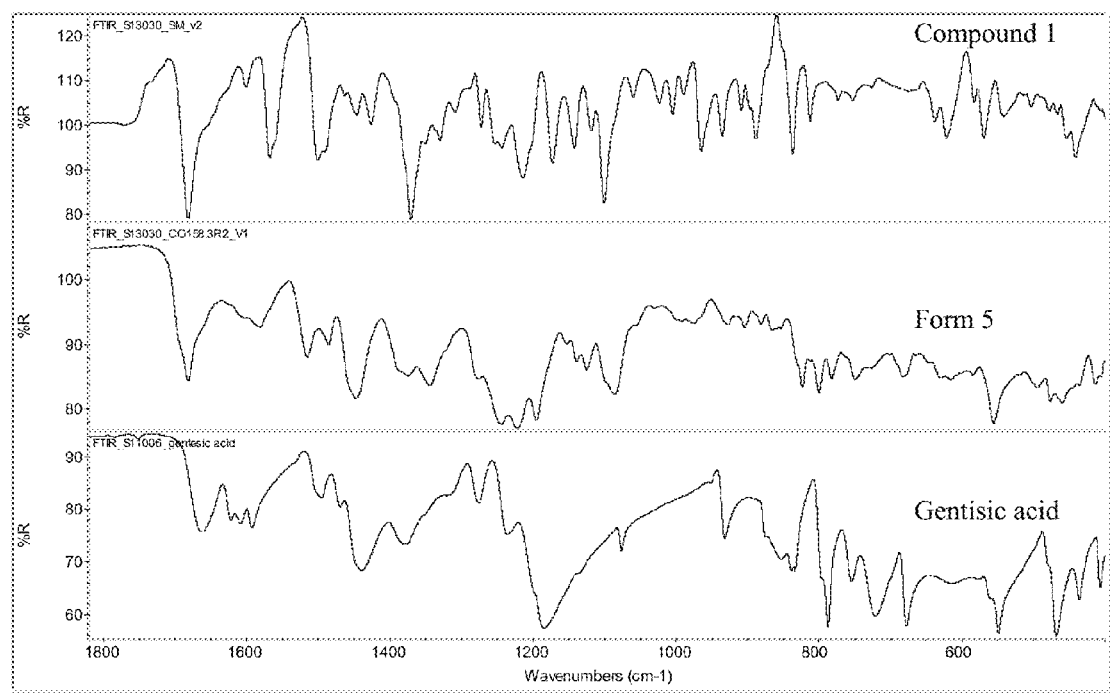
FIG. 31 depicts a FTIR overlay of Compound 1, Form 5 and gentisic acid in the region of 1800-400 cm$^{-1}$.

FIG. 31 provides an FTIR overlay of Compound 1 (compound), Form 5 (middle) and gentisic acid (bottom) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.10 Cocrystal Solid Form 6

Form 6 was prepared in slurry experiments when gentisic acid was used as the coformer and acetonitrile was used as the solvent. Form 6 is an acetonitrile solvated cocrystal form of Compound 1 and gentisic acid.

FIG. 26 provides an overlay of XRPD patterns of Compound 1, Form 5, Form 6 and gentisic acid (from bottom to top). A list of X-Ray Diffraction Peaks for Form 6 is provided below in Table 19.

TABLE 19

X-Ray Diffraction Peaks for Form 6

| Two-theta angle (°) | d Space (Å) | Relative Intensity (%) |
|---|---|---|
| 4.26 | 20.72 | 80.42 |
| 13.02 | 6.79 | 16.8 |
| 13.5 | 6.55 | 16.09 |
| 14.22 | 6.22 | 12.52 |
| 17.78 | 4.98 | 54.7 |
| 19.22 | 4.61 | 14.68 |
| 21.7 | 4.09 | 33.93 |
| 25.82 | 3.45 | 70.97 |

FIG. 32 provides TGMS data of Form 6. A mass loss of 0.9% corresponding to acetonitrile was observed between 70° C. and 160° C. during an endothermic event with $T_{peak}$ at 148° C. suggesting the solvated nature of the sample, when heated from 25° C. to 300° C. According to the SDTA signal in FIG. 33, an endothermic melt event was observed at the above mentioned temperatures, 148° C., followed by immediate decomposition.

Figure 34:
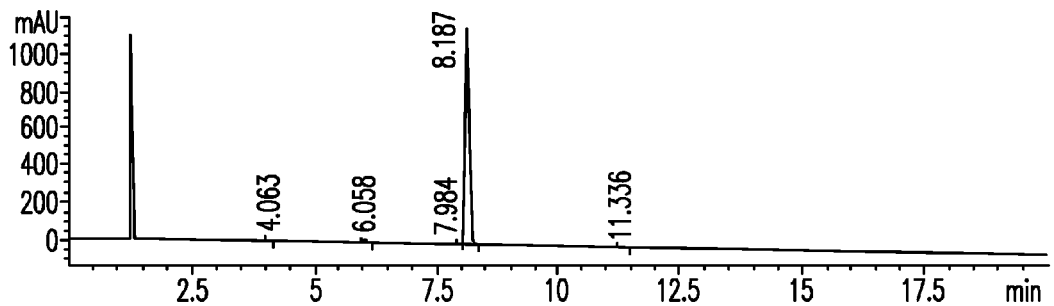
FIG. 34 depicts high performance liquid chromatography coupled with mass spectrometry of Form 6.
Figure 34:
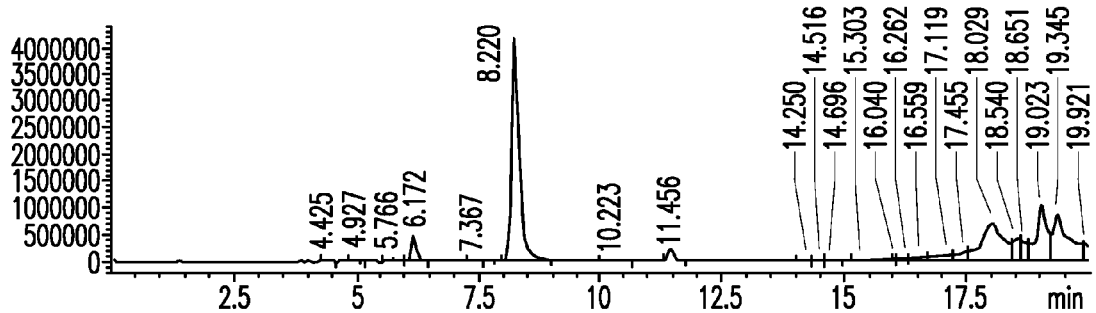

FIG. 34 provides HPLC and MS data of Form 6. The peak retention time is 8.1 minutes. The HPLC data indicates that the sample purity is 96.6% (area %).

Figure 35:
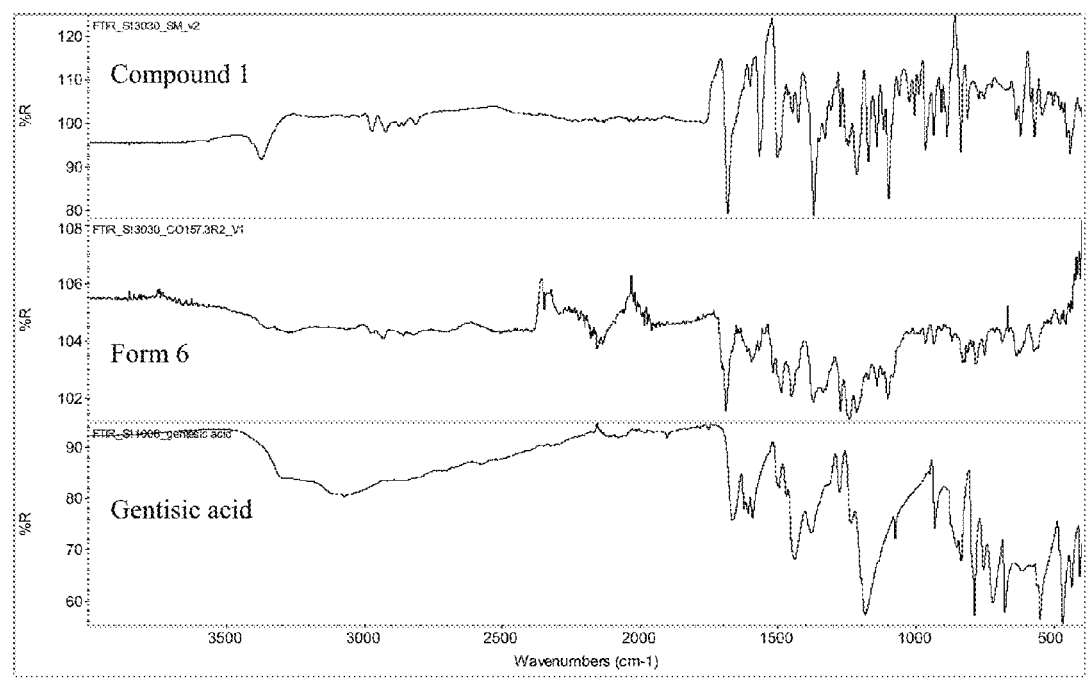
FIG. 35 depicts a fourier transform infrared spectroscopy (FTIR) overlay of Compound 1, Form 6 and gentisic acid.

FIG. 35 provides an FTIR overlay of Compound 1 (top), Form 6 (middle) and gentisic acid (bottom). The overlay indicates that the main shifts take place in the spectra in the region 1800-1500 cm$^{-1}$ and 1600-1400 cm$^{-1}$.

Figure 36:
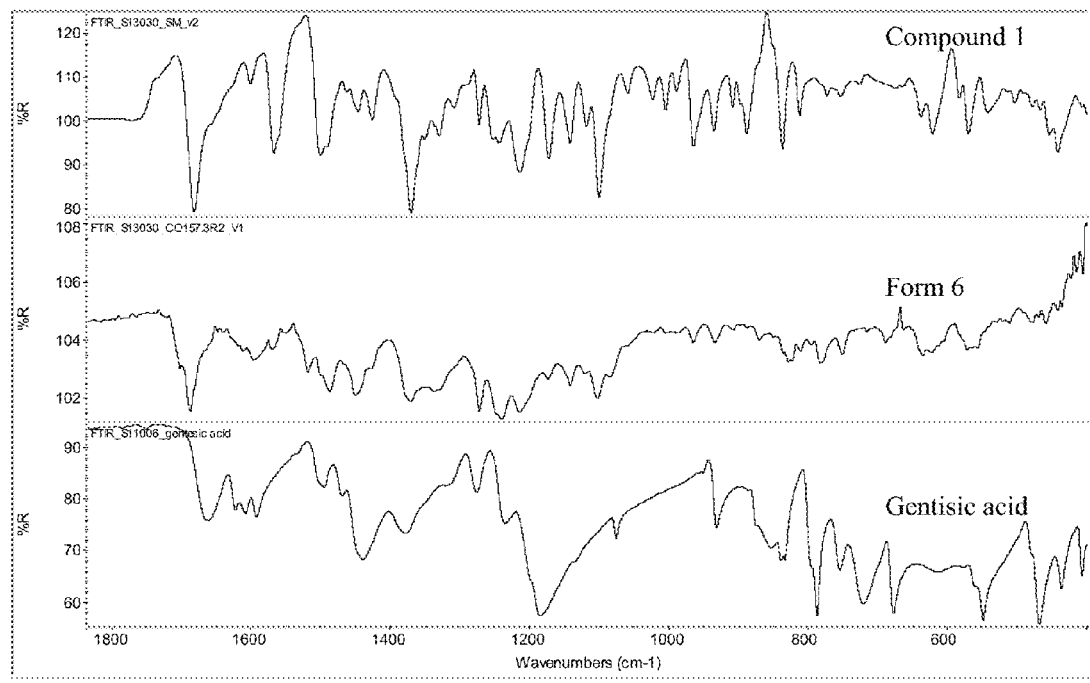
FIG. 36 depicts a FTIR overlay of Compound 1, Form 6 and gentisic acid in the region of 1800-400 cm$^{-1}$.

FIG. 36 provides an FTIR overlay of Compound 1 (top), Form 6 (middle) and gentisic acid (bottom) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.11 Cocrystal Solid Form 7

Form 7 was prepared in slurry experiments when maleic acid was used as the coformer and acetonitrile was used as the solvent. Form 7 is an acetonitrile and water solvated cocrystal form of Compound 1 and maleic acid.

FIG. 37 provides an overlay of XRPD patterns of Compound 1, Form 7, Form 8 and maleic acid (from bottom to top). A list of X-Ray Diffraction Peaks for Form 7 is provided below in Table 20.

TABLE 20

X-Ray Diffraction Peaks for Form 7

| Two-theta angle (°) | d Space (Å) | Relative Intensity (%) |
|---|---|---|
| 6.54 | 13.5 | 91.09 |
| 9.42 | 9.38 | 15.17 |
| 13.66 | 6.47 | 25.83 |
| 18.42 | 4.81 | 20.05 |
| 26.02 | 3.42 | 55.38 |
| 26.82 | 3.32 | 18.98 |

FIG. 38 provide TGMS data of Form 7. A mass loss of 4% corresponding to water and acetonitrile was observed between 35° C. and 110° C. during an endothermic event with $T_{peak}$ at 86° C., suggesting the solvated nature of the sample, when heated from 25° C. to 300° C. According to the SDTA signal in FIG. 39, an endothermic melt event was observed at 86° C., followed by decomposition starting from 115° C.

Figure 40:
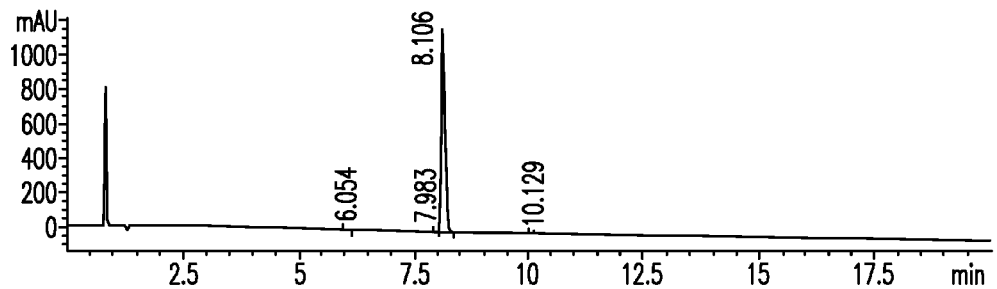
FIG. 40 depicts high performance liquid chromatography coupled with mass spectrometry of Form 7.
Figure 40:
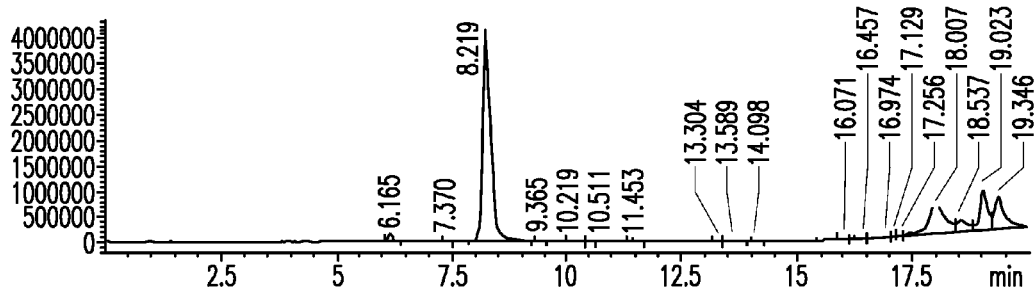

FIG. 40 provides HPLC and MS data of Form 7. The peak retention time is 8.1 minutes. The HPLC data indicates that the sample purity is 98.3% (area %).

Figure 41:
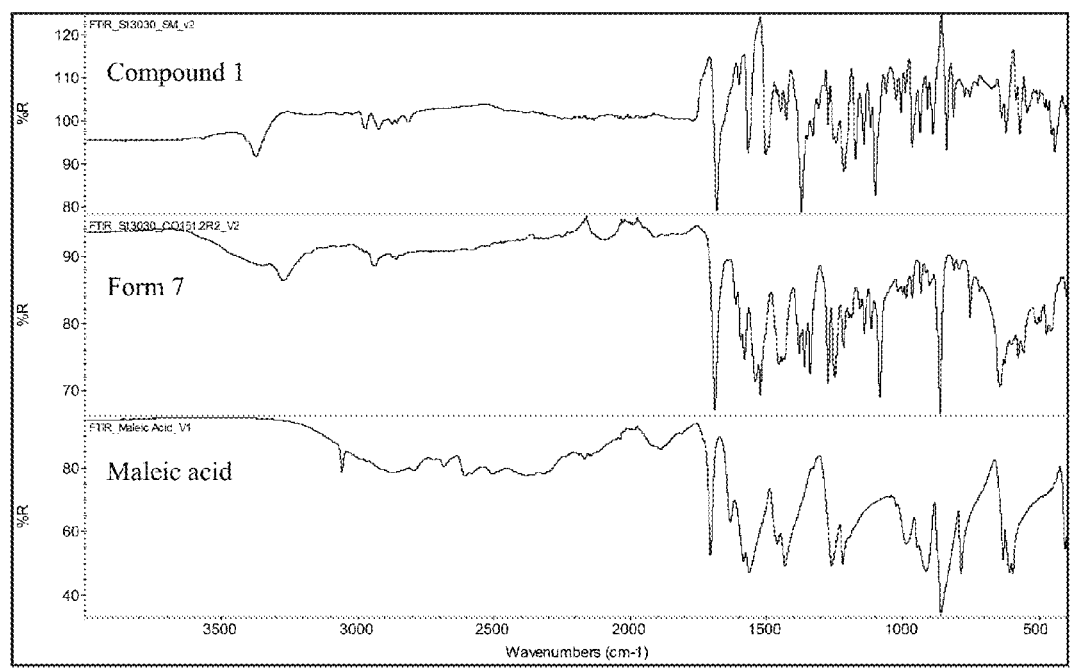
FIG. 41 depicts a fourier transform infrared spectroscopy (FTIR) overlay of Compound 1, Form 7 and maleic acid.

FIG. 41 provides an FTIR overlay of Compound 1 (top), Form 7 (middle) and maleic acid (bottom). The overlay indicates that the main shifts take place in the spectra in the region 1800-1500 cm$^{-1}$ and 1600-1400 cm$^{-1}$.

Figure 42:
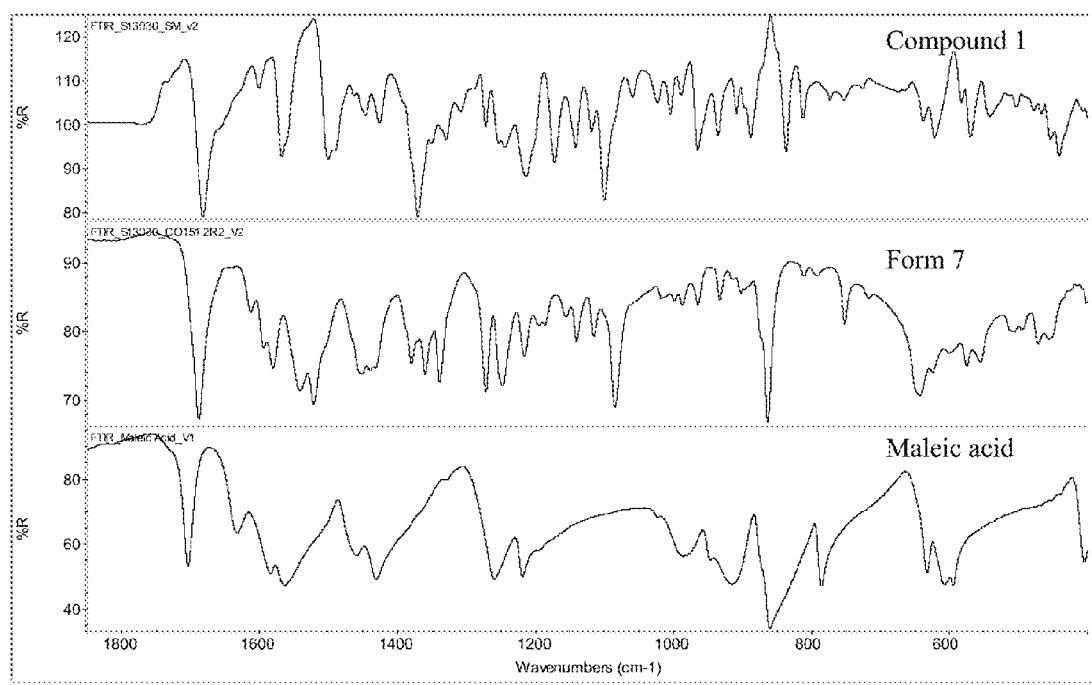
FIG. 42 depicts a FTIR overlay of Compound 1, Form 7 and maleic acid in the region of 1800-400 cm$^{-1}$.

FIG. 42 provides an FTIR overlay of Compound 1 (top), Form 7 (middle) and maleic acid (bottom) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.12 Cocrystal Solid Form 8

Form 8 was prepared in cooling evaporative experiments when maleic acid was used as the coformer and ethyl acetate was used as the solvent. Form 8 is an ethyl acetate solvated cocrystal form of Compound 1 and maleic acid.

FIG. 37 provides an overlay of XRPD patterns of Compound 1, Form 7, Form 8 and maleic acid (from bottom to top). A list of X-Ray Diffraction Peaks for Form 8 is provided below in Table 21.

TABLE 21

X-Ray Diffraction Peaks for Form 8

| Two-theta angle (°) | d Space (Å) | Relative Intensity (%) |
|---|---|---|
| 6.14 | 14.38 | 86.12 |
| 7.42 | 11.9 | 18.12 |
| 15.5 | 5.71 | 12.36 |
| 17.3 | 5.12 | 32.94 |
| 18.46 | 4.8 | 14.03 |
| 26.78 | 3.33 | 33.16 |
| 28.38 | 3.14 | 19.56 |

FIG. 43 provide TGMS data of Form 8. A mass loss of 1% corresponding to ethyl acetate was observed between 35° C. and 110° C. during an endothermic event with $T_{peak}$ at 118.8° C., suggesting the solvated nature of the sample, when heated from 25° C. to 300° C. According to the SDTA signal in FIG. 44, an endothermic event was observed at 118.8° C., followed by decomposition.

Figure 45:
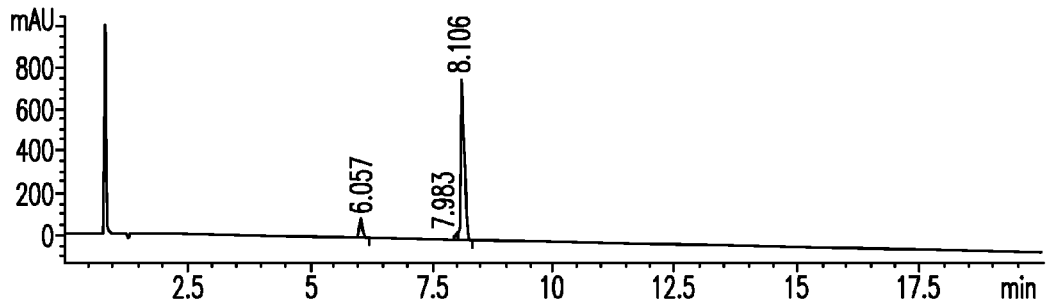
FIG. 45 depicts high performance liquid chromatography coupled with mass spectrometry of Form 8.
Figure 45:
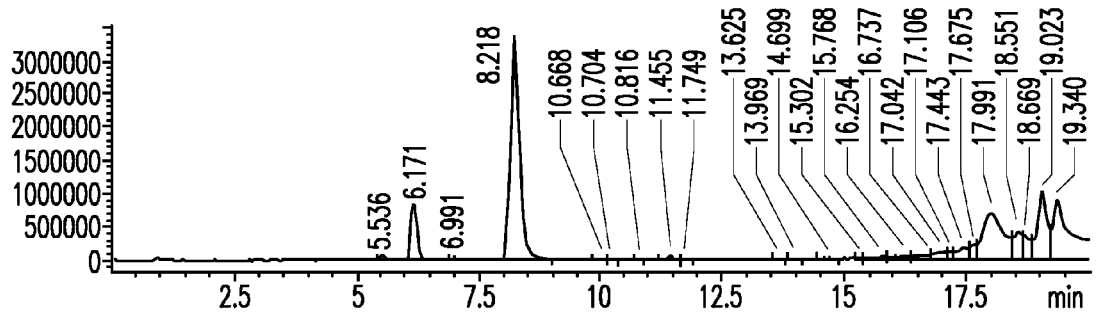

FIG. 45 provides HPLC and MS data of Form 8. The peak retention time is 8.1 minutes. The HPLC data indicates that the sample purity is 87.2% (area %).

Figure 46:
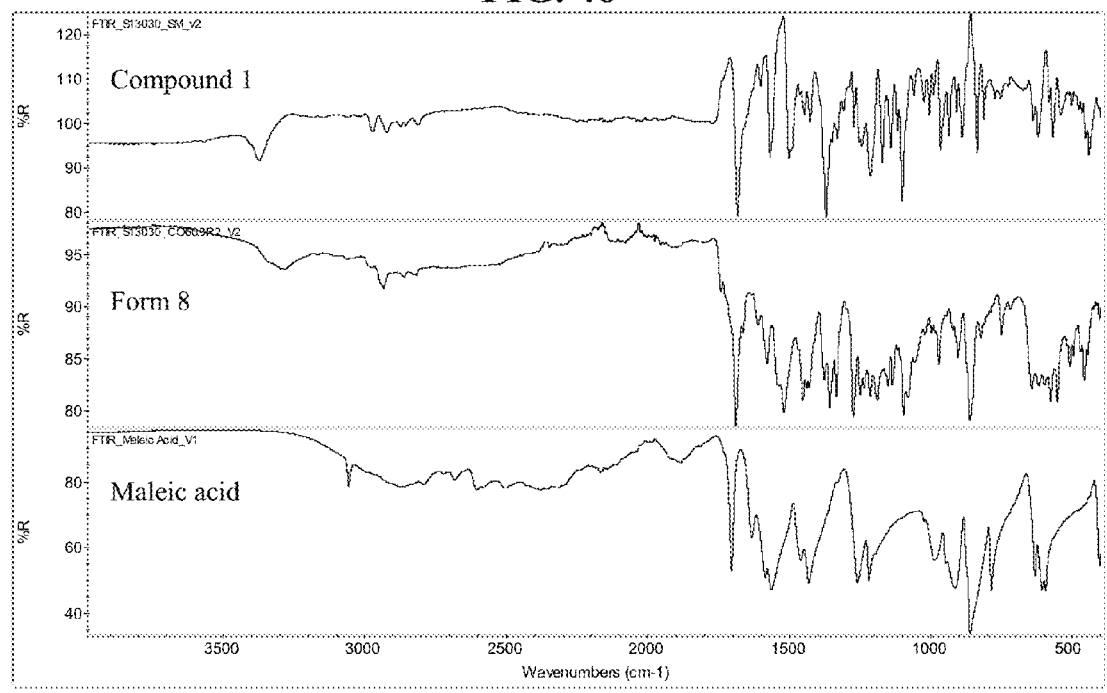
FIG. 46 depicts a fourier transform infrared spectroscopy (FTIR) overlay of Compound 1, Form 8 and maleic acid.

FIG. 46 provides an FTIR overlay of Compound 1 (top), Form 8 (middle) and maleic acid (bottom). The overlay indicates that the main shifts take place in the spectra in the region 1800-1500 cm$^{-1}$ and 1600-1400 cm$^{-1}$.

Figure 47:
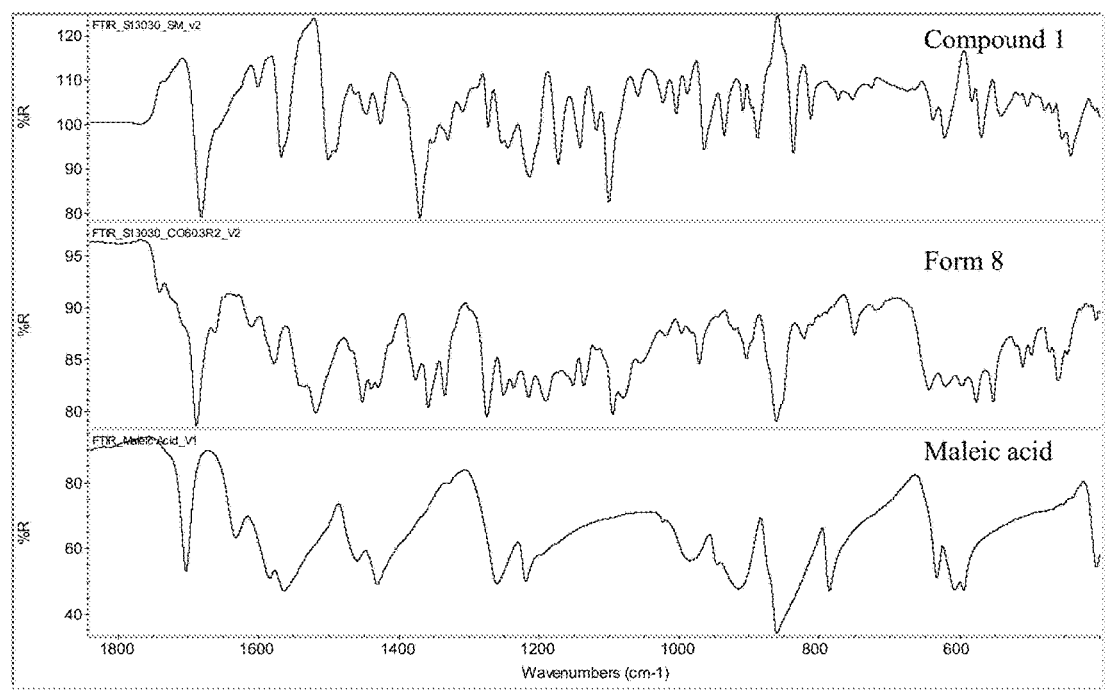
FIG. 47 depicts a FTIR overlay of Compound 1, Form 8 and maleic acid in the region of 1800-400 cm$^{-1}$.

FIG. 47 provides an FTIR overlay of Compound 1 (top), Form 8 (middle) and maleic acid (bottom) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.4 Biological Examples
6.4.1 Biochemical Assays

TOR HTR-FRET Assay. The following is an example of an assay that can be used to determine the TOR kinase inhibitory activity of solid forms of Compound 1. A solid form of Compound 1 is dissolved in DMSO and prepared as 10 mM stocks and diluted appropriately for the experiments. Reagents are prepared as follows:

"Simple TOR buffer" (used to dilute high glycerol TOR fraction): 10 mM Tris pH 7.4, 100 mM NaCl, 0.1% Tween-20, 1 mM DTT. Invitrogen recombinant TOR enzyme (cat #PV4753) is diluted in this buffer to an assay concentration of 0.200 µg/mL.

ATP/Substrate solution: 0.075 mM ATP, 12.5 mM MnCl$_2$, 50 mM Hepes, pH 7.4, 50 mM β-GOP, 250 nM Microcystin LR, 0.25 mM EDTA, 5 mM DTT, and 3.5 µg/mL GST-p70S6.

Detection reagent solution: 50 mM HEPES, pH 7.4, 0.01% Triton X-100, 0.01% BSA, 0.1 mM EDTA, 12.7 µg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 µL of the Simple TOR buffer is added 0.5 µL of test solid form in DMSO. To initiate the reaction 5 µL of ATP/Substrate solution is added to 20 µL of the Simple TOR buffer solution (control) and to the compound solution prepared above. The assay is stopped after 60 minutes by adding 5 µL of a 60 mM EDTA solution; 10 µL of detection reagent solution is then added and the mixture is allowed to sit for at least 2 hours before reading on a Perkin-Elmer Envision Microplate Reader set to detect LANCE Eu TR-FRET (excitation at 320 µm and emission at 495/520 nm).

DNA-PK Assay.

DNA-PK assay is performed using the procedures supplied in the Promega DNA-PK assay kit (catalog #V7870). DNA-PK enzyme can be purchased from Promega (Promega cat#V5811).

6.5 Formulation Examples

Certain formulations comprising solid forms of Compound 1 are prepared and tested for a number of physical and chemical properties. Modifications are then made and subsequent formulations are also tested, until formulations possessing desirable physical and chemical properties are found. The following example describes these formulations and their testing.

A solid form of Compound 1 is formulated as tablets containing about 5 mg, 20 mg, and 50 mg of a solid form of Compound 1 as an active pharmaceutical ingredient. The excipients and carriers that are used in the tablet formulations are summarized in Table 22, along with their intended functions.

TABLE 22

Pharmaceutical Acceptable Excipients and Carriers

| Ingredients | Function |
|---|---|
| Lactose monohydrate, NF (Fast Flo 316) | Diluent |
| Microcrystalline cellulose, NF (Avicel pH 101) | Diluent/binder |
| Microcrystalline cellulose, NF (Avicel pH 102) | Diluent/binder |
| Corn starch, NF | Disintegrant/lubricant |
| Pregelatinized starch, NF (Starch 1500) | Binder/Disintegrant |
| Lactose anhydrous, NF | Diluent |
| Croscarmellose sodium, NF (Ac-Di-Sol) | Disintegrant |
| Stearic acid, NF | Lubricant |
| Magnesium Stearate, NF | Lubricant |

General Method for Tablet Preparation.

Tablets are produced at batch size ranging from 0.5 to 2.2 kg. A solid form of Compound 1 is first mixed/blended with binders, diluent(s), and/or disintegrant (e.g., lactose monohydrate (NF), croscarmellose sodium (NF), and/or microcrystalline cellulose (NF)) using a Globepharma 4-8 quart Bin Blender. The mixture is then sieved via 18 mesh screen. The sieved mixture is further mixed/blended with a Globepharma 4-8 quart Bin Blender. After lubricant(s) (e.g., stearic acid (NF) and/or magnesium stearate (NF)) are sieved via 30 mesh screen, the lubricant(s) are then added to the mixture. The resulting mixture is then mixed/blended with a Globepharma 4-8 quart Bin Blender. The mixture is then compressed into tablets with a rotary table press, and then coated in an Ohara 8" pan. The tablets thus produced are evaluated for their powder characteristics, tablet characteristics, drug product photostability/short term stability, and manufacturing process.

Tablet formulations I to VIII of a solid form of Compound 1 are summarized in Table 23 to Table 30. The process parameters for tablet preparation (blending/compression) are summarized in Table 31 and Table 32. The addition of stearic acid in Formulations V to VIII can improve lubrication without impacting disintegration and compressibility. Lactose monohydrate, NF (Fast Flo 316) can be used as an alternate diluent.

TABLE 23

Tablet Formulation I

| Ingredients | Amounts mg | % |
|---|---|---|
| A solid form of Compound 1 | 50.0 | 16.7 |
| Lactose monohydrate, NF (Fast Flo 316) | 145.1 | 48.3 |
| Microcrystalline cellulose, NF (Avicel pH 101) | 93.1 | 31.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 24

Tablet Formulation II

| Ingredients | Amounts mg | % |
|---|---|---|
| A solid form of Compound 1 | 50.0 | 16.7 |
| Lactose monohydrate, NF (Fast Flo 316) | 168.0 | 56.0 |
| Pregelatinized starch, NF (Starch 1500) | 70.1 | 23.3 |

TABLE 24-continued

Tablet Formulation II

| Ingredients | Amounts mg | % |
|---|---|---|
| Croscarmellose sodium, NF (Ac-Di-Sol) | 9.0 | 3.0 |
| Magnesium Stearate, NF | 3.0 | 1.0 |
| Total | 300.0 | 100 |

TABLE 25

Tablet Formulation III

| Ingredients | Amounts mg | % |
|---|---|---|
| A solid form of Compound 1 | 50.0 | 16.7 |
| Lactose anhydrous, NF | 145.1 | 48.3 |
| Microcrystalline cellulose, NF (Avicel pH 101) | 93.1 | 31.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 26

Tablet Formulation IV

| Ingredients | Amounts mg | % |
|---|---|---|
| A solid form of Compound 1 | 50.0 | 16.7 |
| Lactose monohydrate, NF (Fast Flo 316) | 145.0 | 48.3 |
| Microcrystalline cellulose, NF (Avicel pH 102) | 93.0 | 31.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 27

Tablet Formulation V

| Ingredients | Amounts mg | % |
|---|---|---|
| A solid form of Compound 1 | 50.0 | 11.9 |
| Lactose monohydrate, NF (Fast Flo 316) | 220.48 | 52.5 |
| Microcrystalline cellulose, NF (Avicel pH 102) | 130.20 | 31.0 |
| Croscarmellose sodium, NF (Ac-Di-Sol) | 12.6 | 3.0 |
| Stearic acid, NF | 2.52 | 0.6 |
| Magnesium Stearate, NF | 4.20 | 1.0 |
| Total | 420.0 | 100 |

TABLE 28

Tablet Formulation VI

| Ingredients | Amounts mg | % |
|---|---|---|
| A solid form of Compound 1 | 50.0 | 11.9 |
| Lactose monohydrate, NF (Fast Flo 316) | 182.20 | 63.1 |
| Microcrystalline cellulose, NF (Avicel pH 102) | 54.0 | 18.0 |

TABLE 28-continued

Tablet Formulation VI

| Ingredients | Amounts mg | % |
|---|---|---|
| Croscarmellose sodium, NF (Ac-Di-Sol) | 9.0 | 3.0 |
| Stearic acid, NF | 1.80 | 3.0 |
| Magnesium Stearate, NF | 3.0 | 1.0 |
| Total | 300.0 | 100 |

TABLE 29

Tablet Formulation VII

| Ingredients | Amounts mg | % |
|---|---|---|
| A solid form of Compound 1 | 50.0 | 16.7 |
| Lactose monohydrate, NF (Fast Flo 316) | 265.0 | 88.3 |
| Microcrystalline cellulose, NF (Avicel pH 102) | 75.60 | 25.2 |
| Corn starch, NF | 12.6 | 4.2 |
| Croscarmellose sodium, NF (Ac-Di-Sol) | 12.6 | 4.2 |
| Magnesium Stearate, NF | 4.20 | 1.4 |
| Total | 420.0 | 100 |

TABLE 30

Tablet Formulation VIII

| Ingredients | Amounts mg | % |
|---|---|---|
| A solid form of Compound 1 | 50.0 | 16.7 |
| Lactose monohydrate, NF (Fast Flo 316) | 136.0 | 45.3 |
| Microcrystalline cellulose, NF (Avicel pH 102) | 93.0 | 31.0 |
| Corn starch, NF | 9.0 | 3.0 |
| Croscarmellose sodium, NF (Ac-Di-Sol) | 9.0 | 3.0 |
| Magnesium Stearate, NF | 3.0 | 1.0 |
| Total | 300.0 | 100 |

TABLE 31

Tablet Process Parameters

| Equipment/Process Parameters | I | II | III | IV |
|---|---|---|---|---|
| Batch size (kg) | 0.5 | 0.5 | 0.5 | 0.5 |
| Bin blender (quart) | 4 | 4 | 4 | 4 |
| Pre-blending time (min) | 20/10 | 20/10 | 20/10 | 20/10 |
| Lubrication time (min) | 3 | 3 | 3 | 3 |
| Actual weight (mg) | 299 291-309 | 301 295-310 | 307 301-311 | 297 290-300 |
| Bulk density (g/cc) | 0.4 | 0.53 | 0.37 | 0.42 |
| Tooling (round, SC) | 12/32 | 12/32 | 12/32 | 12/32 |
| Hardness (average in Kp) | 7.9 | 4.1 | 7.9 | 7.4 |
| Thickness (average in mm) | 3.95 | 3.86 | 3.98 | 3.86 |
| Friability (4 min) (%) | 0 | 0.1 | 0 | 0.1 |
| Disintegration time (max) (sec) | 18 | 75 | 55 | 21 |
| Observation | Picking | Picking | Picking | Picking |

TABLE 32

Tablet Process Parameters

| Equipment/Process Parameters | V | VI | VII | VIII |
|---|---|---|---|---|
| Batch size (kg) | 0.5 | 0.5 | 0.5 | 0.5 |
| Bin blender used (quart) | 4 | 4 | 4 | 4 |
| Pre-blending time (min) | 20/10 | 20/10 | 20/10 | 20/10 |
| Lubrication time (min) | 3 | 3 | 3 | 3 |
| Actual weight (mg) | 418 | 299 | 419 | 301 |
|  | 413-421 | 293-307 | 413-426 | 296-305 |
| Bulk density (g/cc) | 0.45 | 0.43 | 0.48 | 0.43 |
| Tooling (round, SC) | 12/32 | 12/32 | 12/32 | 12/32 |
| Hardness (average in Kp) | 9.1 | 8.5 | 9.0 | 8.4 |
| Thickness (average in mm) | 5.20 | 3.8 | 4.12 | 3.86 |
| Friability (4 min) (%) | 0.3 | 0.2 | 0.2 | 0.1 |
| Disintegration time (max) (sec) | 31 | 30 | 29 | 20 |
| Observation | None | None | None | None |

Tablet formulations IX to XI of a solid form of Compound 1 are summarized in Table 33 to Table 35. The process parameters for their preparation are summarized in Table 36 and Table 37.

TABLE 33

Tablet Formulation IX

| Ingredients | Amounts mg | % |
|---|---|---|
| A solid form of Compound 1 | 50.0 | 15.4 |
| Lactose monohydrate, NF (Fast Flo 316) | 151.5 | 46.6 |
| Microcrystalline cellulose, NF (Avicel pH 102) | 100.75 | 31.0 |
| Corn starch, NF | 9.75 | 3.0 |
| Croscarmellose sodium, NF (Ac-Di-Sol) | 9.75 | 3.0 |
| Magnesium Stearate, NF | 3.25 | 1.0 |
| Total | 325.0 | 100 |
| Opadry pink 03K140004 | 4% weight gain | |

TABLE 34

Tablet Formulation X

| Ingredients | Amounts mg | % |
|---|---|---|
| A solid form of Compound 1 | 50.0 | 15.4 |
| Lactose monohydrate, NF (Fast Flo 316) | 149.55 | 46.0 |
| Microcrystalline cellulose, NF (Avicel pH 102) | 100.75 | 31.0 |
| Corn starch, NF | 9.75 | 3.0 |
| Croscarmellose sodium, NF (Ac-Di-Sol) | 9.75 | 3.0 |
| Stearic acid, NF | 1.95 | 0.6 |
| Magnesium Stearate, NF | 3.25 | 1.0 |
| Total | 325.0 | 100 |
| Opadry pink 03K140004 | 4% weight gain | |

TABLE 35

Tablet Formulation XI

| Ingredients | Amounts mg | % |
|---|---|---|
| A solid form of Compound 1 | 5.0 | 3.85 |
| Lactose monohydrate, NF (Fast Flo 316) | 74.82 | 57.55 |
| Microcrystalline cellulose, NF (Avicel pH 102) | 40.30 | 31.00 |
| Corn starch, NF | 3.90 | 3.00 |
| Croscarmellose sodium, NF (Ac-Di-Sol) | 3.90 | 3.00 |
| Stearic acid, NF | 0.78 | 0.60 |
| Magnesium Stearate, NF | 1.30 | 1.00 |
| Total | 130.0 | 100 |
| Opadry beige 03K170001 | 4% weight gain | |

TABLE 36

Tablet Process Parameters

| Equipment/Process Parameters Blending/Compression | IX | X | XI |
|---|---|---|---|
| Batch size (kg) | 0.65 | 0.65 | 0.52 |
| Bin blender used (quart) | 4 | 4 | 4 |
| Pre-blending time (min) | 20/10 | 20/10 | 20/10 |
| Lubrication time (min) | 3 | 3 | 3 |
| Actual weight (mg) | 323 | 326 | 131 |
|  | 318-328 | 316-333 | 130-134 |
| Bulk density (g/cc) | 0.40 | 0.42 | 0.48 |
| Tooling (round, SC) | 12/32 | 12/32 | 1/4 |
| Hardness (average in Kp) | 9.3 | 9.1 | 5.9 |
| Thickness (average in mm) | 4.09 | 4.12 | 3.72 |
| Friability (4 min) (%) | 0.1 | 0.1 | 0.1 |
| Disintegration time (max) (sec) | 39 | 27 | 24 |
| Observations | Picking | None | None |

TABLE 37

Tablet Process Parameters

| Equipment/Process Parameters Coating | IX | X | XI |
|---|---|---|---|
| Batch size (kg) | 0.27 | 0.27 | 0.30 |
| Weight gain (%) | 4 | 4 | 4 |
| Solid in suspension (%) | 12 | 12 | 12 |
| Pan (inch) | 8 | 8 | 8 |
| Nozzle size (mm) | 0.8 | 0.8 | 0.8 |
| Atomizing air pressure (PSI) | 9-10 | 10-12 | 9-10 |
| Pattern (PSI) | 12-13 | 12-13 | 11-12 |
| Distance gun-ben (inch) | 3 | 3 | 3 |
| Airflow (CFM) | 75 | 75 | 75 |
| Pan speed (RPM) | 16-18 | 14-17 | 14-17 |
| Inlet temperature (° C.) | 75 | 75 | 72-73 |
| Exhaust temperature (° C.) | 51-53 | 51-53 | 49-50 |
| Spray rate | 5-7 | 4-6 | 4-6 |
| Observation | Acceptable appearance | | |

The 5 mg and 50 mg tablets (core and coated) are subjected to short term stability and photo-stability evaluations. The short term stability of the 50 mg tablets is tested by storing for 2 weeks at 40° C./75% RH in an open bottle.

Tablet formulations XII (50 mg), XIII (20 mg), and XIV (5 mg) are summarized in Table 38, Table 39 and Table 40.

TABLE 38

Tablet Formulation XII (50 mg)

| Ingredients | mg | % |
|---|---|---|
| A solid form of Compound 1 | 50.0 | 15.38 |
| Lactose monohydrate, NF (Fast Flo 316) | 159.95 | 49.22 |
| Microcrystalline cellulose, NF (Avicel pH 102) | 100.75 | 31.00 |
| Croscarmellose sodium, NF (Ac-Di-Sol) | 9.75 | 3.00 |
| Stearic acid, NF | 1.30 | 0.40 |
| Magnesium Stearate, NF | 3.25 | 1.00 |
| Total | 325.0 | 100 |
| Opadry pink 03K140004 | 13.0 | 4% weight gain |

TABLE 39

Tablet Formulation XIII (20 mg)

| Ingredients | mg | % |
|---|---|---|
| A solid form of Compound 1 | 20.0 | 15.38 |
| Lactose monohydrate, NF (Fast Flo 316) | 63.98 | 49.22 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry yellow 03K12429 | 5.2 | 4% weight gain |

TABLE 40

Tablet Formulation XIV (5 mg)

| Ingredients | mg | % |
|---|---|---|
| A solid form of Compound 1 | 5.0 | 3.80 |
| Lactose monohydrate, NF (Fast Flo 316) | 78.98 | 60.70 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry II pink 85F94211 | 5.2 | 4% weight gain |

The 20 mg and 50 mg tablets are compressed at various compression forces to assess compressibility and define a hardness range. The parameters for the preparation of the tablets to assess compressibility are summarized in Table 41 (blending/compression) and Table 42 (coating). The 20 mg tablets are coated with Opadry Yellow 03K12429, whereas the 50 mg tablets are not coated. The core and coated tablets (20 mg) are tested for dissolution.

TABLE 41

Process Parameters for 50 mg and 20 mg Tablet Formulations (Blending/Compression)

| Equipment/Process Parameter | 50 mg | 20 mg |
|---|---|---|
| Batch Size (kg) | 2.21 (Common Blend) | |
| Bin Blende used (quart) | 8 | |
| Pre-blending time (min) | 20/10 | |
| Lubrication time (min) | 3 | 3 |
| Actual weight (mg) | 327 | 129 |
| | 313-339 | 124-135 |
| Bulk density (g/cc) | 0.41 | 0.41 |
| Tooling (round, SC) | 12/32 | 1/4 |
| Hardness (average in Kp) | Hig High-13.6 | High-9.0 |
| | Low-5.9 | Low-3.8 |
| | Target-9.9 | Target-6.1 |
| Thickness (average in mm) | 4.26 | 3.76 |
| Friability (4 min) (%) | 0.09 | 0.04 |
| Disinegration time (max) (sec) | 39 | 22 |
| Observations | None | None |

TABLE 42

Process Parameters for Formulation XIII (Coating)

| Equipment/Process Parameter | 20 mg |
|---|---|
| Batch size (kg) | 0.27 |
| Weight gain (%) | 4 |
| Solid in suspension (%) | 12 |
| Pan (inch) | 8 |
| Nozzle size (mm) | 0.8 |
| Atomizing air pressure (PSI) | 9-10 |
| Pattern (PSI) | 11-12 |
| Distance gun-bed (inch) | 3 |
| Airflow (CFM) | 75 |
| Pan speed (RPM) | 14-16 |
| Inlet temperature (° C.) | 65 |
| Exhaust temperature (° C.) | 45-47 |
| Spray rate | 4-5 |
| Observation | Acceptable coating |

Batch formulations of a solid form of Compound 1 are summarized in Table 43.

TABLE 43

Batch Tablet Formulations

| Ingredients | 5 mg grams | 20 mg grams |
|---|---|---|
| A solid form of Compound 1 | 45.0 | 180.0 |
| Lactose monohydrate | 710.82 | 575.82 |
| Microcrystalline cellulose | 362.70 | 362.70 |
| Croscarmellose sodium | 35.10 | 35.10 |
| Stearic acid | 4.68 | 4.68 |
| Magnesium stearate | 11.70 | 11.70 |
| Total | 1170.0 | 1170.0 |
| Opadry ® II Pink | 65.52 | — |
| Opadry Yellow | — | 65.52 |

Tablet formulation XV (45 mg) is summarized in Table 44. Tablet formulation XV are prepared using methodology provided herein or other methods known to one skilled in the art.

TABLE 44

Tablet Formulation XV (45 mg)

| Ingredients | mg | % |
|---|---|---|
| A solid form of Compound 1 | 45.0 | 15.38 |
| Lactose monohydrate, NF (Fast Flo 316) | 143.955 | 49.22 |

TABLE 44-continued

Tablet Formulation XV (45 mg)

| Ingredients | Amounts mg | % |
|---|---|---|
| Microcrystalline cellulose, NF (Avicel pH 102) | 90.675 | 31.00 |
| Croscarmellose sodium, NF (Ac-Di-Sol) | 8.775 | 3.00 |
| Stearic acid, NF | 1.170 | 0.40 |
| Magnesium Stearate, NF | 2.925 | 1.00 |
| Total | 292.50 | 100 |
| Opadry pink 03K140004 | 11.7 | 4.0% weight gain |

Additionally, A solid form of Compound 1 can be susceptible to hydrolysis. Accordingly, without being limited by theory, a low-moisture grade microcrystalline cellulose (Avicel pH 112) can be used in place of Avicel pH 102 to minimize or prevent hydrolysis.

Tablet formulations XVI (15 mg) and XVII (30 mg) are summarized in Table 45 and Table 46, below. Tablet formulations XVI and XVII are prepared using blending/sieving via a Comil process. After lubrication, the mixture is then compressed into tablets and film-coated.

TABLE 45

Tablet Formulation XVI (15 mg)

| Ingredients | Amounts mg | % |
|---|---|---|
| A solid form of Compound 1 | 15.0 | 15.38 |
| Lactose monohydrate, NF (Fast Flo 316)4 | 8.37 | 49.62 |
| Microcrystalline cellulose, NF (Avicel pH 112) | 30.23 | 31.00 |
| Croscarmellose sodium, NF (Ac-Di-Sol) | 2.925 | 3.00 |
| Magnesium Stearate, NF | 0.975 | 1.00 |
| Total | 97.50 | 100 |
| Opadry II pink 85F94211 | 3.9 | 4% weight gain |

TABLE 46

Tablet Formulation XVII (30 mg)

| Ingredients | Amounts mg | % |
|---|---|---|
| A solid form of Compound 1 | 30.0 | 15.38 |
| Lactose monohydrate, NF (Fast Flo 316) | 96.75 | 49.62 |
| Microcrystalline cellulose, NF (Avicel pH 112) | 60.45 | 31.00 |
| Croscarmellose sodium, NF (Ac-Di-Sol) | 5.85 | 3.00 |
| Magnesium Stearate, NF | 1.95 | 1.00 |
| Total | 195.0 | 100 |
| Opadry pink 03K140004 | 7.8 | 4% weight gain |

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A crystal form comprising the compound of formula (I):

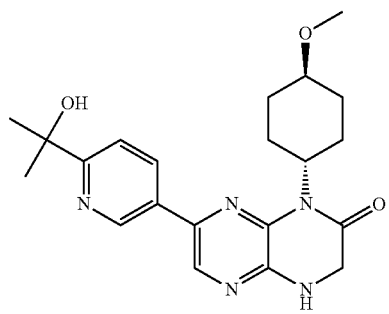

which has an X-ray powder diffraction pattern comprising peaks at approximately 7.14, 11.42 and 22.7° 2θ.

2. The crystal form of claim 1 which has an X-ray powder diffraction pattern further comprising peaks at approximately 12.82, 16.1 and 25.5° 2θ.

3. The crystal form of claim 1 which has a thermogravimetric analysis thermogram comprising no significant mass loss of the total mass of the crystal form between approximately 25° C. to approximately 100° C. when heated from approximately 25° C. to approximately 300° C.

4. The crystal form of claim 1 which has a single differential thermal analysis thermogram comprising an endotherm with a maximum at approximately 187.6° C. when heated from approximately 25° C. to approximately 300° C.

5. The crystal form of claim 1 which is anhydrous.

6. The crystal form of claim 1 which is substantially pure.

7. A crystal form comprising the compound of formula (I):

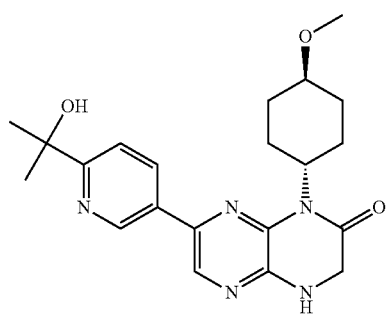

which has an X-ray powder diffraction pattern comprising peaks at approximately 7.42, 18.3 and 23.82° 2θ.

8. The crystal form of claim 7 which has an X-ray powder diffraction pattern further comprising peaks at approximately 10.38, 15.94 and 19.42° 2θ.

9. The crystal form of claim 7 which has a thermogravimetric analysis thermogram comprising a total mass loss of approximately 1.12% of the total mass of the crystal form between approximately 35° C. and approximately 175° C. when heated from approximately 25° C. to approximately 300° C.

10. The crystal form of claim 7 which has a single differential thermal analysis thermogram comprising an endotherm with a maximum at approximately 193.5° C. when heated from approximately 25° C. to approximately 300° C.

11. The crystal form of claim 7 which is water solvated.

12. The crystal form of claim 7 which is a monohydrate.

13. The crystal form of claim 7 which is substantially pure.

14. A crystal form comprising the compound of formula (I):

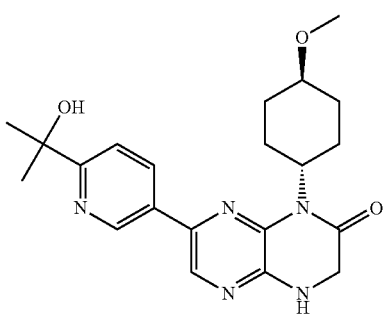

(I)

which has an X-ray powder diffraction pattern comprising peaks at approximately 7.3, 12.78 and 21.9° 2θ.

15. The crystal form of claim 14 which has an X-ray powder diffraction pattern further comprising peaks at approximately 11.86, 16.9 and 18.74° 2θ.

16. The crystal form of claim 14 which has a thermogravimetric analysis thermogram comprising a total mass loss of approximately 5% of the total mass of the crystal form between approximately 25° C. and approximately 100° C. when heated from about 25° C. to about 300° C.

17. The crystal form of claim 14 which has a single differential thermal analysis thermogram comprising an endotherm with a maximum at approximately 67.7° C. when heated from about 25° C. to about 300° C.

18. The crystal form of claim 17 wherein the single differential thermal analysis thermogram further comprises an endotherm with a maximum at approximately 108° C.

19. The crystal form of claim 17 wherein the single differential thermal analysis thermogram further comprises an endotherm with a maximum at approximately 158° C.

20. The crystal form of claim 14 which is water solvated.

21. The crystal form of claim 14 which is substantially pure.

22. A crystal form comprising the compound of formula (I):

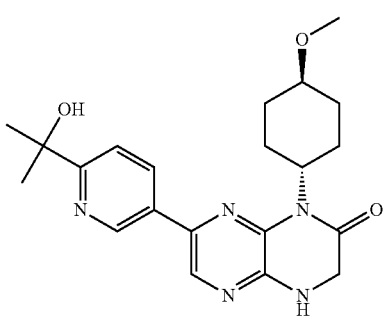

(I)

which has an X-ray powder diffraction pattern comprising peaks at approximately 8.02, 13.82 and 25.02° 2θ.

23. The crystal form of claim 22 which has an X-ray powder diffraction pattern further comprising peaks at approximately 15.58, 19.82 and 21.02° 2θ.

24. The crystal form of claim 22 which has a thermogravimetric analysis thermogram comprising a total mass loss of approximately 1.7% of the total mass of the crystal form between approximately 35° C. and approximately 110° C. when heated from about 25° C. to about 300° C.

25. The crystal form of claim 22 which has a single differential thermal analysis thermogram comprising an endotherm with a maximum at approximately 83.2° C. when heated from about 25° C. to about 300° C.

26. The crystal form of claim 22 which is acetone solvated.

27. The crystal form of claim 22 which is substantially pure.

28. A crystal form comprising the compound of formula (I):

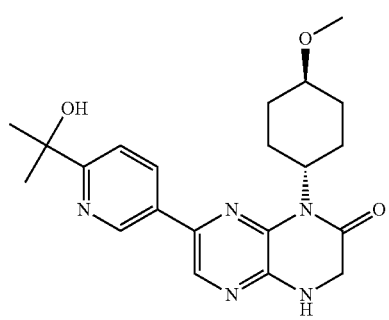

(I)

which has an X-ray powder diffraction pattern comprising peaks at approximately 4.1, 15.78 and 25.78° 2θ.

29. The crystal form of claim 28 which has an X-ray powder diffraction pattern further comprising peaks at approximately 6.34, 8.3 and 20.06° 2θ.

30. The crystal form of claim 28 which has a thermogravimetric analysis thermogram comprising a total mass loss of approximately 4.6% of the total mass of the crystal form between approximately 25° C. and approximately 120° C. when heated from about 25° C. to about 300° C.

31. The crystal form of claim 28 which has a single differential thermal analysis thermogram comprising an endotherm with a maximum at approximately 95.5° C. when heated from about 25° C. to about 300° C.

32. The crystal form of claim 28 which is acetone solvated.

33. The crystal form of claim 28 which is water solvated.

34. The crystal form of claim 28 which is substantially pure.

35. A crystal form comprising the compound of formula (I):

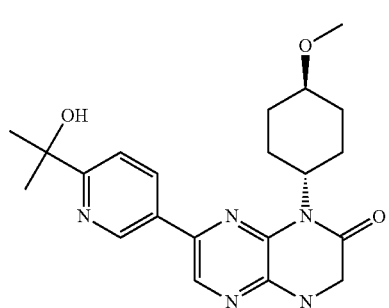

(I)

which has an X-ray powder diffraction pattern comprising peaks at approximately 4.26, 17.78 and 25.82° 2θ.

36. The crystal form of claim 35 which has an X-ray powder diffraction pattern further comprising peaks at approximately 13.02, 13.5 and 21.7° 2θ.

37. The crystal form of claim 35 which has a thermogravimetric analysis thermogram comprising a total mass loss of approximately 0.9% of the total mass of the crystal form between about 70° C. and about 160° C. when heated from about 25° C. to about 300° C.

38. The crystal form of claim 35 which has a single differential thermal analysis thermogram comprising an endotherm with a maximum at approximately 148° C. when heated from about 25° C. to about 300° C.

39. The crystal form of claim 35 which is acetonitrile solvated.

40. The crystal form of claim 35 which is substantially pure.

41. A crystal form comprising the compound of formula (I):

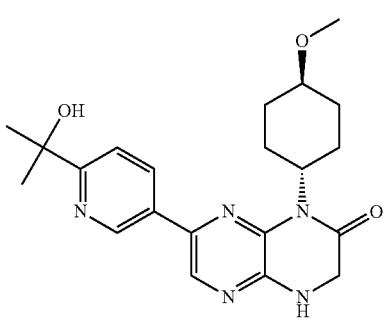

which has an X-ray powder diffraction pattern comprising peaks at approximately 6.54, 13.66, 26.02° 2θ.

42. The crystal form of claim 41 which has an X-ray powder diffraction pattern further comprising peaks at approximately 9.42, 18.42 and 26.82° 2θ.

43. The crystal form of claim 41 which has a thermogravimetric analysis thermogram comprising a total mass loss of approximately 4% of the total mass of the crystal form between approximately 35° C. and approximately 110° C. when heated from about 25° C. to about 300° C.

44. The crystal form of claim 41 which has a single differential thermal analysis thermogram comprising an endotherm with a maximum at approximately 86° C. when heated from about 25° C. to about 300° C.

45. The crystal form of claim 41 which is acetonitrile solvated.

46. The crystal form of claim 41 which is water solvated.

47. The crystal form of claim 41 which is substantially pure.

48. A crystal form comprising the compound of formula (I):

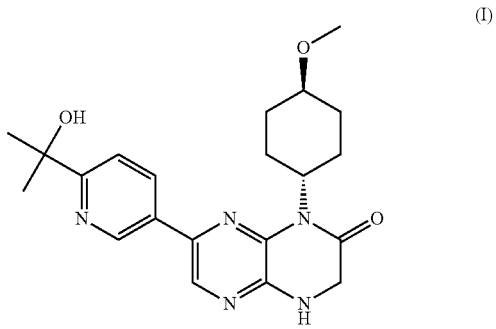 [SMILES: CO[C@H]1CC[C@H](N2C(=O)CNc3ncc(-c4ccc(C(C)(C)O)nc4)nc32)CC1]

which has an X-ray powder diffraction pattern comprising peaks at approximately 6.14, 17.3 and 26.78° 2θ.

49. The crystal form of claim 48 which has an X-ray powder diffraction pattern further comprising peaks at approximately 7.42, 18.46 and 28.38° 2θ.

50. The crystal form of claim 48 which has a thermogravimetric analysis thermogram comprising a total mass loss of approximately 1% of the total mass of the crystal form between about 35° C. and about 110° C. when heated from about 25° C. to about 300° C.

51. The crystal form of claim 48 which has a single differential thermal analysis thermogram comprising an endotherm with a maximum at approximately 118.8° C. when heated from about 25° C. to about 300° C.

52. The crystal form of claim 48 which is ethyl acetate solvated.

53. The crystal form of claim 48 which is substantially pure.

* * * * *